(12) United States Patent
Stegmann et al.

(10) Patent No.: US 10,533,199 B2
(45) Date of Patent: Jan. 14, 2020

(54) [S,S]-EDDS BIOSYNTHESIS GENES AND PROTEINS AND METHOD OF BIOSYNTHESIS OF [S,S]-EDDS

(71) Applicants: Efthimia Stegmann, Rottenburg/Wurmlingen (DE); Wolfgang Wohlleben, Tübingen (DE); Marius Spohn, Tettnang (DE); Tilmann Weber, Tübingen (DE)

(72) Inventors: Efthimia Stegmann, Rottenburg/Wurmlingen (DE); Wolfgang Wohlleben, Tübingen (DE); Marius Spohn, Tettnang (DE); Tilmann Weber, Tübingen (DE)

( * ) Notice: Subject to any disclaimer, the term of this patent is extended or adjusted under 35 U.S.C. 154(b) by 374 days.

(21) Appl. No.: 14/916,211

(22) PCT Filed: Sep. 2, 2014

(86) PCT No.: PCT/EP2014/068612
§ 371 (c)(1),
(2) Date: Mar. 3, 2016

(87) PCT Pub. No.: WO2015/032751
PCT Pub. Date: Mar. 12, 2015

(65) Prior Publication Data
US 2016/0215311 A1    Jul. 28, 2016

(30) Foreign Application Priority Data

Sep. 3, 2013 (DE) .................. 10 2013 217 543

(51) Int. Cl.
| | |
|---|---|
| *C12P 13/04* | (2006.01) |
| *C07K 14/195* | (2006.01) |
| *C12N 9/06* | (2006.01) |
| *C12N 9/02* | (2006.01) |
| *C12N 9/10* | (2006.01) |
| *C12N 9/80* | (2006.01) |
| *C12N 9/88* | (2006.01) |

(52) U.S. Cl.
CPC ............ *C12P 13/04* (2013.01); *C07K 14/195* (2013.01); *C12N 9/0016* (2013.01); *C12N 9/0069* (2013.01); *C12N 9/1029* (2013.01); *C12N 9/80* (2013.01); *C12N 9/88* (2013.01); *C12Y 113/1102* (2013.01); *C12Y 203/01001* (2013.01); *C12Y 401/0102* (2013.01)

(58) Field of Classification Search
None
See application file for complete search history.

(56) References Cited

FOREIGN PATENT DOCUMENTS

| | | |
|---|---|---|
| EP | 0 731 171 | 9/1996 |
| EP | 1 043 400 | 10/2000 |
| WO | 96/36725 A1 | 11/1996 |

OTHER PUBLICATIONS

Stegmann et al.,"Development of three different gene cloning systems for genetic investigation of the new species *Amycolatopsis japonicum* MG417-CF17, the ethylenediaminedisuccinic acid producer", Journal of Biotechnology 92: 195-204 (2001) (Year: 2001).*
John A. Neal et al., "Stereospecific Ligands and their complexes. I. A cobalt(III) complex of ethylenediaminesuccinic acid," Inorganic Chemistry, vol. 7, No. 11, 1968, pp. 2405-2412 (Abstract).
Michael Goodfellow et al., "*Amycolatopsis japonicum* sp. nov., an Actinomycete Producing (S,S)-N,N'-Ethylene3diaminedisuccinic Acid," Systematic and Applied Microbiology, vol. 20, Issue 1, Jan. 1997, pp. 78-84 (Abstract).
Diederik Schowanek et al., "Biodegradation of [S,S], [R,R] and mixed stereoisomers of Ethylene Diamine Disuccinic Acid (EDDS), a transition metal chelator," Chemosphere, vol. 34, Issue 11, Jun. 1997, pp. 2375-2391 (Abstract).
N. Zwicker et al., "Optimization of fermentation conditions for the production of ethylene-diamine-disuccinic acid by *Amycolatopsis orientalis*," Journal of Industrial Microbiology & Biotechnology, vol. 19, No. 4, 1997, pp. 280-285 (Abstract).
Rikiya Takahashi et al., "Production of (S,S)-Ethylenediamine-N,N'-disuccinic Acid from Ehtylenediamine and Fumaric Acid by Bacteria," Bioscience, Biotechnology and Biochemistry, vol. 63, No. 7, Jan. 1999, pp. 1269-1273 (Abstract).
Efthimia Stegmann et al., "Development of three different gene cloning systems for genetic investigation of the new species *Amycolatopsis japonicum* MG417-CF17, the ethylenediaminedisuccinic acid producer," Journal of Biotechnology, vol. 92, Issue 2, Dec. 2001, pp. 195-204 (Abstract).
Biao Tang et al., "ContigScape: a Cytoscape plugin facilitating microbial genome gap closing," BMC Genomics, vol. 14, No. 1, Apr. 2013, pp. 289.
Evi Stegmann et al., "Complete genome sequence of the actinobacterium *Amycolatopsis japonica* MG417-CF17$^T$ (=DSM 44213T) producing (S,S)-N,N-ethylenediaminedisuccinic acid," Journal of Biotechnology, vol. 189, 2014, pp. 46-47 (Abstract).
Official Action dated Apr. 4, 2014 of parent German Application No. 10 2013 217 543.4.
Pósfai, G. et al.: "Versatile Insertion Plasmids for Targeted Genome Manipulations in Bacteria: Isolation, Deletion, and Rescue of the Pathogenicity Island Lee of the *Escherichia coil* O157:H7 Genome," Journal of Bacteriology, Jul. 1997, vol. 179, No. 13, pp. 4426-4428.
Zhao, W. et al.: "Complete Genome Sequence of the Rifamycin SV-Producing *Amycolatopsis mediterranei* U32 Revealed its Genetic Characteristics in Phylogeny and Metabolism," Cell Research, 2010, vol. 20, pp. 1096-1108.

(Continued)

*Primary Examiner* — Anand U Desai
(74) *Attorney, Agent, or Firm* — DLA Piper LLP (US)

(57) ABSTRACT

An isolated protein or peptide, which is functional for a partial synthesis step of the biosynthesis of [S,S]-ethylenediamine-disuccinate, including or composed of an amino acid sequence selected from the group consisting of SEQ ID No. 39, SEQ ID No. 41, SEQ ID No. 43, SEQ ID No. 45, SEQ ID No. 47, SEQ ID No. 49, SEQ ID No. 51, SEQ ID No. 53, and combinations thereof.

4 Claims, 23 Drawing Sheets
Specification includes a Sequence Listing.

(56) References Cited

OTHER PUBLICATIONS

Cebulla, I. et al., "Isolation of chelating agents using *Amycolatopsis orientalis*," Dissertation, *Eberhard Karls Universität Tübingen*, 1995, with English summary.
Third Office Action dated Jul. 10, 2018, of counterpart Chinese Application No. 201480060818.0, along with an English translation.
Genbank Accession No. WP_016336497 dated Jun. 10, 2013.
Genbank Accession No. WP_016336498 dated Jun. 10, 2013.
Genbank Accession No. WP_016336499 dated Jun. 10, 2013.

* cited by examiner

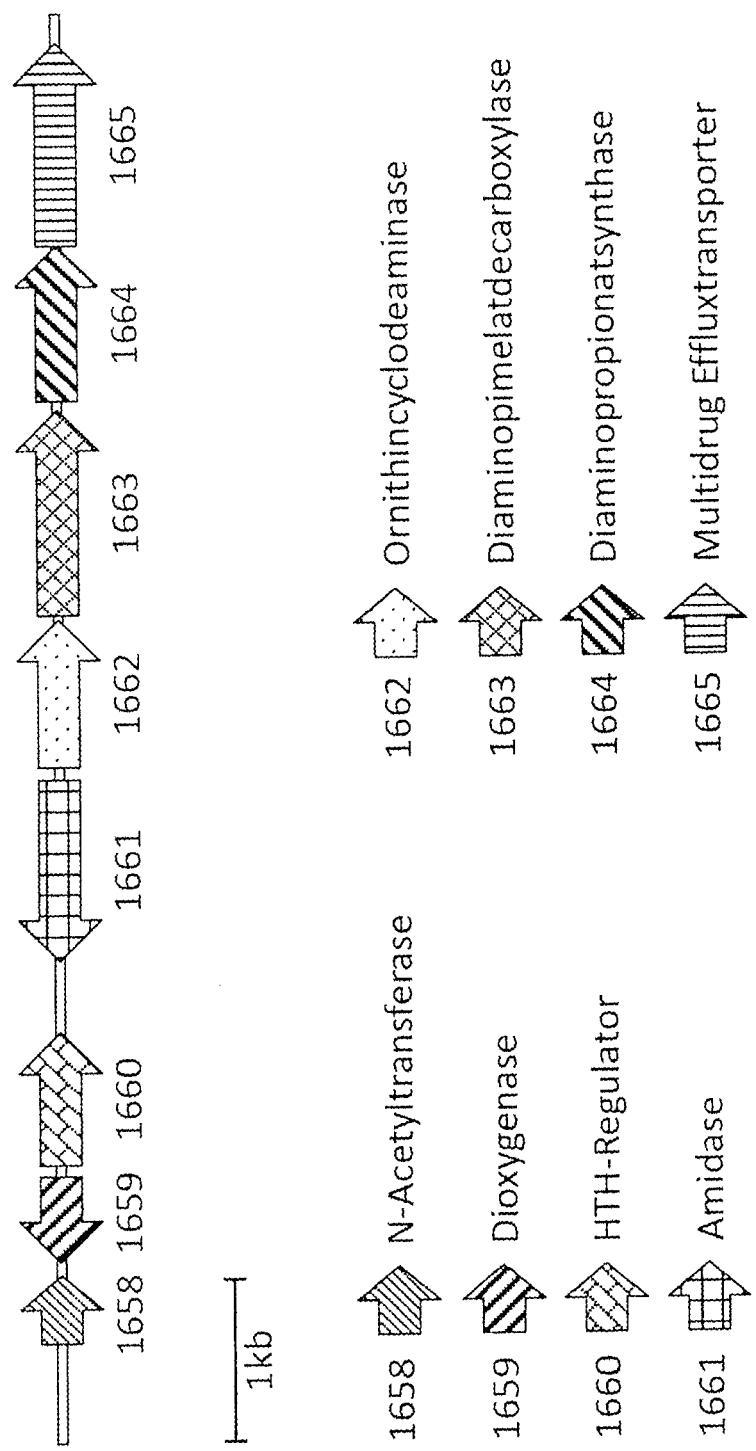
Figur 2A

Figure 6

```
SEQ ID NO. 65  Zur_sc:    N1V--TTA--GPPVKG-RATRQRAAVSAALQEVEEFRSAQELHDMLKHKGDAVGLTTVYRTL
SEQ ID NO. 61  ORF5768:  N1MSPTTANSSAPVPGRRSTKQRAAVELLKEIDDFRSAQELHDELRKRGDGIGLTTVYRTL
                         ---*--|--*-*--*o*o***oo*_|o*********_*oo*o***

SEQ ID NO. 65  Zur_sc:   QSLADAGEVDVLRTAEGESVYRRCSTGDHHHHLVCRACGKAVEVEGPAVEKWAEAIAAEH
SEQ ID NO. 61  ORF5768:  QSLSEAGEIDVLRTDTGEAIYRRCSS-HHHHHLVCRLCGSTVEVEGPAVERWAEKIASEH
                         *o**|-*o*_|*o****o*_-_|*o***********_o**

SEQ ID NO. 65  Zur_sc:   GYVNVAHTVEIFGTCADCAGASGG^139C
SEQ ID NO. 61  ORF5768:  GFSDISHTVEIVGTCSNH^137C
                         *_o_o*****o*****oo_____
```

Figure 7B

|  | S.coelicolor | | | B.subtilis | | |
|---|---|---|---|---|---|---|
|  | ZnuA | ZnuB | ZnuC | MntA | MntB | MntC |
| ORF3699 |  |  | 29/48 |  |  | 27/53 |
| ORF3700 |  | 68/79 |  |  | 32/50 |  |
| ORF3702 | 24/42 |  |  | 27/44 |  |  |
| ORF6504 | 23/40 |  |  | 28/46 |  |  |
| ORF6505 |  |  | 29/45 |  |  | 43/52 |
| ORF6506 |  | 37/53 |  |  | 43/58 |  |

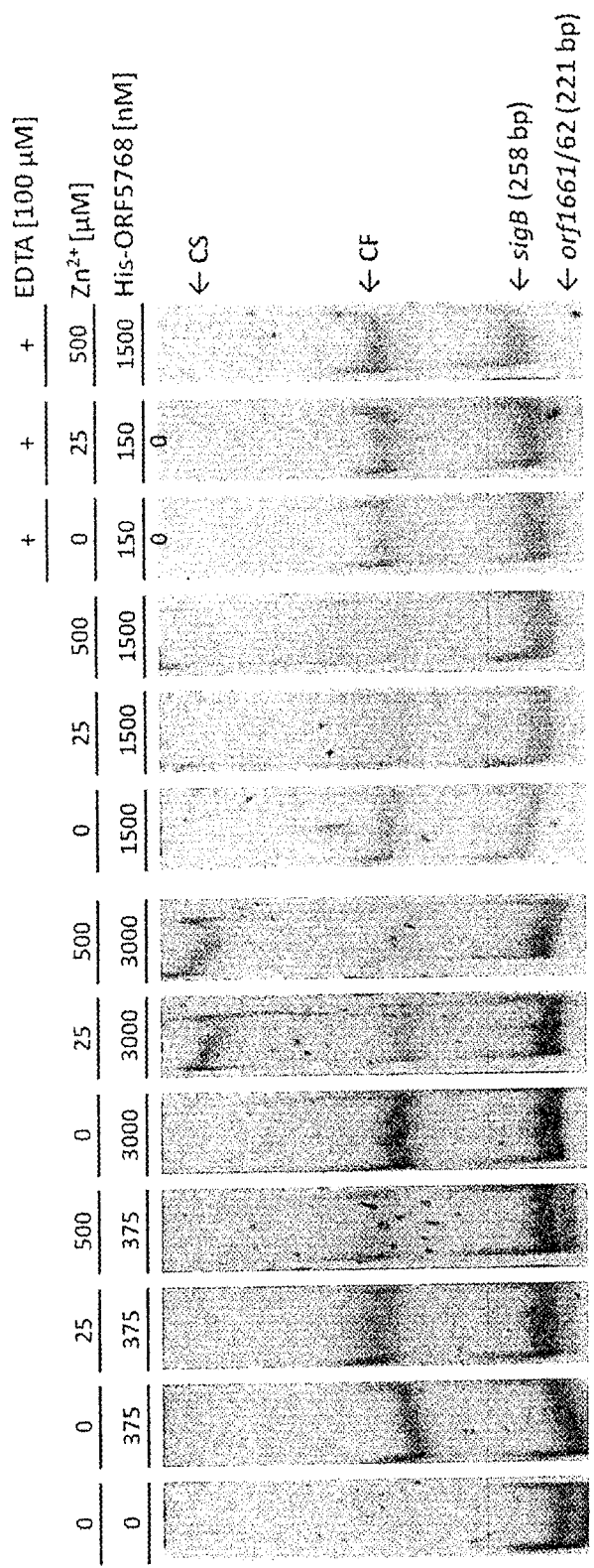

[S,S]-EDDS-Standard

A. japonica WT -Zn(II)

A. japonica WT +Zn(II)

A. japonica Δzur −Zn(II)

A. japonica Δzur +Zn(II)

[S,S]-EDDS BIOSYNTHESIS GENES AND PROTEINS AND METHOD OF BIOSYNTHESIS OF [S,S]-EDDS

SEQUENCE LISTING

The instant application contains a Sequence Listing which has been filed electronically in ASCII format and is hereby incorporated by reference in its entirety. Said ASCII copy, created on Oct. 26, 2018, is named RUF-16-1102 SL.txt and is 135,318 bytes in size.

TECHNICAL FIELD

This disclosure relates to isolated nucleic acids and proteins or peptides for the biosynthesis of [S,S]-ethylenediamine-disuccinate ([S,S]-EDDS), expression and deletion vectors, host cells and deletion mutants of the genus *Amycolatopsis japonicum*, to a method and a kit for the biosynthesis of [S,S]-EDDS.

BACKGROUND

Ethylenediamine-disuccinate (EDDS, also referred to as ethylenediamine disuccinic acid) is a hexadentate chelating agent. EDDS has two stereo centers and, accordingly, presents three different stereoisomers, namely [R,R]-EDDS, [S,S]-EDDS and [R,S]-(meso)-EDDS. It has proved that exclusively the [S,S]-EDDS stereoisomer is subject to complete biological degradation (Schowanek et al., Chemosphere (1997), 34(11):2375-91).

Also, EDDS is a structural isomer of ethylenediamine-tetraacetate (EDTA), a widely-used and likewise hexadentate chelating agent. Both compounds are very similar in their chemical characteristics, in particular in view of their capability of chelating metal ions. Thus, EDDS and EDTA exhibit comparable chelating constants for quite a variety of metal ions.

For many decades, EDTA has been employed for removal of metal ions in most different fields on account of its pronounced chelating capability. At present, it is the most used chelating agent. Particularly stable complexes are formed with copper(II), nickel(II), iron(III) and cobalt(II) ions, but also with heavy metal ions and calcium and magnesium ions.

Therefore, EDTA is in particular added to detergents as a water softener, but is also used to stabilize bleaching liquors in the field of paper and textile industry, and is applied as a fertilizer in the form of iron, copper and zinc complexes thereof. Likewise, EDTA is employed in the medical field to treat heavy metal intoxication.

A drawback is that EDTA is not biodegradable and, thus, may be detected in ubiquitous waters. EDTA is considered to be eco-unfriendly, in particular due to the fact that it can dissolve heavy metals from sediments and make them bioavailable in this way.

With this background it is desirable to replace EDTA by equivalent, however, biologically degradable compounds in terms of sustainable material policy.

EDDS in the form of the biodegradable stereoisomer [S,S]-EDDS represents a generally utile alternative material owing to chelating constants comparable to EDTA.

The chemical synthesis of [S,S]-EDDS starting from L-aspartic acid and 1,2-dibromomethane in the presence of trivalent cobalt is well-known (Neal and Rose, Inorganic Chemistry (1968), 7(11):2405-12). A drawback thereby is the toxic side product hydrogen bromide which needs extensive removal. Moreover, the synthesis is done using fossil educts.

Furthermore, a non-enantioselective chemical method is well-known, wherein maleic acid or maleic anhydride and ethylene diamine are reacted, producing a racemic mixture of [R,R]-EDDS and [S,S]-EDDS together with 50% meso-EDDS. However, due to the low yield of [S,S]-EDDS and the basically very laborious racemate separation, the method is generally inappropriate for industrial application.

A biocatalytic method of producing [S,S]-EDDS is disclosed in EP 0 731 171 A2. Using the procedure described therein, [S,S]-EDDS can be obtained starting from fumaric acid and ethylene diamine under the action of microorganisms exhibiting lysis activity in an optical purity of up to 97%. Another biocatalytic method of producing [S,S]-EDDS is disclosed in EP 1 043 400 A1, wherein [S,S]-EDDS can be obtained starting from maleic acid and ethylene diamine in the presence of microorganisms exhibiting maleate isomerase activity and metal ions in an optical purity of up to 98%. However, both the biocatalytic methods rely on the use of synthetic precursors that cannot be provided by the microorganisms themselves.

Furthermore well-known is the biosynthesis of [S,S]-EDDS using the bacteria species *Amycolatopsis japonicum* (Zwicker et al., Journal of Industrial Microbiology & Biotechnology (1997); 19(4):280-285). However, a drawback thereby is that the biosynthesis is zinc-dependent, and a zinc concentration as low as 2 µM in the culture medium is capable of causing an almost complete disruption of the [S,S]-EDDS synthesis (Cebulla I., Thesis (1995), University of Tubingen).

A method using zinc-free reaction conditions to produce [S,S]-EDDS by *Amycolatopsis japonicum* and using an optimized culture medium is described in WO 96/36725 A1.

In particular the fact that application of the synthesis procedures in a large scale has proved to be complicated and uneconomical due to the zinc dependency and low yields related thereto, is an issue with the generic biosynthesis methods for [S,S]-EDDS. Indeed, generating a zinc-free environment in culture media and fermenters entails considerable expenses and is almost impossible.

With this background, it could therefore be helpful to provide proteins or peptides, nucleic acids, gene clusters, vectors, host cells, bacterial cells, and a method and a kit for the biosynthesis of [S,S]-EDDS.

SUMMARY

We provide an isolated protein or peptide, which is functional for a partial synthesis step of the biosynthesis of [S,S]-ethylenediamine-disuccinate, including or composed of an amino acid sequence selected from the group consisting of SEQ ID No. 39, SEQ ID No. 41, SEQ ID No. 43, SEQ ID No. 45, SEQ ID No. 47, SEQ ID No. 49, SEQ ID No. 51, SEQ ID No. 53, and combinations thereof.

We also provide an isolated nucleic acid, including or composed of a nucleic acid sequence selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof.

We further provide an isolated protein or peptide, produced by expression of a gene, including or composed of a nucleic acid sequence selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof.

We also further provide an isolated gene cluster or operon, including or composed of at least two nucleic acid sequences selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof.

We also further provide an isolated protein or peptide, which is functional for repression of the biosynthesis of [S,S]-ethylenediamine-disuccinate, including or composed of an amino acid sequence according to SEQ ID No. 61.

We also further provide an isolated nucleic acid, including or composed of a nucleic acid sequence according to SEQ ID No. 62.

We also further provide an isolated protein or peptide, produced by expression of a gene, including or composed of a nucleic acid sequence according to SEQ ID No. 62.

We also further provide a bacterial cell of the genus *Amycolatopsis* not expressing a protein or peptide, including or composed of an amino acid sequence according to SEQ ID No. 61, and/or not including a nucleic acid, including or composed of a nucleic acid sequence according to SEQ ID No. 62.

We also further provide a vector for inducing deletion of a nucleic acid sequence from a wild-type genome, of a bacterial cell of the genus *Amycolatopsis* characterized in that the nucleic acid sequence is the sequence according to SEQ ID No. 62, and the vector includes at least one nucleic acid sequence located upstream in the genome of the bacterial cell in relation to the nucleic acid sequence according to SEQ ID No. 62, and/or at least one nucleic acid sequence located downstream in the genome of the bacterial cell in relation to the nucleic acid sequence according to SEQ ID No. 62, but not including the nucleic acid sequence according to SEQ ID No. 62.

We also further provide a method for the biosynthesis of [S,S]-ethylenediamine-disuccinate, including: a) cultivating a host cell producing [S,S]-ethylenediamine-disuccinate, including at least one protein or peptide according to claim 17, at least one nucleic acid, including or composed of a nucleic acid sequence selected from the group consisting of a) a nucleic acid sequence encoding for a protein or peptide, which is functional for a partial synthesis step of the biosynthesis of [S,S]-ethylenediamine-disuccinate, including or composed of an amino acid sequence selected from the group consisting of SEQ ID No. 39, SEQ ID No. 41, SEQ ID No. 43, SEQ ID No. 45, SEQ ID No. 47, SEQ ID No. 49, SEQ ID No. 51, SEQ ID No. 53, and combinations thereof; b) a nucleic acid sequence differing from the nucleic acid sequence according to a) in the exchange of at least one codon for a synonymous codon; and c) a nucleic acid sequence corresponding to the complementary strand of the nucleic acid sequence according to a), and combinations thereof; a gene cluster or operon, including or composed of at least two nucleic acid sequences selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof, and/or an expression vector, including at least one nucleic acid, including or composed of a nucleic acid sequence selected from the group consisting of a) a nucleic acid sequence encoding for a protein or peptide, which is functional for a partial synthesis step of the biosynthesis of [S,S]-ethylenediamine-disuccinate, including or composed of an amino acid sequence selected from the group consisting of SEQ ID No. 39, SEQ ID No. 41, SEQ ID No. 43, SEQ ID No. 45, SEQ ID No. 47, SEQ ID No. 49, SEQ ID No. 51, SEQ ID No. 53, and combinations thereof; b) a nucleic acid sequence differing from the nucleic acid sequence according to a) in the exchange of at least one codon for a synonymous codon; and c) a nucleic acid sequence corresponding to the complementary strand of the nucleic acid sequence according to a), and combinations thereof; and a gene cluster or operon, including or composed of at least two nucleic acid sequences selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof or a bacterial cell producing [S,S]-ethylenediamine-disuccinate of the genus *Amycolatopsis* not expressing a protein or peptide, including or composed of an amino acid sequence according to SEQ ID No. 61, and/or not including a nucleic acid, including or composed of a nucleic acid sequence according to SEQ ID No. 62, and b) purifying [S,S]-ethylenediamine-disuccinate from the cell and/or a culture medium used for the cell.

BRIEF DESCRIPTION OF THE DRAWINGS

FIGS. 2A-2C show the [S,S]-EDDS biosynthesis pathway with respective biosynthesis genes and the respective gene cluster. (A) Gene organization of the [S,S]-EDDS biosynthesis gene cluster. N-acetyltransferase (SEQ ID No. 40 (orf1658)), cysteine dioxygenase (SEQ ID No. 42 (orf1659)), HTH-type transcriptional regulator (SEQ ID No. 44 (orf1660)), amidase (SEQ ID No. 46 (orf1661)), ornithine cyclodeaminase (SEQ ID No. 48 (orf1662)), diaminopimelate decarboxylase (SEQ ID No. 50 (orf1663)), Dap synthase (SEQ ID No. 52 (orf1664)), and multidrug-efflux transporter (SEQ ID No. 54 (orf1665)). (B) Providing precursors of Dap by converting L-serine with L-ornithine as aminodonor and PLP as cofactor catalyzed by concerted action of ornithine cyclodaminase and a Dap synthase. (C) Assembly of the precursors Dap and two oxalacetates to [S,S]-EDDS. Arrows are marked with corresponding genes in gene cluster (A).

FIG. 6 shows an amino acid alignment of *S. coelicolor* Zur ($Zur_{SC}$) and *A. japonicum* ORF5768 (SEQ ID No. 62). (Top) $Zur_{SC}$ monomer: DNA Binding $Domain_N$ (residues 1-77) not underlined; hinge loop (residues 78-85) solid underlined; Dimerization $Domain_C$ (residues 86-139) dotted underlined. Identical amino acids marked by asterisk (*); similar residues marked by circle (°). Zinc binding sites: arrow: $Zur_{SC}$: D65, C79, H85, H87 and ORF5768: D70, C84, H89 and H91. Aberration of relative aa distances within M-site (marked M). D-site (marked D): $Zur_{SC}$: H84, H86, E105, H122 and ORF5768: H88, H90, E109, H126. C-site (marked C): $Zur_{SC}$: C90, C93, C130, C133 and ORF5768: C94, C97, C134, H137.

FIGS. 7A-7B show a BLAST alignment of *S. coelicolor* ZnuABC and *B. subtilis* MntABC with *A. japonicum* homologues. (A) Gene organization of *S. coelicolor* ZnuABC, the operon-like structures orf3699, orf3700, orf3702 and orf6504, orf6505, orf6506 of *A. japonicum*. (B) Amino acid alignment, (Top) ORF3699, ORF3700 and ORF3702. (Bottom) ORF6504, ORF6505 and ORF6506 vs. *S. coelicolor* ZnuABC (left); vs. *B. subtilis* MntABC (right). X/X=% identity/similarity.

FIGS. 10A-10D show the results of an EMS Assay (polyacrylamide gels with ethidium bromide staining): zinc-dependent binding of purified $His_6$-ORF5768 to promoter regions. Two distinct binding events with different mobilities were designated as CF (fast moving complex) and CS (slow moving complex). To confirm the specificity of binding complexes sigB-RT fragment was added to binding mixture. Purified $His_6$-ORF5768 at various concentrations was incubated with approximately 35 nM DNA probe in absence or presence of zinc ($ZnSO_4$). (A) Binding assay with znuCB probe (cf. FIG. 9). Binding event represented by CF band. (B) Binding assay with intergenic orf1661/62 probe (cf. FIG. 9). Two binding events are represented by CF and CS band, respectively. (C) Binding assay with orf1658 promoter probe and elevated His-ORF5768 concentrations (cf. FIG. 9). (D) Binding assay with intergenic orf1659/60 promoter probe (cf. FIG. 9). Binding event is represented by CS band.

FIG. 13A shows [S,S]-EDDS standard [350 mg/L]. FIGS. 13B and 13C show *A. japonicum* WT –/+6 µM $ZnSO_4$. FIGS. 13F and 13G show *A. japonicum* Δzur –/+6 $ZnSO_4$. FIGS. 13D, 13E, 13H and 13I show specific UV/VIS spectra of [S,S]-EDDS.

DETAILED DESCRIPTION

Figure 1A:
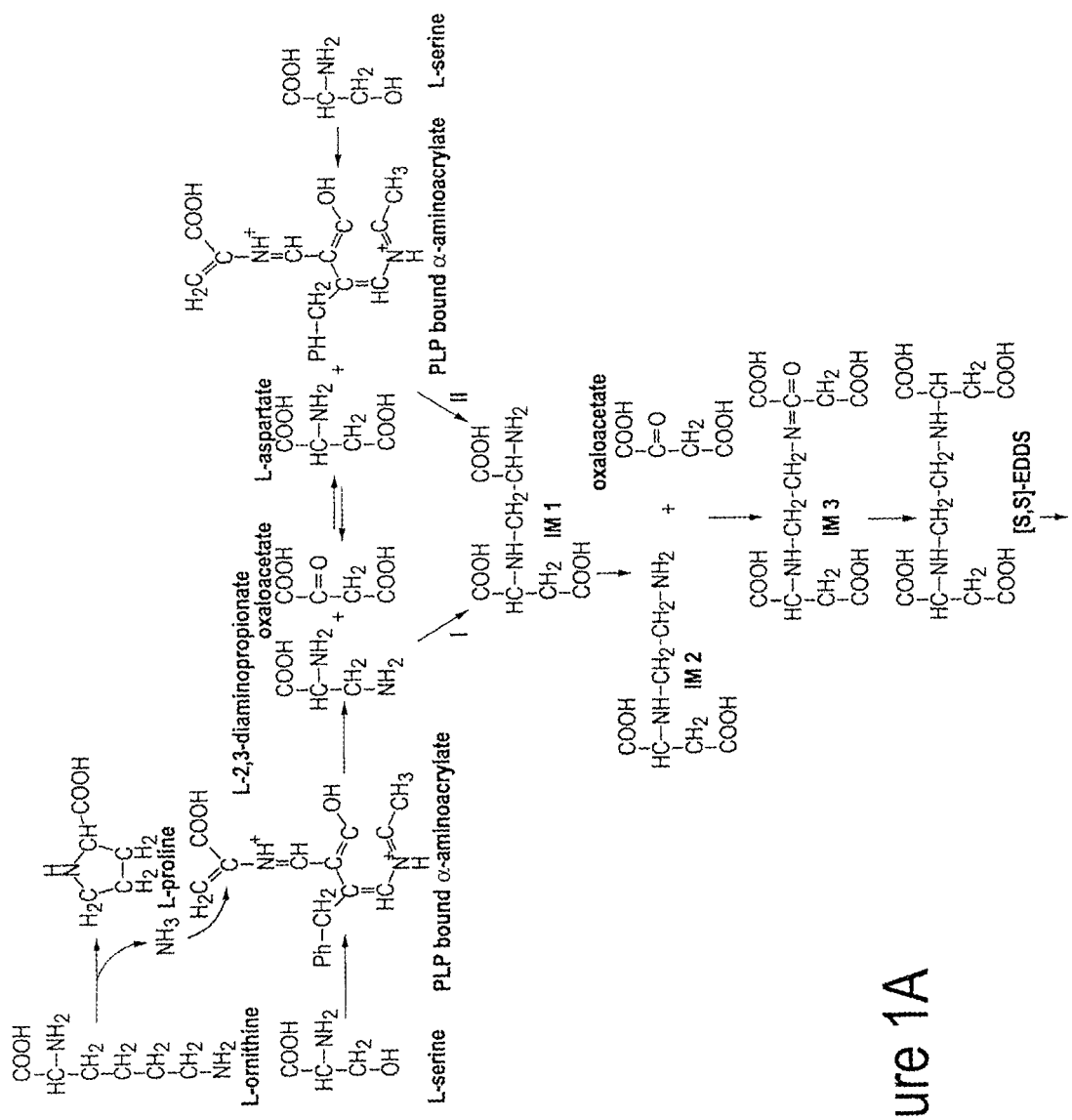
FIGS. 1A-1B show schematic representations of the putative [S,S]-EDDS biosynthesis pathway. (A) [S,S]-EDDS biosynthesis pathway. (I) Providing the precursor Dap; converting L-serine with L-ornithine as aminodonor and PLP as cofactor, thereby releasing L-proline. Dap reacts with oxaloacetic acid to IM1. (II) L-aspartate and L-serine react in the presence of PLP as a cofactor to IM1. (B) Chemical structure of zwittermicin A (left). The dashed-line box indicates the Dap building block. The biosynthesis pathway of Dap (right) is catalyzed by concerted action of zwittermicin A5A (ZWA5A, homologue of the cysteine synthetase) and of zwittermicin A5B (ZWA5B, homologue of the ornithine cyclodeaminase).

We identified and provide genes and proteins using the example of *Amycolatopsis japonicum*, which genes and proteins are responsible for the biosynthesis of [S,S]-ethylenediamine-disuccinate, referred to as [S,S]-EDDS below.

Furthermore, we elucidated the mechanism of the zinc dependency involved in the biosynthesis.

With particular advantage, a more economic and more efficient production of [S,S]-EDDS, in particular with higher yields and increased purity, as compared to generic methods, is thereby provided.

We provide an isolated protein or peptide, which preferably is functional for a partial synthesis step of the biosynthesis of [S,S]-EDDS, i.e., allows performing such a partial synthesis step.

The term "biosynthesis" defines not only an intracellular synthesis of [S,S]-EDDS, but comprises also uptake into a cell and discharge from a cell (transport via a cell membrane).

The protein or peptide includes or is composed of an amino acid sequence selected from the group consisting of SEQ ID No. 1, SEQ ID No. 3, SEQ ID No. 5, SEQ ID No.

7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, SEQ ID No. 43, SEQ ID No. 45, SEQ ID No. 47, SEQ ID No. 49, SEQ ID No. 51, SEQ ID No. 53, SEQ ID No. 55, SEQ ID No. 57, and SEQ ID No. 59.

The term "protein" may refer not only to one distinct protein or peptide, but also to a combination of a plurality of different proteins or peptides.

A protein or peptide can be produced by chemical or recombinant, i.e., biotechnological means.

As an alternative, a protein or peptide can originate from a bacterium, in particular a gram-positive bacterium, preferably from a bacterium of the genus *Amycolatopsis*, particularly preferred from a bacterium of the species *Amycolatopsis japonicum*, or be taken from such a bacterium.

Preferably, the protein or peptide includes or is composed of an amino acid sequence selected from the group consisting of SEQ ID No. 39, SEQ ID No. 41, SEQ ID No. 43, SEQ ID No. 45, SEQ ID No. 47, SEQ ID No. 49, SEQ ID No. 51, and SEQ ID No. 53.

Preferably, a protein or peptide including or composed of any of the amino acid sequences given below has the respectively annotated activity:
 SEQ ID No. 1 2-isopropylmalate synthase activity,
 SEQ ID No. 3 fumarylacetoacetate hydrolase activity,
 SEQ ID No. 5 tRNA uridine-5-carboxymethylaminomethyl modification enzyme activity,
 SEQ ID No. 7 phosphoglycolate phosphatase activity,
 SEQ ID No. 13 alcohol dehydrogenase/L-threonine dehydrogenase activity,
 SEQ ID No. 17 transcription regulatory (PadR-like) activity,
 SEQ ID No. 21 major facilitator superfamily (MFS) activity,
 SEQ ID No. 23 major facilitator superfamily (MFS) activity,
 SEQ ID No. 25 transcription regulatory (HTH, ArsR) activity,
 SEQ ID No. 27 bialaphos biosynthesis pathway regulatory activity,
 SEQ ID No. 29 furin activity,
 SEQ ID No. 33 DNA binding activity (helix-turn-helix, HTH),
 SEQ ID No. 37 two-component transcription regulatory (LuxR) activity,
 SEQ ID No. 39 N-acetyltransferase activity,
 SEQ ID No. 41 cysteine dioxygenase (EC 1.13.11.20) activity,
 SEQ ID No. 43 HTH-type transcription regulatory activity,
 SEQ ID No. 45 amidase (EC 3.5.1.4.) activity,
 SEQ ID No. 47 ornithine cycloamidase (EC 1.4.1.12) activity,
 SEQ ID No. 49 diaminopimelate decarboxylase (EC 4.1.1.20) activity,
 SEQ ID No. 51 cystathionine-ß-synthase (EC 4.2.1.22) activity,
 SEQ ID No. 53 transporter protein activity,
 SEQ ID No. 55 spore formation activity,
 SEQ ID No. 57 ferric uptake regulatory activity,
 SEQ ID No. 59 catalase/peroxidase activity.

The protein or peptide including or composed of an amino acid sequence according to SEQ ID No. 53 is in particular responsible for the transport of [S,S]-EDDS or [S,S]-EDDS-zinc-complex from a cell and/or into a cell, or is at least involved in the transport.

As an alternative, a protein or peptide can be a homologous protein or peptide which has a sequence identity, i.e., an identity in the sequence of amino acids, of at least 65%, in particular of at least 75%, preferably of at least 85%, particularly preferred of at least 95%, most preferred of at least 98%, in relation to any of the above mentioned amino acid sequences.

We also provide an isolated nucleic acid, preferably encoding for a protein or peptide, which is functional for a partial synthesis step of the biosynthesis of [S,S]-EDDS, i.e., allows performing such a partial synthesis step.

The nucleic acid includes or is composed of a nucleic acid sequence selected from the group consisting of
 a) a nucleic acid sequence encoding for a protein or peptide, including or composed of an amino acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, SEQ ID No. 43, SEQ ID No. 45, SEQ ID No. 47, SEQ ID No. 49, SEQ ID No. 51, SEQ ID No. 53, SEQ ID No. 55, SEQ ID No. 57, and SEQ ID No. 59;
 b) a nucleic acid sequence differing from the nucleic acid sequence according to a) in the exchange of at least one codon for a synonymous codon;
 c) a nucleic acid sequence corresponding to the complementary strand of the nucleic acid sequence according to a); and
 d) a nucleic acid sequence encoding for a homologous protein or peptide which has a sequence identity of at least 65%, in particular of at least 75%, preferably of at least 85%, particularly preferred of at least 95%, most preferred of at least 98%, in relation to any of the above mentioned amino acid sequences.

The term "nucleic acid" may refer not only to one distinct nucleic acid, but also to a combination of a plurality of different nucleic acids.

Furthermore, the term "nucleic acid" may refer to a DNA or RNA. A nucleic acid can in particular be selected from the group consisting of gene or open reading frame (ORF), cDNA and mRNA.

A nucleic acid can be produced by chemical or recombinant, i.e., gene technological means.

As an alternative, a nucleic acid can originate from a bacterium, in particular a gram-positive bacterium, preferably from a bacterium of the genus *Amycolatopsis*, particularly preferred from a bacterium of the species *Amycolatopsis japonicum*, or be taken from such a bacterium.

We further provide an isolated nucleic acid, preferably encoding for a protein or peptide, which is functional for a partial synthesis step of the biosynthesis of [S,S]-EDDS, i.e., allows performing such a partial synthesis step, wherein the nucleic acid includes or is composed of a nucleic acid sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42, SEQ ID No. 44, SEQ ID No. 46, SEQ ID No. 48, SEQ ID No. 50, SEQ ID No. 52, SEQ ID No. 54, SEQ ID No. 56, SEQ ID No. 58, and SEQ ID No. 60.

As an alternative, the nucleic acid can be a homologous nucleic acid which has a sequence identity, i.e., an identity in the sequence of nucleotides, of at least 65%, in particular of at least 75%, preferably of at least 85%, particularly preferred of at least 95%, most preferred of at least 98%, in relation to any of the nucleic acid sequences mentioned in the previous paragraph.

The above mentioned nucleic acid sequences preferably encode as given below:

SEQ ID No. 2 for an amino acid sequence according to SEQ ID No. 1;
SEQ ID No. 4 for an amino acid sequence according to SEQ ID No. 3;
SEQ ID No. 6 for an amino acid sequence according to SEQ ID No. 5;
SEQ ID No. 8 for an amino acid sequence according to SEQ ID No. 7;
SEQ ID No. 10 for an amino acid sequence according to SEQ ID No. 9;
SEQ ID No. 12 for an amino acid sequence according to SEQ ID No. 11;
SEQ ID No. 14 for an amino acid sequence according to SEQ ID No. 13;
SEQ ID No. 16 for an amino acid sequence according to SEQ ID No. 15;
SEQ ID No. 18 for an amino acid sequence according to SEQ ID No. 17;
SEQ ID No. 20 for an amino acid sequence according to SEQ ID No. 19;
SEQ ID No. 22 for an amino acid sequence according to SEQ ID No. 21;
SEQ ID No. 24 for an amino acid sequence according to SEQ ID No. 23;
SEQ ID No. 26 for an amino acid sequence according to SEQ ID No. 25;
SEQ ID No. 28 for an amino acid sequence according to SEQ ID No. 27;
SEQ ID No. 30 for an amino acid sequence according to SEQ ID No. 29;
SEQ ID No. 32 for an amino acid sequence according to SEQ ID No. 31;
SEQ ID No. 34 for an amino acid sequence according to SEQ ID No. 33;
SEQ ID No. 36 for an amino acid sequence according to SEQ ID No. 35;
SEQ ID No. 38 for an amino acid sequence according to SEQ ID No. 37;
SEQ ID No. 40 for an amino acid sequence according to SEQ ID No. 39;
SEQ ID No. 42 for an amino acid sequence according to SEQ ID No. 41;
SEQ ID No. 44 for an amino acid sequence according to SEQ ID No. 43;
SEQ ID No. 46 for an amino acid sequence according to SEQ ID No. 45;
SEQ ID No. 48 for an amino acid sequence according to SEQ ID No. 47;
SEQ ID No. 50 for an amino acid sequence according to SEQ ID No. 49;
SEQ ID No. 52 for an amino acid sequence according to SEQ ID No. 51;
SEQ ID No. 54 for an amino acid sequence according to SEQ ID No. 53;
SEQ ID No. 56 for an amino acid sequence according to SEQ ID No. 55;
SEQ ID No. 58 for an amino acid sequence according to SEQ ID No. 57;
SEQ ID No. 60 for an amino acid sequence according to SEQ ID No. 59.

Preferably, the nucleic acid includes or is composed of a nucleic acid sequence selected from the group consisting of SEQ ID No. 40, SEQ ID No. 42, SEQ ID No. 44, SEQ ID No. 46, SEQ ID No. 48, SEQ ID No. 50, SEQ ID No. 52, and SEQ ID No. 54.

We further provide an isolated protein or peptide which is preferably functional for a partial synthesis step of the biosynthesis of [S,S]-EDDS, i.e., allows performing such a partial synthesis step, wherein the protein or peptide is produced by expression of a gene or open reading frame, and the gene or open reading frame includes or is composed of a nucleic acid sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42, SEQ ID No. 44, SEQ ID No. 46, SEQ ID No. 48, SEQ ID No. 50, SEQ ID No. 52, SEQ ID No. 54, SEQ ID No. 56, SEQ ID No. 58, and SEQ ID No. 60.

As an alternative, the protein or peptide can be produced by expression of a homologous gene or open reading frame which has a sequence identity, i.e., an identity in the sequence of nucleotides, of at least 65%, in particular of at least 75%, preferably of at least 85%, particularly preferred of at least 95%, most preferred of at least 98%, in relation to any of the nucleic acid sequences mentioned in the previous paragraph.

Preferred is the production of the protein or peptide by expression of a gene or open reading frame which includes or is composed of a nucleic acid sequence selected from the group consisting of SEQ ID No. 40, SEQ ID No. 42, SEQ ID No. 44, SEQ ID No. 46, SEQ ID No. 48, SEQ ID No. 50, SEQ ID No. 52, and SEQ ID No. 54.

We still further provide an isolated gene cluster or an operon, which is preferably functional for the biosynthesis of [S,S]-EDDS, i.e., allows performing of such a biosynthesis.

The above mentioned operon generally further includes a promoter and, in particular, one or a plurality of operators, as required.

The gene cluster or operon includes or is composed of at least two nucleic acid sequences selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42, SEQ ID No. 44, SEQ ID No. 46, SEQ ID No. 48, SEQ ID No. 50, SEQ ID No. 52, SEQ ID No. 54, SEQ ID No. 56, SEQ ID No. 58, SEQ ID No. 60, and combinations thereof.

The gene cluster or operon can, in particular, include all of the nucleic acid sequences mentioned in the previous paragraph, or be composed of the sequences.

Instead of the above mentioned nucleic acid sequences the gene cluster or operon can also include or be composed of homologous nucleic acid sequences which have a sequence identity, i.e., an identity in the sequence of nucleotides, of at least 65%, in particular of at least 75%, preferably of at least 85%, particularly preferred of at least 95%, most preferred of at least 98%, in relation to any of the nucleic acid sequences mentioned in the previous paragraph.

Preferably, the gene cluster or operon includes or is composed of at least two nucleic acid sequences selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof.

The designation gene cluster originates from the finding that bacteria and many eukaryotes generally use a coordinated mechanism for regulating such genes, with the products thereof (proteins or peptides) being involved in coherent processes, like a biosynthesis, for example. Such genes are located together on a single chromosome in structures referred to as gene clusters and can be subject to cotranscription under the control of a single regulatory sequence or a plurality of regulatory sequences. A gene cluster can in principle also include a plurality of promoters and also be controlled by a plurality of regulators. A gene cluster, a promoter and further sequences, as required, cooperating during regulation, can also be referred to as an operon.

We yet further provide an isolated protein or peptide, which preferably is functional for an inhibition or repression of the biosynthesis of [S,S]-EDDS, i.e., allows such an inhibition or repression. Preferably, the protein or peptide is a transcription inhibitor or repressor for the biosynthesis of [S,S]-EDDS.

The protein or peptide includes or is composed of an amino acid sequence according to SEQ ID No. 61.

As an alternative, the protein or peptide can include or be composed of a homologous amino acid sequence which has a sequence identity of at least 65%, in particular of at least 75%, preferably of at least 85%, particularly preferred of at least 95%, most preferred of at least 98%, in relation to the amino acid sequence mentioned in the previous paragraph.

The protein is preferably a zinc uptake regulator protein, a so-called Zur (zinc uptake regulator) protein, i.e., a protein exhibiting regulatory activity for the cellular uptake of zinc. In general, a Zur protein is capable of binding zinc ions exceeding a certain concentration and of regulating the zinc balance in a bacterial cell by zinc-dependent gene repression or gene expression. The zinc-dependent regulation of genes is mediated in many bacteria in that a zinc-saturated Zur protein, a so-called holoZur protein, binds to specific nucleic acid sequences upstream of the respective target genes so that the enzyme RNA polymerase, which is essential for the transcription of target genes, is denied access thereto. In this way, the transcription of target genes is prevented. The specific nucleic acid sequences acting as Zur binding site are in general promoters/promoter regions or operators.

Since the zinc-dependent regulation of gene repression or gene expression is controlled by the concentration of zinc ions within the cell interior and outside the cell, such systems are in particular also suited for reporter systems in determining a zinc ion concentration.

Surprisingly, we found, as will be explained in more detail below in the exemplary section, using the example of *Amycolatopsis japonicum* that the target genes which are repressed in the presence of zinc by the protein or peptide, including or composed of the amino acid sequence according to SEQ ID No. 61, are biosynthesis genes for the production of [S,S]-EDDS, inter alia. As to the nucleic acid sequences of the biosynthesis genes, reference is made to the above description of the sequences.

We still further provide an isolated nucleic acid, preferably encoding for a protein or peptide, which is functional for an inhibition or repression of the biosynthesis of [S,S]-EDDS, i.e., allows such an inhibition or repression.

The nucleic acid includes or is composed of a nucleic acid sequence selected from the group consisting of
a) a nucleic acid sequence encoding for a protein or peptide including or composed of an amino acid sequence according to SEQ ID No. 61;
b) a nucleic acid sequence differing from the nucleic acid sequence according to a) in the exchange of at least one codon for a synonymous codon;
c) a nucleic acid sequence corresponding to the complementary strand of the nucleic acid sequence according to a); and
d) a nucleic acid sequence encoding for a homologous protein or peptide which has a sequence identity of at least 55%, in particular of at least 75%, preferably of at least 85%, particularly preferred of at least 95%, most preferred of at least 98%, in relation to the amino acid sequence according to SEQ ID No. 61.

Furthermore, we also provide an isolated nucleic acid, preferably encoding for a protein or peptide, which is functional for an inhibition or repression of the biosynthesis of [S,S]-EDDS, i.e., allows such an inhibition or repression, and includes or is composed of a nucleic acid sequence according to SEQ ID No. 62.

As an alternative, the nucleic acid can be a homologous nucleic acid which has a sequence identity of at least 65%, in particular of at least 75%, preferably of at least 85%, particularly preferred of at least 95%, most preferred of at least 98%, in relation to the nucleic acid sequence mentioned in the previous paragraph.

Further, we provide an isolated protein or peptide, which is preferably functional for an inhibition or repression of the biosynthesis of [S,S]-EDDS, i.e., allows such an inhibition or repression, and is produced by expression of a gene or open reading frame, including or composed of a nucleic acid sequence according to SEQ ID No. 62.

As an alternative, the protein or peptide can be produced by expression of a homologous gene or open reading frame having a sequence identity, i.e., an identity in the sequence of nucleotides, of at least 65%, in particular of at least 75%, preferably of at least 85%, particularly preferred of at least 95%, most preferred of at least 98%, in relation to the nucleic acid sequence mentioned in the previous paragraph.

We further provide an artificial or recombinant, i.e., produced by gene technology, expression vector, i.e., a vehicle for transfer of at least one nucleic acid to a recipient or host cell for expression of at least one protein or peptide encoded by the at least one nucleic acid, in the context of gene expression.

The expression vector includes at least one nucleic acid. However, it can be preferred that the expression vector does not include a nucleic acid, including or composed of a sequence according to SEQ ID No. 62 or a sequence homologous thereto.

As an alternative, the expression vector can include a gene cluster or operon or an integrative element.

The expression vector can, in principle, be a plasmid or a cosmid. Preferred is a plasmid or cosmid which can integrate into the chromosome of actinomycetes or is present as a replicative plasmid or cosmid in the cell and includes a corresponding constitutive or inducible (regulatable) promoter.

Preferably, the expression vector is a plasmid of the pRM family, in particular a plasmid of the pRM4 type, wherein the at least one nucleic acid or the gene cluster is inserted.

Particularly preferably, the expression vector includes a promoter without zinc repression (none-zinc-repressed promoter), i.e., a promoter not subject to zinc regulation.

The promoter can in principle be a constitutive or inducible (regulatable) promoter. Preferably the promoter is a strong constitutively expressed or inducible promoter which replaces an intracellular Zur target promoter. In this case, expression of nucleic acids or gene clusters is with particular advantage under the control of a zinc-independent promoter. The promoter in particular does not have a binding site for a protein according to SEQ ID No. 61. A preferred promoter without zinc repression is, for example, the promoter ermE (promoter of erythromycin resistance gene, PermE).

Preferably, the expression vector includes a nucleic acid, wherein the nucleic acid includes or is composed of a nucleic acid sequence selected from the group consisting of SEQ ID No. 40, SEQ ID No. 42, SEQ ID No. 44, SEQ ID No. 46, SEQ ID No. 48, SEQ ID No. 50, SEQ ID No. 52, SEQ ID No. 54, and combinations thereof.

Particularly preferred nucleic acid sequences may be selected from the group consisting of SEQ ID No. 48, SEQ ID No. 50, SEQ ID No. 52, SEQ ID No. 54, and combinations thereof.

The expression vector is suited to perform both homologous expression and heterologous expression.

As to further features and advantages of the expression vector, in particular of the nucleic acids and the gene cluster and operon, reference is made to the above description in its entirety.

We provide an artificial or recombinant, i.e., produced by biotechnology, host cell.

The host cell is preferably a [S,S]-EDDS producing host cell.

The host cell is characterized in that it includes at least one of the nucleic acids. As an alternative or in combination, the host cell is further characterized in that it includes at least one of the proteins or peptides.

As an alternative or in combination, the host cell is further characterized in that it includes a gene cluster or operon.

As an alternative or in combination, the host cell is further characterized in that it includes an expression vector. As an alternative or in combination, the host cell can include a genome which is present in a modified form owing to an at least partial, in particular complete, insertion of the vector (or vector genome).

In view of a biosynthesis of [S,S]-EDDS, it is preferred that zinc repression is not allowed within the host cell.

Particularly preferred is that the host cell does not include any nucleic acid encoding for a Zur protein, in particular no nucleic acid according to nucleic acid sequence SEQ ID No. 62 or a nucleic acid homologous thereto, and/or no Zur protein, in particular no protein or peptide according to amino acid sequence SEQ ID No. 61, or a protein or peptide homologous thereto.

The host cell can in principle be a eukaryote or prokaryote cell.

Furthermore, the host cell can be a homologous or heterologous host cell.

The host cell can in particular be selected from the group consisting of bacterial cell, yeast cell, and fungal cell.

The host cell may be a gram-positive bacterium, preferably a bacterium of the genus *Amycolatopsis* or *Streptomyces*, particularly preferred a bacterium of the species *Amycolatopsis japonicum* or *Streptomyces coelicolor*.

The host cell can be produced or be producible by transformation, transduction, transfection or conjugation, in particular using an expression vector.

The techniques for introduction of (foreign) nucleic acids, as mentioned in the previous paragraph, in particular of DNA and RNA, into eukaryote and prokaryote cells are basically well-known to those skilled in the art. These are standard procedures of molecular genetics. For a detailed description reference be made to relevant technical literature (e.g., Mülhardt C., Der Experimentator: Molekularbiologie/ Genomics (2008); Spektrum Verlag, 6. Ed.; or Kieser T. et al., Practical *Streptomyces* Genetics (2000); John Innes Foundation; or Green and Sambrook, Molecular Cloning: A Laboratory Manual (2012); Cold Spring Harbor Laboratory, 4. Ed.).

As to further features and advantages of the host cell, in particular the nucleic acids, the gene cluster and operon, the proteins or peptides, and the expression vectors, reference is made to the above description in its entirety.

We yet further provide an artificial or recombinant, i.e., produced by biotechnology, and preferably [S,S]-EDDS producing bacterial cell, preferably of the genus *Amycolatopsis*, in particular of the species *Amycolatopsis japonicum*.

The bacterial cell is characterized in that it does not express any protein or peptide, including or composed of an amino acid sequence according to SEQ ID No. 61, and/or does not include any nucleic acid, including or composed of a nucleic acid sequence according to SEQ ID No. 62.

The bacterial cell can be produced or be producible by an at least partial, preferably complete, deletion of a nucleic acid, including or composed of a nucleic acid sequence according to SEQ ID No. 62, from the genome, in particular wild-type genome, of the bacterial cell. Therein, the deletion can be the result of a transformation, transduction, transfection or conjugation. In other words, the bacterial cell can preferably be a deletion mutant. As an alternative to the deletion mentioned in this paragraph, even an exchange of a base pair, a point mutation and/or inactivation by insertion is conceivable.

Similarly, the bacterial cell can be produced or be producible by insertion of a nucleic acid, for example, in the form of a plasmid or a gene cassette, including or composed of a nucleic acid sequence according to SEQ ID No. 62, into the genome, in particular wild-type genome, of the bacterial cell.

As to further features and advantages of the bacterial cell, in particular the nucleic acid mentioned in the previous paragraphs, and the protein or peptide mentioned in the previous paragraphs, reference is made to the above description in its entirety.

We still further provide an artificial or recombinant, i.e., produced by gene technology, vector for producing a deletion of a nucleic acid (deletion vector) from a genome, in particular wild-type genome, of a bacterial cell of the genus *Amycolatopsis*, in particular of *Amycolatopsis japonicum*, wherein the nucleic acid to be deleted includes or is composed of a nucleic acid sequence according to SEQ ID No. 62.

The vector is characterized in that it includes at least one nucleic acid sequence located upstream in the genome of the bacterial cell in relation to the nucleic acid sequence according to SEQ ID No. 62, and/or at least one nucleic acid sequence located downstream in the genome of the bacterial cell in relation to the nucleic acid sequence according to SEQ ID No. 62, but not including the nucleic acid sequence according to SEQ ID No. 62.

Preferably, the at least one nucleic acid sequence located upstream and/or the at least one nucleic acid sequence located downstream are (each) a sequence immediately adjacent to the nucleic acid sequence according to SEQ ID No. 62 to be deleted. Preferably, the at least one nucleic acid sequence located downstream is a sequence according to SEQ ID No. 63, whereas the at least one nucleic acid sequence located upstream preferably is a sequence according to SEQ ID No. 64.

As to the at least one nucleic acid sequence located upstream and/or the at least one nucleic acid sequence located downstream it is further preferred that the sequences (each) comprise at least 300, preferably at least 500, in particular at least 1000, most preferably at least 1500 nucleotides.

Deletion of the nucleic acid sequence according to SEQ ID No. 62 results in the particular advantage that the biosynthesis of [S,S]-EDDS occurs independent of zinc since the repression protein Zur capable of binding zinc can no longer be expressed.

As to further features and advantages of the deletion vector, reference is made to the above description in its entirety.

We also provide a method for the biosynthesis of [S,S]-EDDS, comprising the steps:
  a) cultivation of a host cell and/or bacterial cell producing [S,S]-EDDS, and
  b) purification of [S,S]-EDDS from the cell and/or a culture medium used for the cell.

Preferably, the bacterial cell is produced by introducing a deletion vector into the bacterial cell, in particular a wild-type of the bacterial cell. The introduction of the vector can be performed by transformation, transduction, transfection or conjugation.

The host cell is produced according to another example by introducing an expression vector into the cell.

Preferably the host cell is produced in that an expression vector is introduced into a bacterial cell of the genus *Amycolatopsis*, in particular the species *Amycolatopsis japonicum*.

Alternatively, the host cell is produced in that an expression vector is introduced into a bacterial cell of the genus *Streptomyces*, in particular the species *Streptomyces coelicolor*.

Cultivation of the cells employed within the scope of the method can be performed using standard protocols well-known to those skilled in the art.

Contingent on the host cell or bacterial cell employed, it can be advantageous to culture the host cell or bacterial cell under zinc-free, in particular zinc salt-free conditions.

At least one precursor compound for the biosynthesis of [S,S]-EDDS can be added to a culture medium intended for culturing. Examples for appropriate precursor compounds can in principle be proteinogenic and/or non-proteinogenic amino acids. Appropriate precursor compounds can in particular be selected from the group consisting of L-ornithine, L-serine, L-proline, 2,3-diaminopropionic acid, L-aspartic acid, L-lysine, and combinations thereof.

Prior to purification of [S,S]-EDDS, an initial concentration determination of the produced [S,S]-EDDS may be performed. For example, high performance liquid chromatography (HPLC), UV/VIS spectroscopy or a combination of both techniques may be employed for that purpose.

For further purification of [S,S]-EDDS, a separator step for separating solid (cell) constituents can be performed. An isolation of [S,S]-EDDS using ion exchange adsorption with subsequent precipitation crystallization can follow thereafter.

Such methods are well-known. For purification, it is basically irrelevant if the [S,S]-EDDS is intracellular and needs to be made available by cell lysis, for example, or if it is secreted from the export system into the supernatant.

As to further features and advantages of the method, in particular the nucleic acids, the gene cluster and operon, the proteins or peptides, and the vectors, in particular deletion and expression vectors, reference is made to the above description in its entirety.

We further provide a kit for the biosynthesis of [S,S]-EDDS, comprising at least one component selected from the group consisting of at least one protein or peptide, at least one nucleic acid, a gene cluster or operon, a vector (expression and/or deletion vector), a host cell, a bacterial cell, and combinations thereof.

As required, the kit can comprise a further component selected from the group consisting of culture medium, buffer, and combinations thereof.

As to further features and advantages of the kit, in particular the nucleic acids, the gene cluster and operon, the proteins or peptides, and the vectors, in particular deletion and expression vectors, reference is also made to the above description in its entirety.

Further features and advantages will become apparent from the examples given below in connection with the figures. In particular, this disclosure is explained in more detail by description of the identification and annotation of the [S,S]-EDDS biosynthesis gene cluster. In the examples, individual features can be implemented as one or more in sub-combinations with other features.

EXAMPLES

1. Elucidation of the [S,S]-EDDS Biosynthesis

The genome of the [S,S]-EDDS producing bacteria species *A. japonicum* was sequenced. The genome of *A. japonicum* comprises approximately 9.18 MB and includes 8674 predicted open reading frames (orf). According to the Webtool Antibiotics and Secondary Metabolite Analysis Shell (antiSMASH) for rapid identification, annotation and analysis of the biosynthesis gene clusters for secondary metabolites (Medema et al, 2011, Nucleic Acids Res (2011); 39:14; and Blin et al., Nucleic Acids Res (2013); 1-9), the genome of *A. japonicum* includes 26 individual gene clusters for secondary metabolites. The clusters hold the biosynthetic potential for production of secondary metabolites derived from six NRPS (non-ribosomal peptide synthetases), six Type I PKS (polyketide synthase), two Type I PKS/NRPS hybrids and one Type III PKS/NRPS hybrid (for producing a glycopeptide) together with four terpenes, an ectoine, an aminoglycoside, and an L-antibiotic.

Initially, a putative biosynthesis pathway of [S,S]-EDDS was postulated (FIG. 1), wherein the aproteinogenic amino acid 2,3-L-diaminopropionate (Dap) may be a putative precursor of [S,S]-EDDS. Dap is, inter alia, a secondary metabolite in the biosynthesis of viomycin, synthesized by *Streptomyces vinaceus*, and the biosynthesis of zwittermicin A synthesized by *Bacillus thuringiensis*. Both synthesis pathways are elucidated (Thomas et al., Antimicrobial Agents and Chemotherapy (2003); 47(9):2823-2830 and Zhao et al., FEBS Lett (2008); 528(20):3125-3131).

Figure 1B:
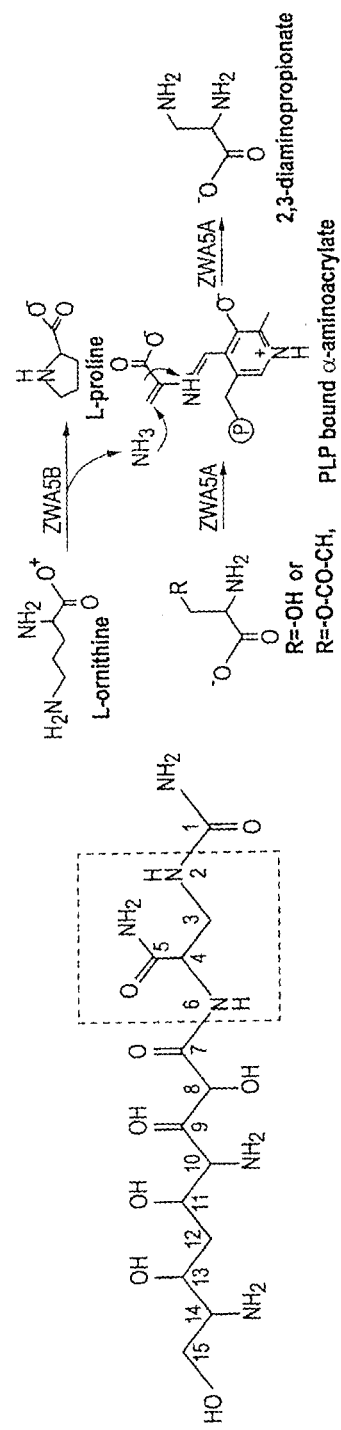

In *B. thuringiensis* and in *S. vinaceus* it was shown that Dap is specifically supplied for the biosynthesis of zwittermicin A and viomycin, respectively. Dap is produced both by the conversion of L-serine with L-ornithine as aminodonor during zwittermicin A and viomycin biosynthesis (FIG. 1). This reaction is catalyzed by the concerted actions of a Dap synthase (VioB/ZWA5A) and an ornithine cyclodeaminase (VioK/ZWA5B), requiring pyridoxalphosphate (PLP)

as cofactor (Thomas et al., Antimicrobial Agents and Chemotherapy (2003); 47(9):2823-2830; and Zhao et al., FEBS Lett (2008); 528(20):3125-3131).

Screening of the *A. japonicum* genome using BLAST (Basic Local Alignment Search Tool, in the version valid on the filing date of the application) with amino acid sequences of VioB/ZWA5A and VioK/ZWA5B, respectively, revealed the presence of homologue proteins encoded by genes in close proximity to each other. Thus, the nucleic acid according to SEQ ID No. 52 encodes for a protein of 352 aa in size and shows 32/45%, 26/44% aa identity/similarity to VioK and ZWA5B, respectively. SEQ ID No. 48 encodes for a protein of 327 aa in size and shows 25/39%, 21/40% aa identity/similarity to VioK and ZWA5B, respectively. The intermediate SEQ ID No. 50 is annotated as diaminopimelate decarboxylase and SEQ ID No. 54 as multidrug efflux transporter. SEQ ID No. 48, SEQ ID No. 50, SEQ ID No. 52, and SEQ ID No. 54 exhibit an overlapping gene arrangement and are presumably encoded as a transcriptional unit (FIG. 2).

Figure 2B:
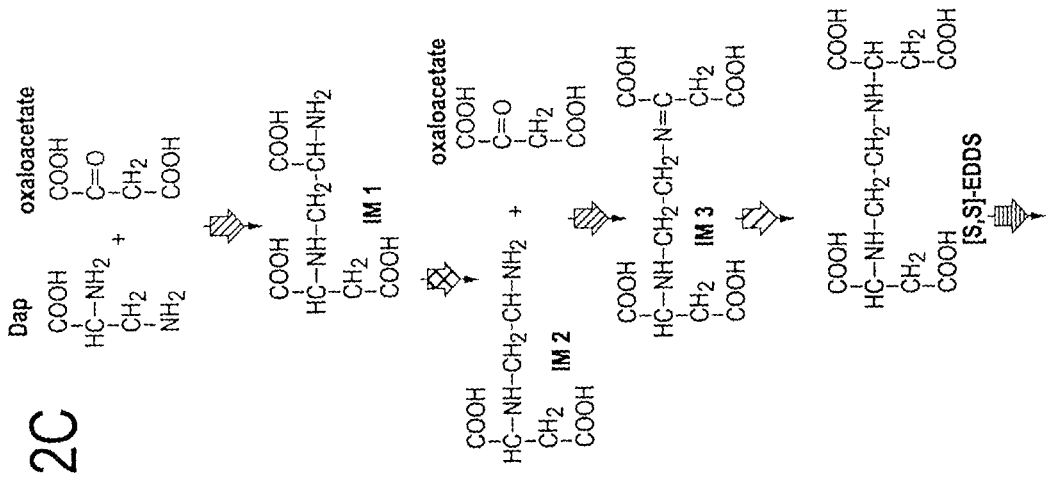
Figure 2C:
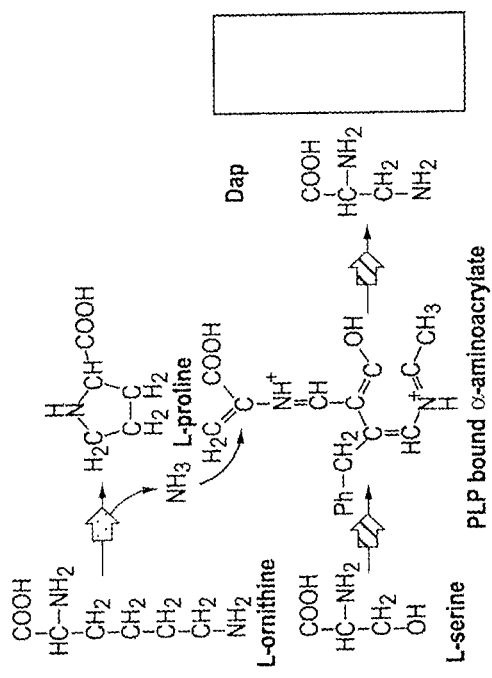

The proteins or peptides according to SEQ ID No. 39, SEQ ID No. 41, SEQ ID No. 43, and SEQ ID No. 45 are encoded 5' upstream of the above mentioned operon-like organized genes and are referred to as N-acetyltransferase, cysteine dioxygenase, HTH-type transcriptional regulator and amidase, respectively (FIG. 2).

Based on the above determined homologies the following assumptions are made:

The proteins or peptides according to SEQ ID No. 47 and SEQ ID No. 51 concertedly catalyze the synthesis of the precursor Dap as a first step of [S,S]-EDDS biosynthesis (FIG. 2).

The condensation of Dap with oxaloacetic acid to intermediate compound IM 1 is catalyzed by a protein or peptide according to SEQ ID No. 39 (nucleic acid according to SEQ ID No. 40; annotated as N-acetyltransferase).

The subsequent decarboxylation is catalyzed by a protein or peptide according to SEQ ID No. 49 (SEQ ID No. 48: referred to as diaminopimelate decarboxylase).

The repeated acetylation with oxalacetate again by a protein or peptide according to SEQ ID No. 39.

The final reduction is catalyzed by a protein or peptide according to SEQ ID No. 41 (SEQ ID No. 42: referred to as cysteine dioxygenase).

For the purpose of excretion, [S,S]-EDDS further has to be translocated across the cell membrane. This export may be mediated by the putative multidrug-efflux transporter according to SEQ ID No. 53 (FIG. 2).

Figure 3:
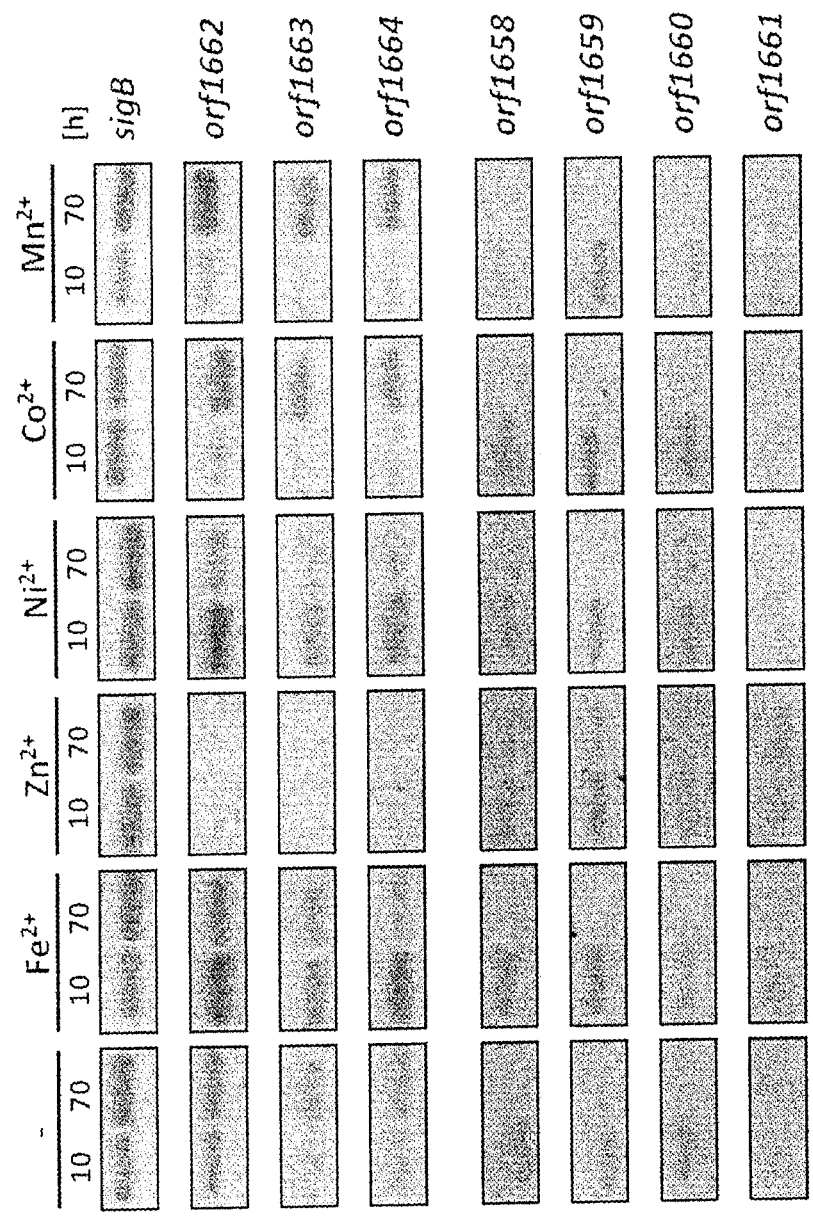
FIG. 3 shows a trace metal dependent transcriptional pattern of the [S,S]-EDDS biosynthesis gene cluster in *A. japonicum* obtained using RT-PCR. As housekeeping gene sigB was used to normalize the RNA. RNAs were prepared from cultures grown in defined medium in absence of any trace elements (−) or supplemented with 25 μM $Fe^{2+}$, $Zn^{2+}$, $Ni^{2+}$, $Co^{2+}$ or $Mn^{2+}$, respectively. Samples were taken after 10 h and 70 h of incubation.

To demonstrate that the identified region is indeed responsible for [S,S]-EDDS biosynthesis, the zinc repression of the [S,S]-EDDS biosynthesis was considered. Since [S,S]-EDDS is produced exclusively under essentially zinc-free conditions (a zinc concentration as low as 2 µM causes an almost complete disruption of the [S,S]-EDDS synthesis (Cebulla I., Thesis (1995), University of Tubingen)), the transcription pattern of the putative biosynthesis genes was determined by RT-PCR (real time polymerase chain reaction), in respect of the presence of zinc and absence of zinc (FIG. 3).

The putative Dap-synthesis genes including the nucleic acid sequences according to SEQ ID No. 48 and SEQ ID No. 52, the intermediate sequence according to SEQ ID No. 50 and the sequence according to SEQ ID No. 54 are expressed exclusively during growth in the absence of zinc ([S,S]-EDDS production), however, not in the presence of zinc. There was no repression of these genes by other divalent metal ions found. The nucleic acids according to SEQ ID No. 40, SEQ ID No. 42, SEQ ID No. 44, and SEQ ID No. 46 show a common transcriptional pattern, not affected by zinc (FIG. 3).

The thus identified operon of the putative [S,S]-EDDS biosynthesis (SEQ ID No. 48, 50, 52, and 54) exhibits a zinc-dependent transcription.

To evidence an involvement of the genes according to SEQ ID No. 48, 50, and 52 severely affected by zinc in the synthesis of [S,S]-EDDS, an in-frame deletion mutant of the coding regions SEQ ID No. 48, 50, and 52 was further generated.

A total of 12 *A. japonicum* mutants (*A. japonicum* ΔSEQ ID No. 48, 50, and 52) with an in-frame deletion of the coding regions of SEQ ID No. 48, 50, and 52 were generated. *A. japonicum* wild-type (*A. japonicum* WT) and all generated mutants were grown in EDDS-production media (cf. Table 1).

TABLE 1

| M7 medium (EDDS production medium) | 11.3 g sodium glutamate<br>8.0 g potassium hydrogen phosphate<br>12.0 g disodium hydrogen phosphate<br>1 ml anti-foaming agent<br>25.0 g glycerol<br>1.2 magnesium sulfate<br>60 mg iron(III) citrate |
|---|---|
| M3 medium | 20.0 g glycerol<br>20.0 g soy meal<br>pH 7.5 |
| M2 medium | 50.0 g sodium glutamate<br>50.0 g saccharose<br>50.0 g dextran<br>pH 7.2 |
| TSB medium (Bacto ® Tryptic Soy Broth Soybean-Casein Digest Medium; Becton, Dickinson, Co.) | 30.0 g TSB powder |
| EMSA binding buffer | 80 mM Tris/HCl (pH 7.8)<br>200 mM KCl<br>20% glycerol |

Figure 4:
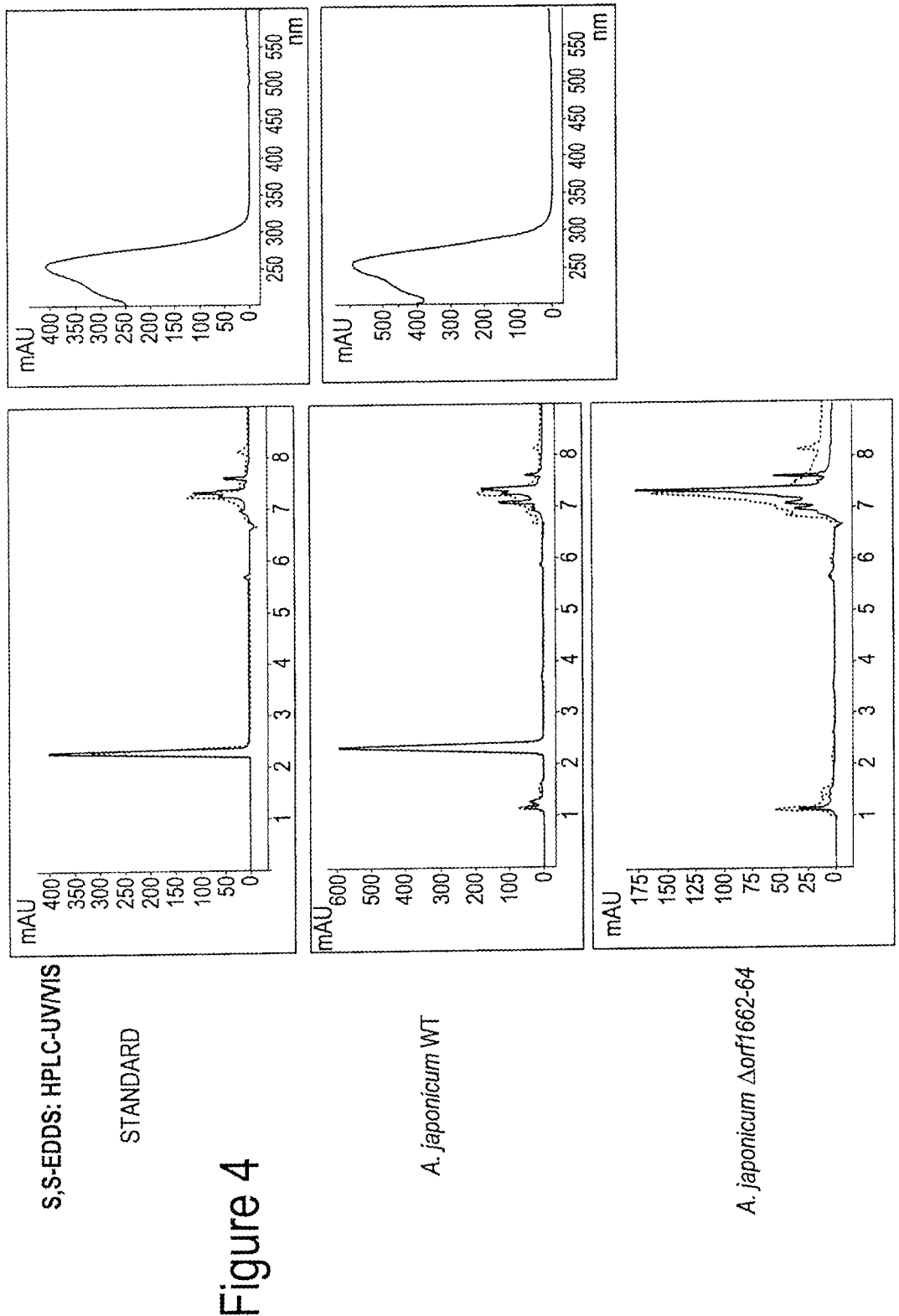
FIG. 4 shows a HPLC-UV/VIS analysis of the supernatants of *A. japonicum* WT (wild-type) and a mutant *A. japonicum* Δorf1662-64 after growth in M7 medium for 72 h. (Top) [S,S]-EDDS standard [350 mg/L]. (Middle) *A. japonicum* WT. (Bottom) *A. japonicum* Δorf1662-64. (Right) Specific UV/VIS spectra of [S,S]-EDDS.

While the *A. japonicum* WT strain produces [S,S]-EDDS under the chosen conditions, none of the 12 mutants was able to synthesize [S,S]-EDDS, anymore (FIG. 4).

What could be demonstrated is that the operon structure including or composed of a nucleic acid sequence according to SEQ ID No. 48, 50, and 52 is required for the [S,S]-EDDS biosynthesis in *A. japonicum*.

To demonstrate, that the identified gene cluster contains all required genetic information for the [S,S]-EDDS biosynthesis, a cosmid comprising the entire gene cluster was expressed heterologously in *S. coelicolor*. This cosmid (pTWPL1-EDDS) contains the genes according to SEQ ID No. 4, 6, 8, 10, 12, 14, 16, 18, 20, 22, 24, 26, 28, 30, 32, 34, 36, 38, 40, 42, 44, 46, 48, 50, 52, 54, 56 and 58, and parts according to SEQ ID No. 2 and SEQ ID No. 60 (Table 2).

TABLE 2

| Orf | SEQ ID No. | Annotated function |
|---|---|---|
| 1639 | 2 | 2-isopropylmalate synthase |
| 1640 | 4 | fumarylacetoacetate hydrolase family protein |
| 1641 | 6 | tRNA uridine 5-carboxymethylaminomethyl modification enzyme mnmG |
| 1642 | 8 | phosphoglycolate phosphatase |
| 1643 | 10 | hypothetical protein |

TABLE 2-continued

| Orf | SEQ ID No. | Annotated function |
|---|---|---|
| 1644 | 12 | hypothetical protein |
| 1645 | 14 | alcohol dehydrogenase superfamily, zinc-containing; L-threonine 3-dehydrogenase |
| 1646 | 16 | hypothetical protein |
| 1647 | 18 | transcriptional regulator, PadR-like family |
| 1648 | 20 | hypothetical protein |
| 1649 | 22 | major facilitator superfamily MFS_1 |
| 1650 | 24 | major facilitator superfamily MFS_1 |
| 1651 | 26 | transcription regulator HTH, ArsR |
| 1652 | 28 | bialaphos biosynthetic pathway regulatory protein |
| 1653 | 30 | furin (EC = 3.4.21.75) |
| 1654 | 32 | hypothetical protein |
| 1655 | 34 | helix-turn-helix type 3 |
| 1656 | 36 | hypothetical protein |
| 1657 | 38 | two component transcriptional regulator, LuxR family |
| 1658 | 40 | N-acetyltransferase |
| 1659 | 42 | cysteine dioxygenase |
| 1660 | 44 | HTH-type transcriptional regulator |
| 1661 | 46 | Amidase |
| 1662 | 48 | ornithine cyclodeaminase |
| 1663 | 50 | diaminopimelate decarboxylase |
| 1664 | 52 | cystathionine beta-synthase |
| 1665 | 54 | transporter protein |
| 1666 | 56 | sporulation proteins |
| 1667 | 58 | ferric uptake regulation protein |
| 1668 | 60 | catalase/peroxidase [until nt 1512] |

Figure 5:
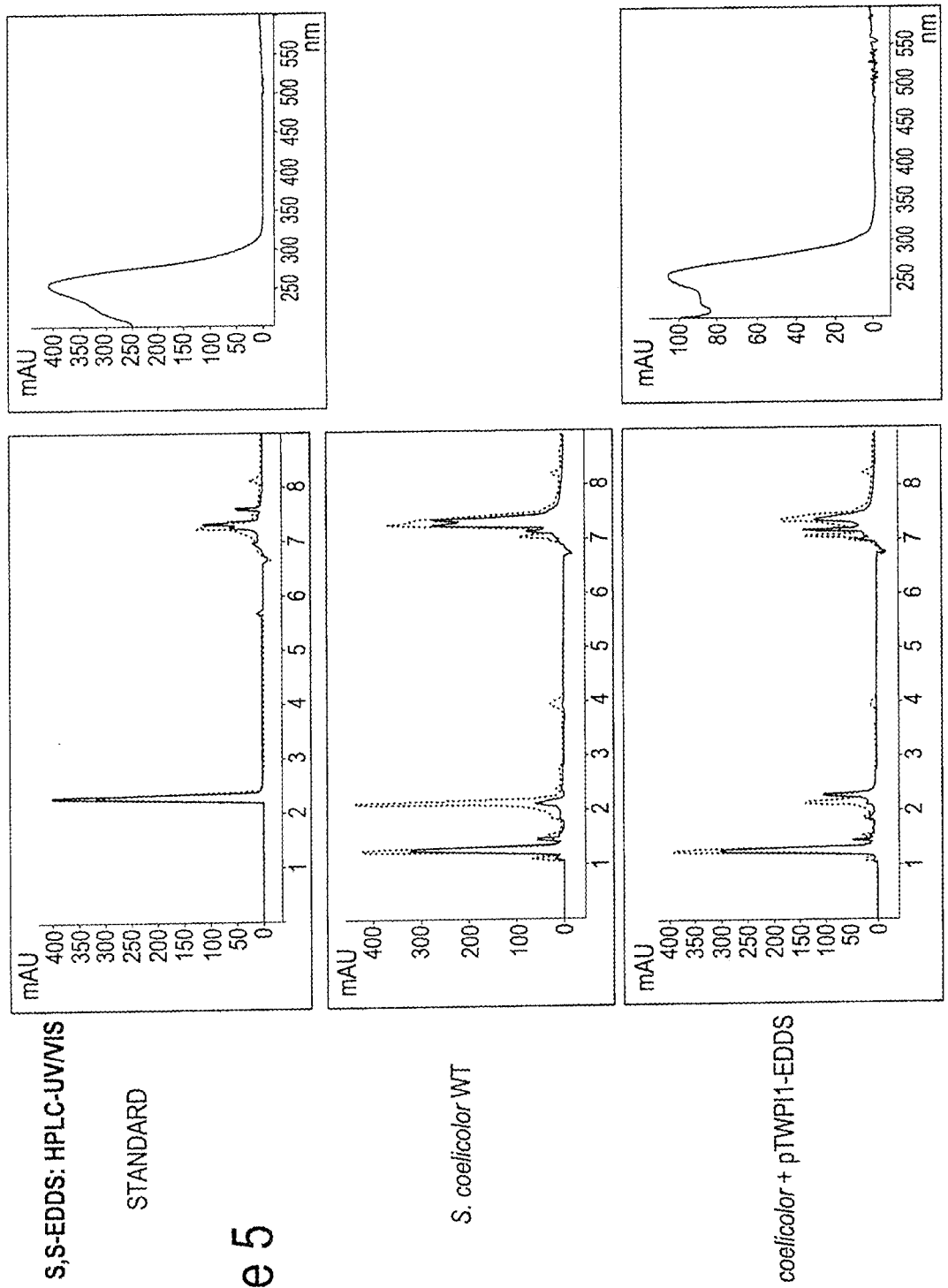
FIG. 5 shows a HPLC-UV/VIS analysis of the supernatants of *S. coelicolor* WT and *S. coelicolor*-pTWPL1-EDDS after growth in M7 medium for 72 h. (Top) [S,S]-EDDS standard [350 mg/L]. (Middle) *S. coelicolor* WT (Bottom) *S. coelicolor*-pTWPL1-EDDS. (Right) Specific UV/VIS spectra of [S,S]-EDDS.

The *S. coelicolor* wild-type strain (*S. coelicolor* WT) and the *S. coelicolor* strain with genome integrated cosmid pTWPL1-EDDS (*S. coelicolor* pTWPL1-EDDS) was grown in EDDS production media. While the *S. coelicolor* WT strain is not able to produce [S,S]-EDDS under the chosen conditions, *S. coelicolor*-pTWPL1-EDDS produces detectable amounts of [S,S]-EDDS in zinc-free EDDS production media (FIG. 5).

The production of [S,S]-EDDS by *S. coelicolor*-pTWPL1-EDDS demonstrates that all enzymes required for the [S,S]-EDDS biosynthesis are encoded in the gene region orf1640-1667 or SEQ ID No. 4, 6, 8, 10, 12, 14, 16, 18, 20, 22, 24, 26, 28, 30, 32, 34, 36, 38, 40, 42, 44, 46, 48, 50, 52, 54, 56 and 58.

2. Elucidation of the Zinc Repression of the [S,S]-EDDS Biosynthesis

The Fur (Ferric uptake regulator) family of global metalloregulatory proteins is named for the Ferric Uptake Regulator (Fur) of *E. coli* (Hantke K., Mol Gen Genet (1981); 182(2):288-292 and Bagg & Neilands, Biochemistry (1987); 26:5471-5477). Besides the iron-selective Fur, there is a great diversity in metal selectivity and biological function within the Fur family. Among them sensors of zinc (Zur), manganese (Mur) and nickel (Nur), for example.

Fur proteins are typically transcriptional repressors binding to corresponding operator DNA sequences when bound to their cognate metal ion effectors (iron-bonded Fur referred to as holoFur protein, for example), hindering the access of RNA polymerase which results in a repression of downstream genes (Lee & Helmann, Nature (2006); 440 (7082):363-367). The metal-free proteins (apoFur protein, for example) generally possess low or negligible affinity for the respective operator sequence leading to a derepression of the target genes.

The ability of Fur family members to function physiologically as sensors of Zn(II) ions was discovered concurrently in low GC gram-positive *B. subtilis* ($Zur_{BS}$) and γ-proteobacteria *E. coli* ($Zur_{EC}$) (Gaballa & Helmann, J. Bacteriol. (1998); 180:5815-21; and Patzer & Hantke, Mol Microbiol (1998); 28:1199-1210). Subsequently, genomic analyses have allowed tentative assignments of likely Zur regulons in numerous other bacteria, revealing the spread of Zur mediated zinc uptake regulation in bacteria kingdom (Panina et al., Proc Natl Acad Sci USA (2003 Aug. 19); 100(17):9912-7). In the meantime, a multiplicity of Zur proteins have been biochemically characterized besides $Zur_{BS}$ and $Zur_{EC}$ such as from gram-negative *Yersinia pestis* ($Zur_{YP}$), *Salmonella enterica* ($Zur_{SE}$) and *Xanthomonas campestris* ($Zur_{XC}$), low GC gram-positive firmicutes *Staphylococcus aureus* ($Zur_{SA}$), *Streptococcus suis* ($Zur_{SS}$) and *Listeria monocytogenes* ($Zur_{LM}$) and high GC gram-positive actinobacteria *Mycobacterium tuberculosis* ($Zur_{MT}$), *Corynebacterium diphtheriae* ($Zur_{CD}$), *Corynebacterium glutamicum* ($Zur_{CG}$) and *S. coelicolor* ($Zur_{SC}$) (Li et al., BMC Microbiol. (2009 Jun. 25); 9:128; Feng et al., J Bacteriol. (2008); 190(22): 7567-78; Lindsay & Foster, Microbiology (2001), 147, 1259-66; Campoy et al., Infect. Immun. (2002); 70:4721-5; Garrido et al., FEMSMicrobiol. Lett. (2003); 221:31-37; Tang et al., Mol. Plant-Microbe Interact. (2005); 18:652-8; Maciag et al., J Bacteriol. (2007):189(3):730-40; Shin et al., Journal of Bacteriology (2007); June: 4070-7; Dalet et al., FEMS Microbiol. Lett (1999); 174:111-6; Schroder et al., BMC Genomics (2010); 11:12; and Smith et al., J Bacteriol. (2009); 191(5):1595-603).

A group of genes is referred to as regulon when their activity is controlled by the same regulator. Regulons under the control of Zur proteins include genes encoding for zinc acquisition functions such as high affinity zinc uptake systems (znuABC), putative zincophors and zinc-free paralogues of ribosomal proteins, for example. These genes are repressed by binding of the zinc-bound holoZur proteins under zinc-replete conditions and derepressed by dissociation of the zinc-free apoZur protein from the DNA.

*S. coelicolor*, a model organism of high GC actinomycetes, regulates metal homeostasis and peroxide stress response, inter alia, with four biochemically characterized proteins of the Fur family ($FurA_{SC}$, $CatR_{SC}$, $Nur_{SC}$ and $Zur_{SC}$) (Hahn et al., J Bacteriol. (2000); 182(13):3767-74; Ahn et al., Mol. Microbiol. (2006); 59:1848-58; and Shin et al., Journal of Bacteriology (2007); June: 4070-7).

BLAST analysis of *A. japonicum* with the aa sequences of the four distinct Fur family proteins of *S. coelicolor* revealed that the *A. japonicum* genome encodes three Fur family protein homologues, encoded corresponding to nucleic acid sequences orf1667 (corresponding to SEQ ID No. 58), orf3462 and orf5768 (corresponding to SEQ ID No. 62).

The Fur family homologues ORF1667 (corresponding to SEQ ID No. 57) and ORF3462 are highly similar to *S. coelicolor* $FurA_{SC}$ (62/75% and 67/79% aa identity/similarity). *S. coelicolor* $FurA_{SC}$ is involved in the adaptive response to peroxide stress and negatively regulates an operon including $furA_{SC}$ gene itself and catC, encoding a catalase-peroxidase (Hahn et al., J Biol Chem. (2000); 275(49):38254-60).

The third Fur family homologue protein including an amino acid sequence according to SEQ ID No. 61 is highly similar to *S. coelicolor* $Zur_{SC}$ and exhibits 67/85% aa identity/similarity (FIG. 6).

The high similarity of the biochemically characterized $Zur_{SC}$ of *S. coelicolor* and the *A. japonicum* homologue ($Zur_{AJ}$) encoded by a nucleic acid sequence according to SEQ ID No. 62 (or orf5768) implies that the protein or peptide according to SEQ ID No. 61 is the zinc-responsive Fur family protein of *A. japonicum* mediating zinc-dependent repression of corresponding target genes.

Figure 7A:
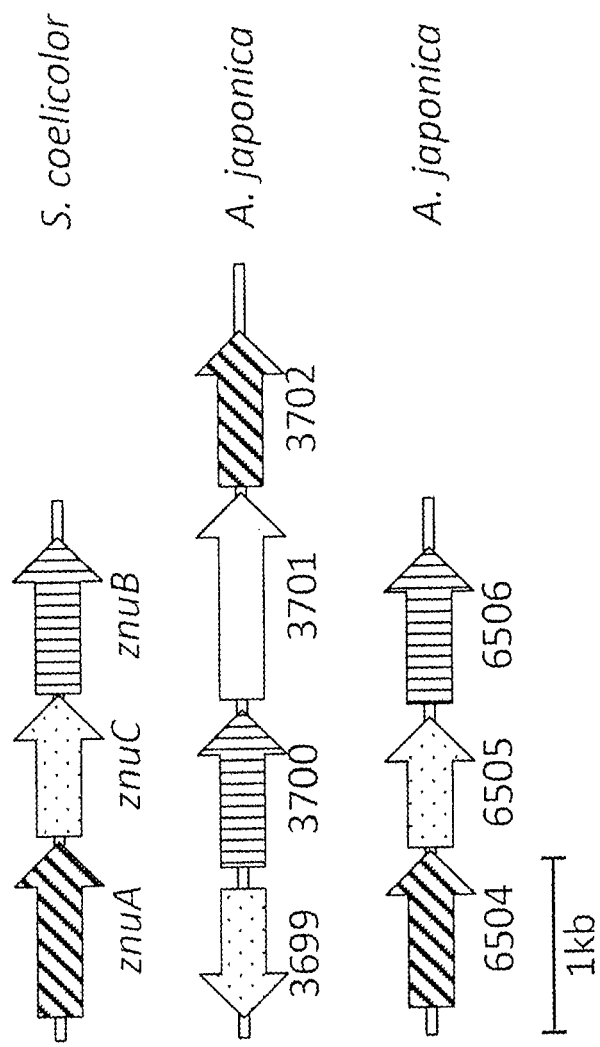

$Zur_{SC}$ is the negative regulator of the high affinity zinc uptake system (ZnuABC) in *S. coelicolor* (Shin et al., Journal of Bacteriology (2007); June: 4070-7). BLAST analysis of the *A. japonicum* genome with amino acid sequences of *S. coelicolor* ZnuABC revealed two homologue systems encoded by orf3699, orf3700 and orf3701 respectively orf6504, orf6505 and orf6506 (FIG. 7).

It is well-known that the expression of the znuABC operon of *S. coelicolor* is tightly repressed by $Zur_{SC}$ with zinc as cofactor (Shin et al., Journal of Bacteriology (2007); June: 4070-7). Hence, to confirm which of the two putative zinc uptake systems mediates high affinity zinc uptake in *A. japocinum*, the transcription of orf3700 and orf6504 as representatives for the entire systems was examined in dependence of the presence of zinc as well of various other metals (FIG. 8).

Figure 8:
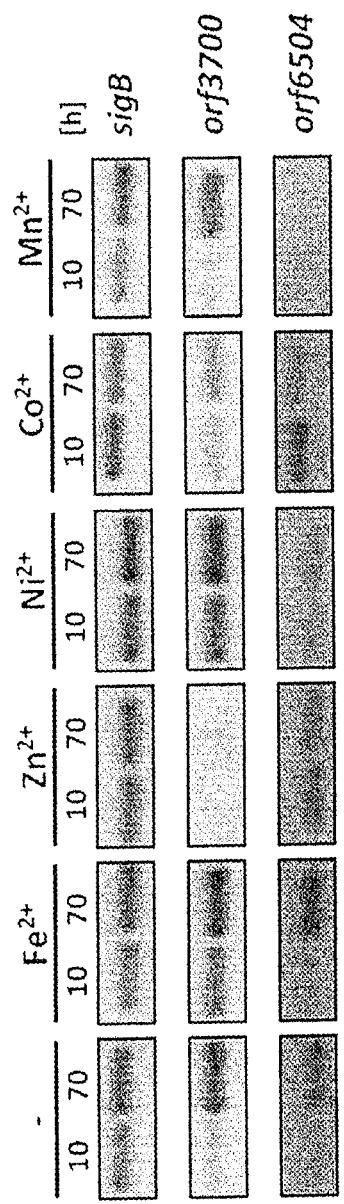
FIG. 8 shows a trace metal dependent transcriptional pattern of the metal uptake system of *A. japonicum* obtained using RT-PCR. As housekeeping gene sigB was used to normalize the RNA. RNAs were prepared from cultures grown in defined M7 medium in the absence of any trace elements (–) or supplemented with 25 µM $Fe^{2+}$, $Zn^{2+}$, $Ni^{2+}$, $Co^{2+}$ or $Mn^{2+}$ solutions, respectively. Samples were taken after 10 and 70 h of incubation. orf3700 and orf6504 were chosen as probes to represent the entire operon-like structures.

The DNA region orf3700 was expressed under metal starvation and in the presence of iron, nickel, cobalt and manganese, however, not in the presence of zinc (FIG. 8). This transcriptional pattern clearly showed the tight and exclusively zinc-mediated repression of orf3700 in *A. japonicum*. These results allow the conclusion that the uptake system encoded by orf3699, orf3700 and orf3702 represents the high affinity zinc uptake system (ZnuABC) of *A. japonicum*.

To confirm that the $Zur_{SC}$ homologue protein according to SEQ ID No. 61 (encoded by SEQ ID No. 62) is the zinc responsive Fur family protein of *A. japonicum* and mediates zinc-dependent repression of the zinc uptake system (znuABC) and of the putative [S,S]-EDDS biosynthesis genes, affinity electrophoretic assays (EMS Assays, Electrophoretic Mobility Shift Assays) were performed.

Figure 9:
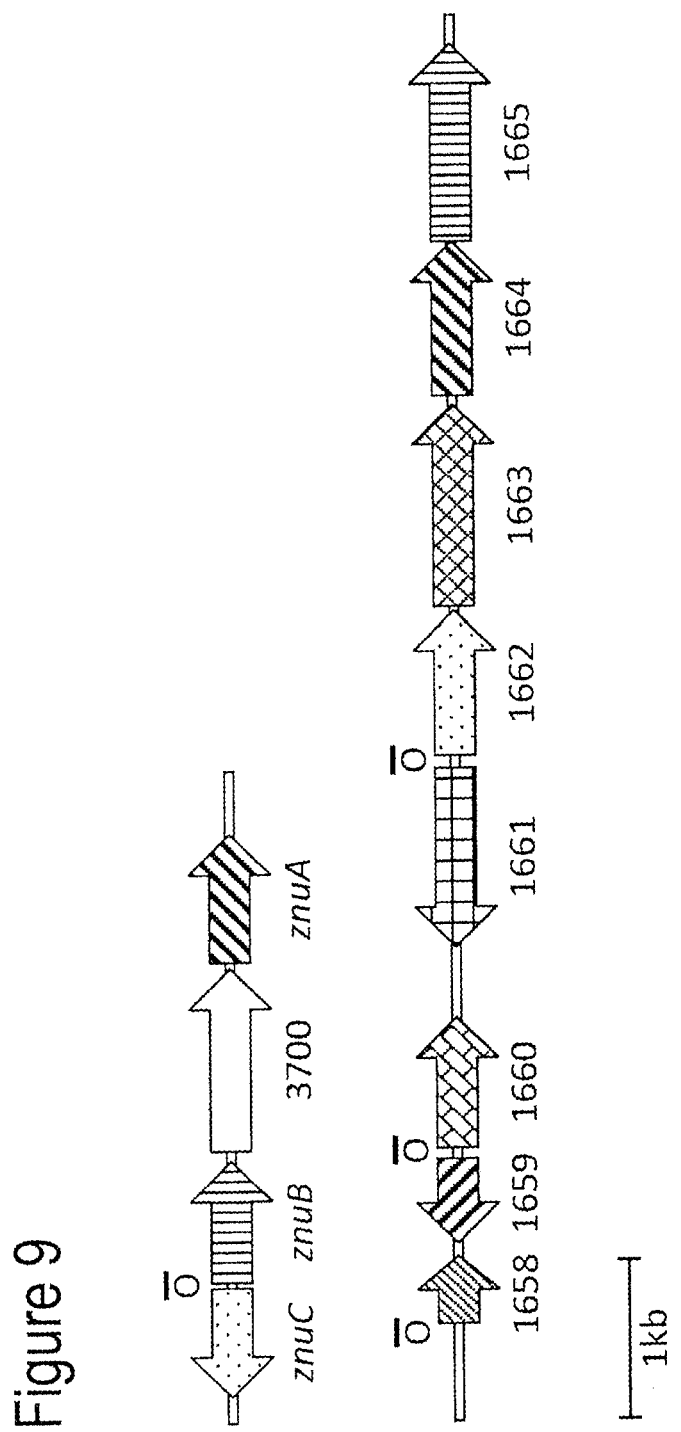
FIG. 9 shows schematic representations of the used EMSA-DNA probes. (Top) znuABC gene loci of *A. japonicum* (orf3699-orf3702). (Bottom) [S,S]-EDDS biosynthesis gene cluster orf1658-orf1665 (corresponding to SEQ ID No. 40, 42, 44, 46, 48, 50, 52, 54). Promoter regions including $Zur_{AJ}$ binding sites are marked with an open circle and EMSA probes, used to test His-ORF5768 binding, are illustrated by a black line.

Binding of the protein or peptide according to SEQ ID No. 61 was analyzed using the 5' upstream promoter region of the zinc-repressed genes orf3700 and orf1662 (corresponding to SEQ ID No. 46) and additionally all other predicted promoter regions within the putative [S,S]-EDDS biosynthesis gene cluster (upstream region of orf1658, intergenic region of orf1659 and orf1660, intergenic region of orf1661 and orf1662) in respect to zinc as cofactor (FIG. 9).

To confirm that the homologue zinc uptake regulator ORF5768 ($Zur_{AJ}$ corresponding to SEQ ID No. 61) mediates the zinc-dependent repression of orf3700, orf1662 and the other genes within the [S,S]-EDDS biosynthesis gene cluster by binding to corresponding promoter regions (open circles, FIG. 9), EMS Assays, (Electrophoretic Mobility Shift Assays) or also Band Shift Assays were performed. Therein, the homologue zinc uptake regulator ORF5768 was marked with a $Histidin_6$ tag, purified and isolated. Likewise provided were the corresponding DNA sequences (promoter sequences) to be analyzed for action as putative zinc regulated promoters (open circles, FIG. 9).

Figure 10A:
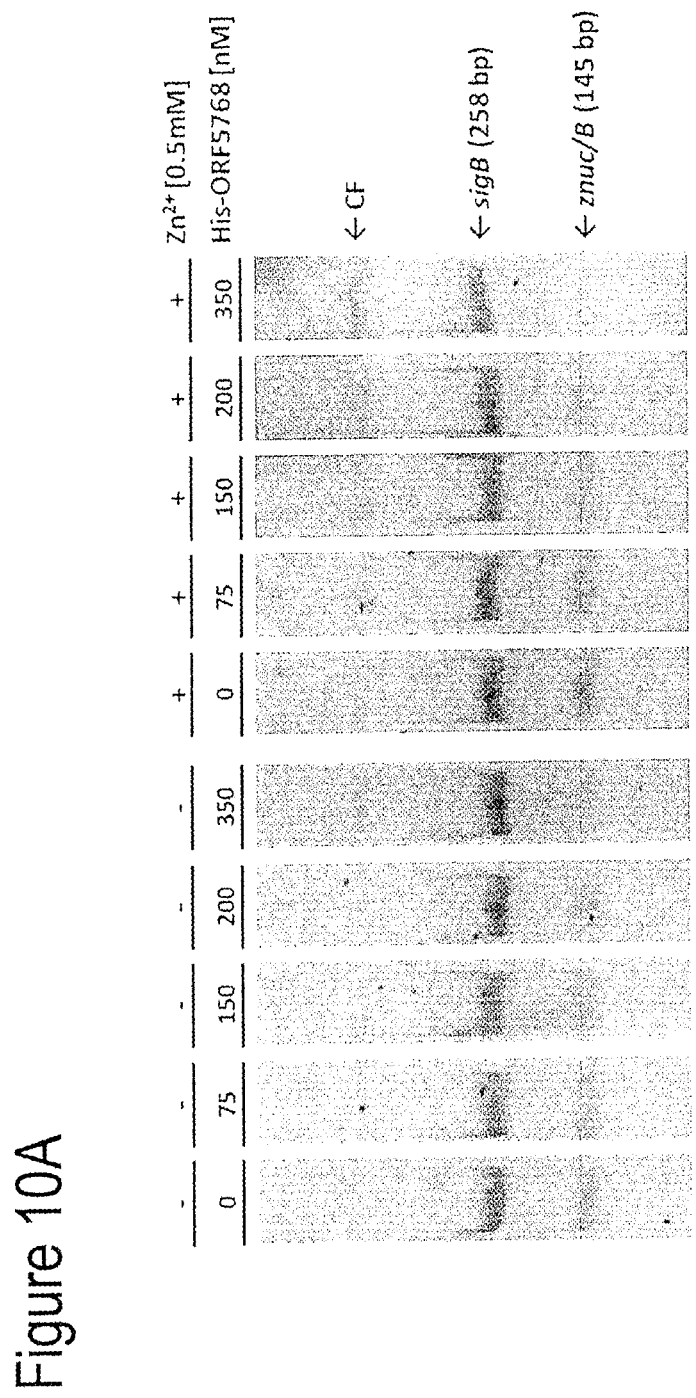
Figure 10C:
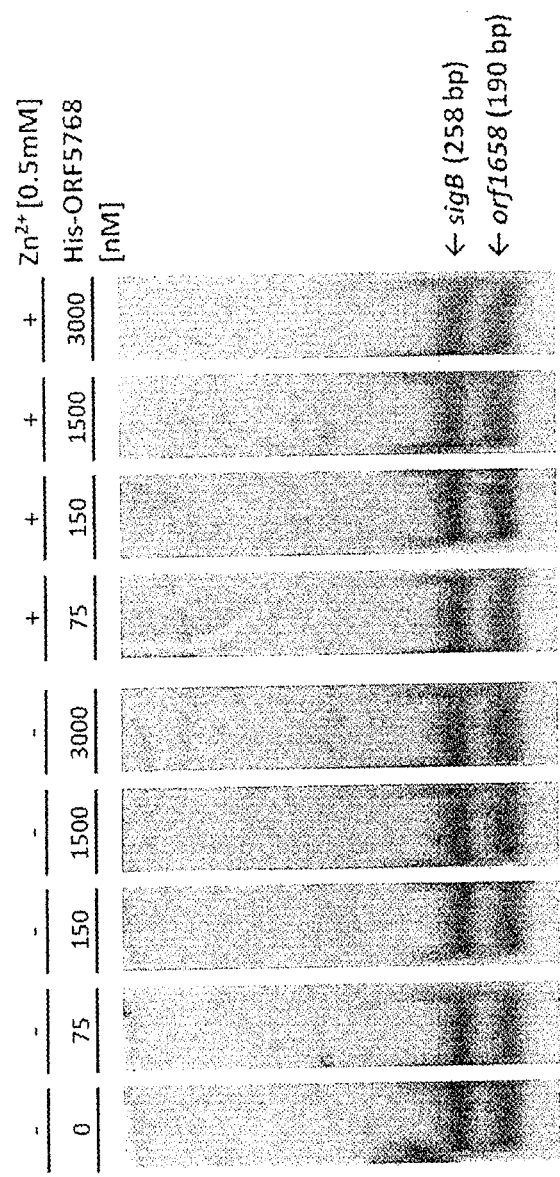
Figure 10D:
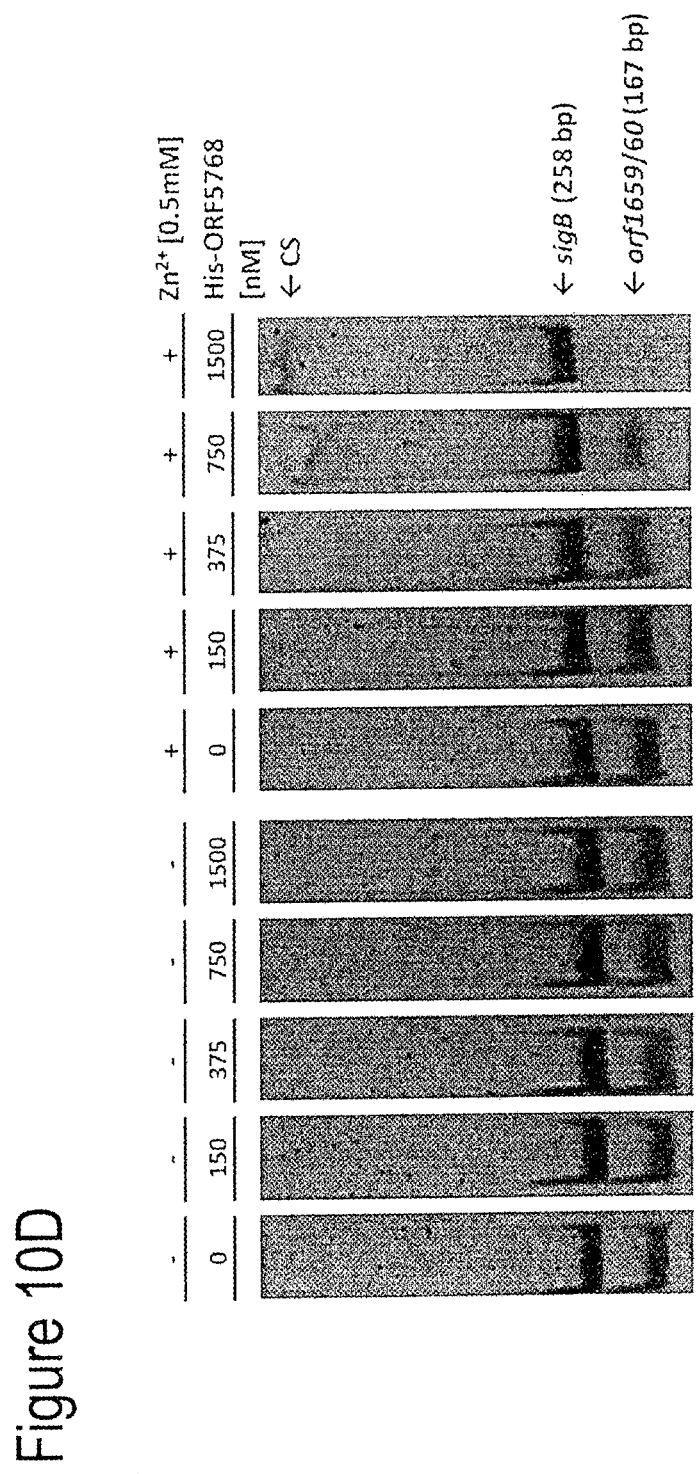

Binding reactions were performed in that the promoter sequences (about 35 nM) were incubated using different amounts of $His_6$-ORF5768 in 10 µl binding buffer (Table 1) for 20 min at 29° C. in the presence and absence of zinc. To exclude unspecific bindings of $His_6$-ORF5768, the addition of a sigB-RT fragment (258 bp) was used as a negative control (FIG. 10).

A zinc-dependent binding (i.e., in the presence of zinc) of $His_6$-ORF5768 to those EMSA-probes representing the znuABC promoter region and to the ones representing the orf1659-60 and orf1661-62 promoter regions could be demonstrated using EMSA. There was no binding detected to the orf1658 promoter region (FIG. 10).

3. Generation of a Zinc Derepressed [S,S]-EDDS Production Strain

To generate a zinc derepressed [S,S]-EDDS production strain of *A. japonicum*, three distinct strategies were pursued:

(1) Deletion of the zinc uptake regulator gene (and thus of the repression protein Zur) SEQ ID No. 62.
(2) Expression of the [S,S]-EDDS biosynthesis genes under the control of none-zinc-repressed promoters. Exchange of the Zur-targeted promoters.
(3) Heterologous expression of the [S,S]-EDDS biosynthesis genes in host cells in which the zinc repression no longer applies.

3.1 Deletion of the Zinc Uptake Regulator Gene SEQ ID No. 62

Suggesting that the [S,S]-EDDS biosynthesis genes are repressed by $Zur_{AJ}$ (ORF5768 and protein or peptide according to SEQ ID No. 61) with zinc as cofactor, deletion of the coding region according to SEQ ID No. 62 was performed to generate a zinc derepressed [S,S]-EDDS production strain.

Figure 11:
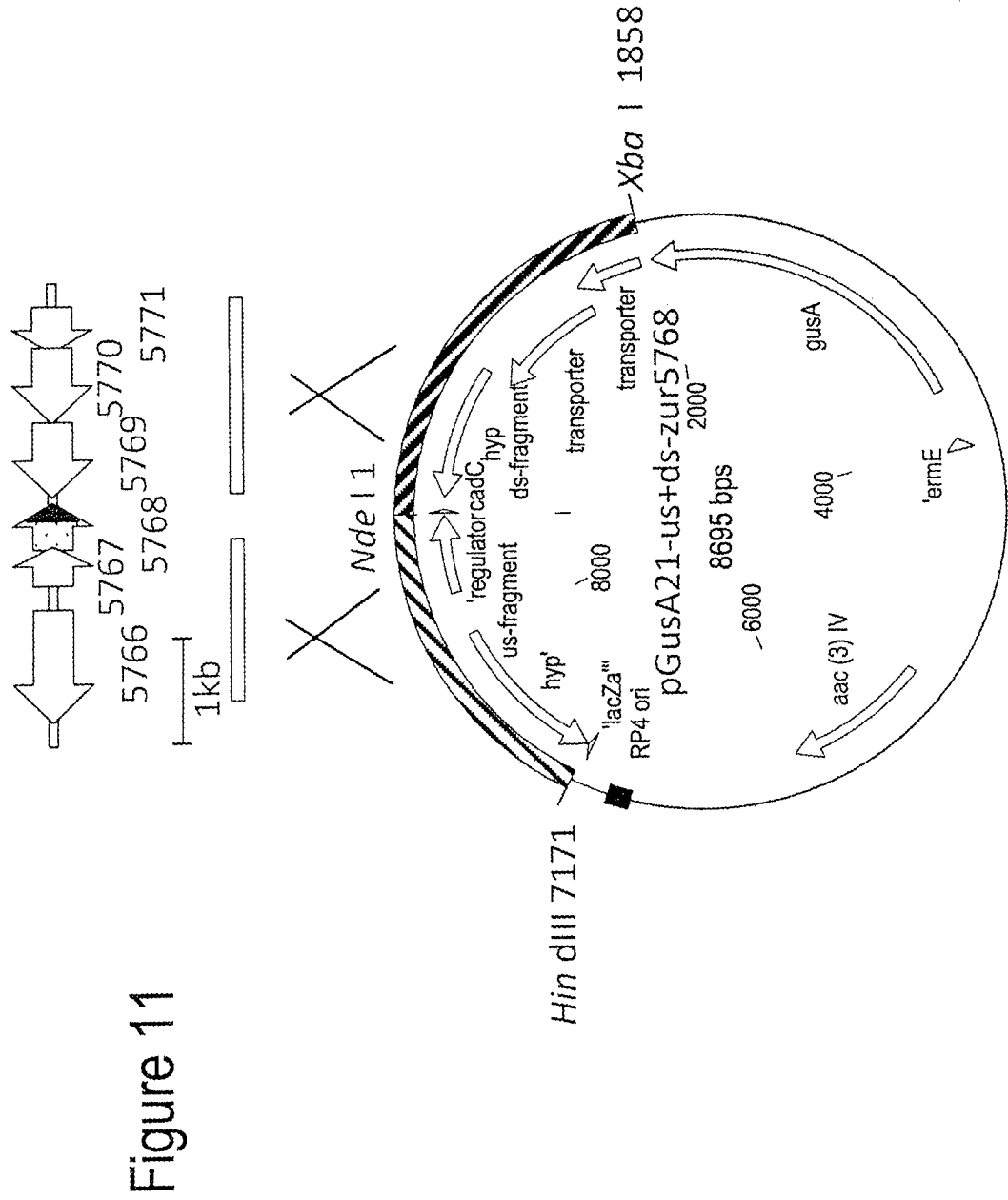
FIG. 11 shows a schematic representation of the deletion vector pGusA21Δorf5768. (Top) orf5768 (corresponding to SEQ ID No. 62) and surrounding genes. (Bottom) pGusA21Δorf5768. Left bar: 5' flanking region of orf5768; right bar: 3' flanking region of orf5768.

To achieve the in-frame deletion of the coding region according to SEQ ID No. 62 (corresponding to orf5768) via homologues recombination, the deletion vector pGusA21Δorf5768 was constructed containing the upstream and downstream regions of orf5768, which is similar to pGusA21-us1662+ds1664 (AG Stegmann). A non-methylated negative pGusA21Δorf5768 was obtained from *E. coli* ET12567 and used for direct transformation of *A. japonicum* (FIG. 11).

Apramycin-resistant colonies of *A. japonicum*, obtained after transformation using non-methylated pGusA21Δorf5768, were transferred to HA plates. Growing colonies were overlaid with X-Gluc (5-bromo-4-chloro-3-indolyl-ß-D-glucoronid) solution and blue colonies (FIGS. 12A and 12B, positive on reporter gene gusA: clone 1, 6, 7, 8, 12) were selected for a further examination by PCR for cases of single crossing-over.

Figure 12B:
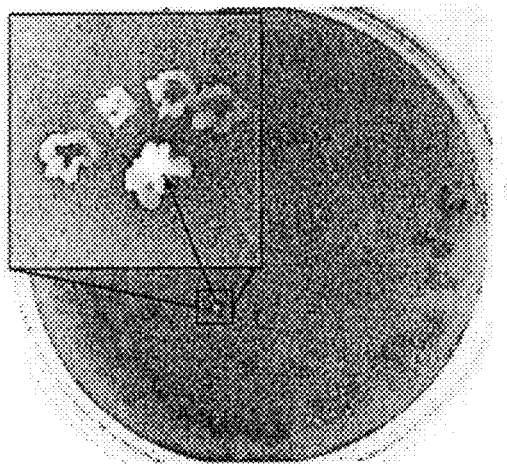
FIGS. 12A-12B show a verification of the integration of pGusA21Δorf5768 into the genome of *A. japonicum* after direct transformation. (A) PCR-based verification of the integration of pGusA21Δorf5768. Expected WT profile: 1677 bp (orf5768-SCO-wt-Frag); expected integrated pGusA21Δorf5768 profile: 1263 bp (orf5768-SCO-single-Frag). wt: wild-type gDNA template; P: isolated pGusA21Δorf5768 template. (B) Search for clones of *A. japonicum* with lost pGusA21Δorf5768 using the Gus reporter system. The genome of blue colonies includes the integrated pGusA21Δorf5768 plasmid, while non-stained colonies have lost it.
Figure 12A:
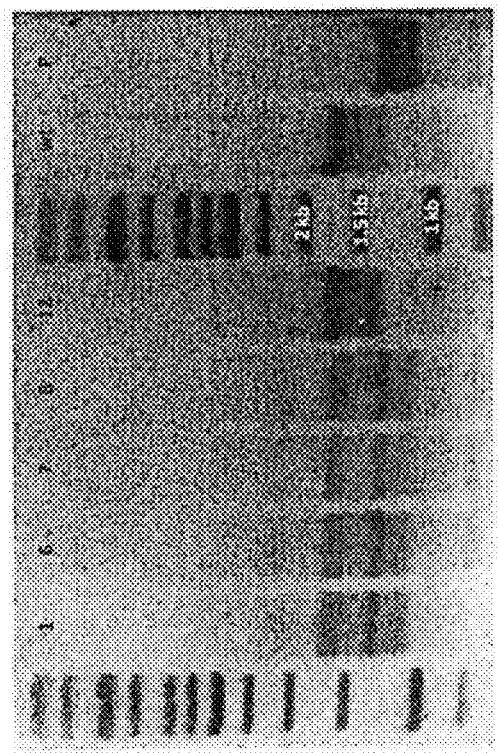
Figure 13D:
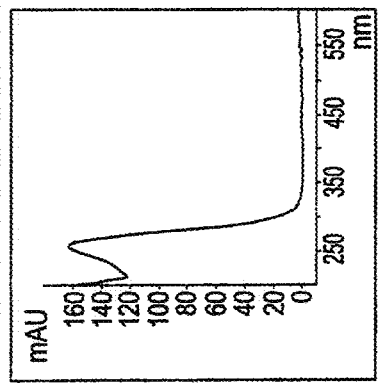
FIGS. 13A-13I show a HPLC-UV/VIS analysis of the supernatants of *A. japonicum* WT and *A. japonicum* Δzur (corresponding to ΔSEQ ID No. 62) after growth in M7 medium for 72 h with and without supplementation of 6 µM $ZnSO_4$.
Figure 13E:
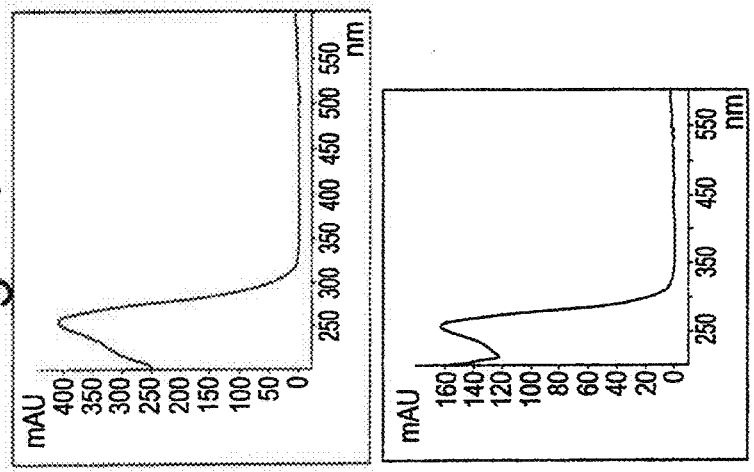
Figure 13A:
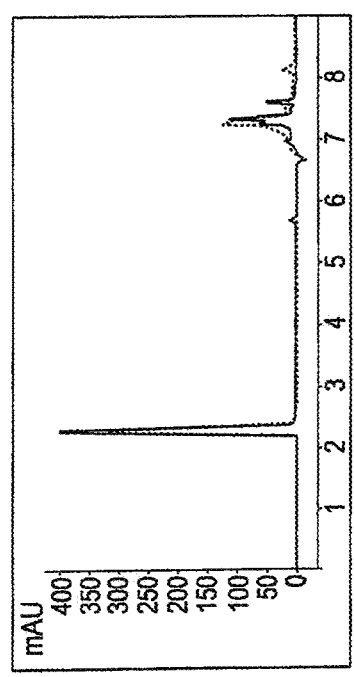
Figure 13B:
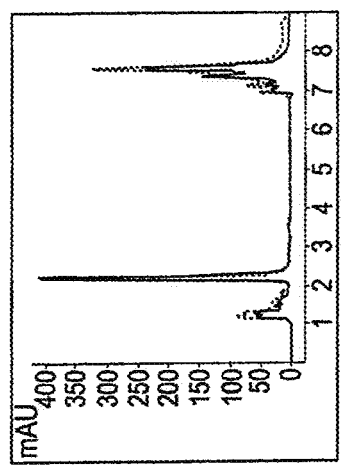
Figure 13C:
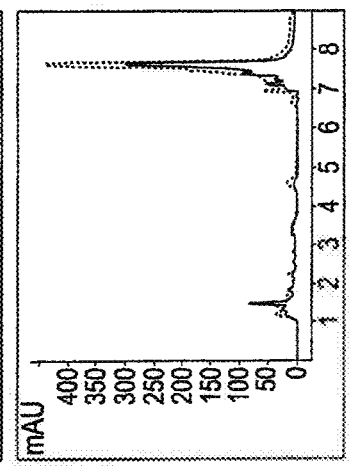
Figure 13F:
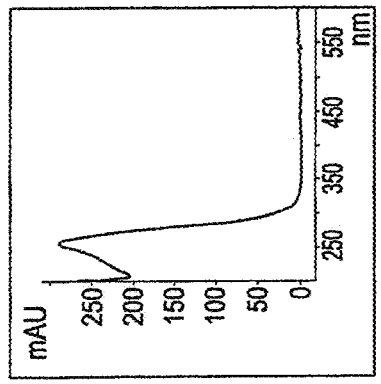
Figure 13H:
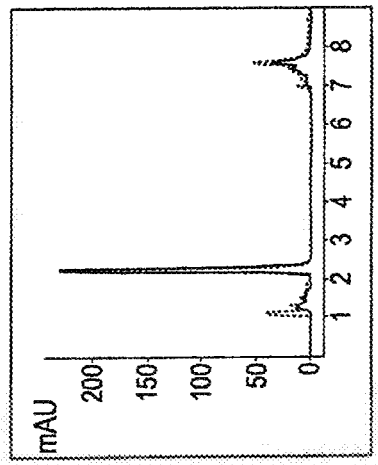
Figure 13G:
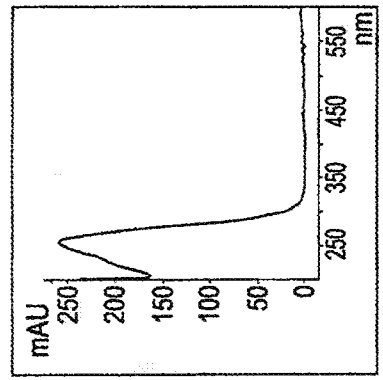
Figure 13I:
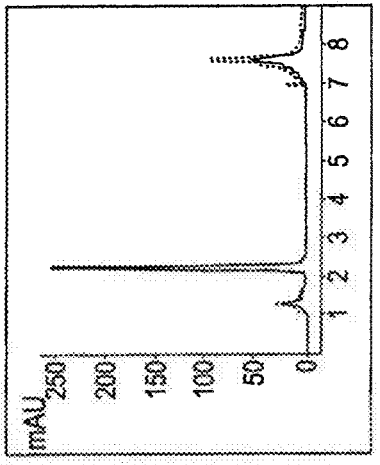

Genomic DNA of the clones was isolated and cases of single crossing-over of the plasmids into the genome of *A. japonicum* were examined for the presence of an apramycin resistance cassette by PCR and specifically deduced using primers to confirm integration of pGusA21Δorf5768 into the genome. Using the primer pair of orf5768-SCO-FP and orf5768-SCO-RP a fragment of 1677 bp (orf5768-SCO-wt-Frag) and/or a fragment of 1293 bp (orf5768-SCO-single Frag) were amplified which represents the wild-type genome and the genome with integrated pGusA21Δorf5768, respectively (FIGS. 12A and 12B).

The clones of *A. japonicum* having the pGusA21Δorf5768 integrated in the genome (clones 1, 6, 7, and 8) were combined and used for inducing a double crossing-over (homologue recombination), wherein cells were cultured under temperature stress conditions.

A total of three mutants of *A. japonicum* (*A. japonicum* Δzur) were generated in an in-frame deletion of the encoding region SEQ ID No. 62. *A. japonicum* WT and all the generated mutants were cultured in EDDS production medium (cf. Table 1). While the *A. japonicum* WT strain did not produce [S,S]-EDDS under the zinc-rich conditions, none of the three mutants exhibited zinc repression (FIGS. 13A-13I).

We demonstrated that the deletion of the zinc-responsive repressor of *A. japonicum* ($Zur_{AJ}$ or nucleic acid sequence according to SEQ ID No. 62) leads to a zinc-independent [S,S]-EDDS production.

Figure 14:
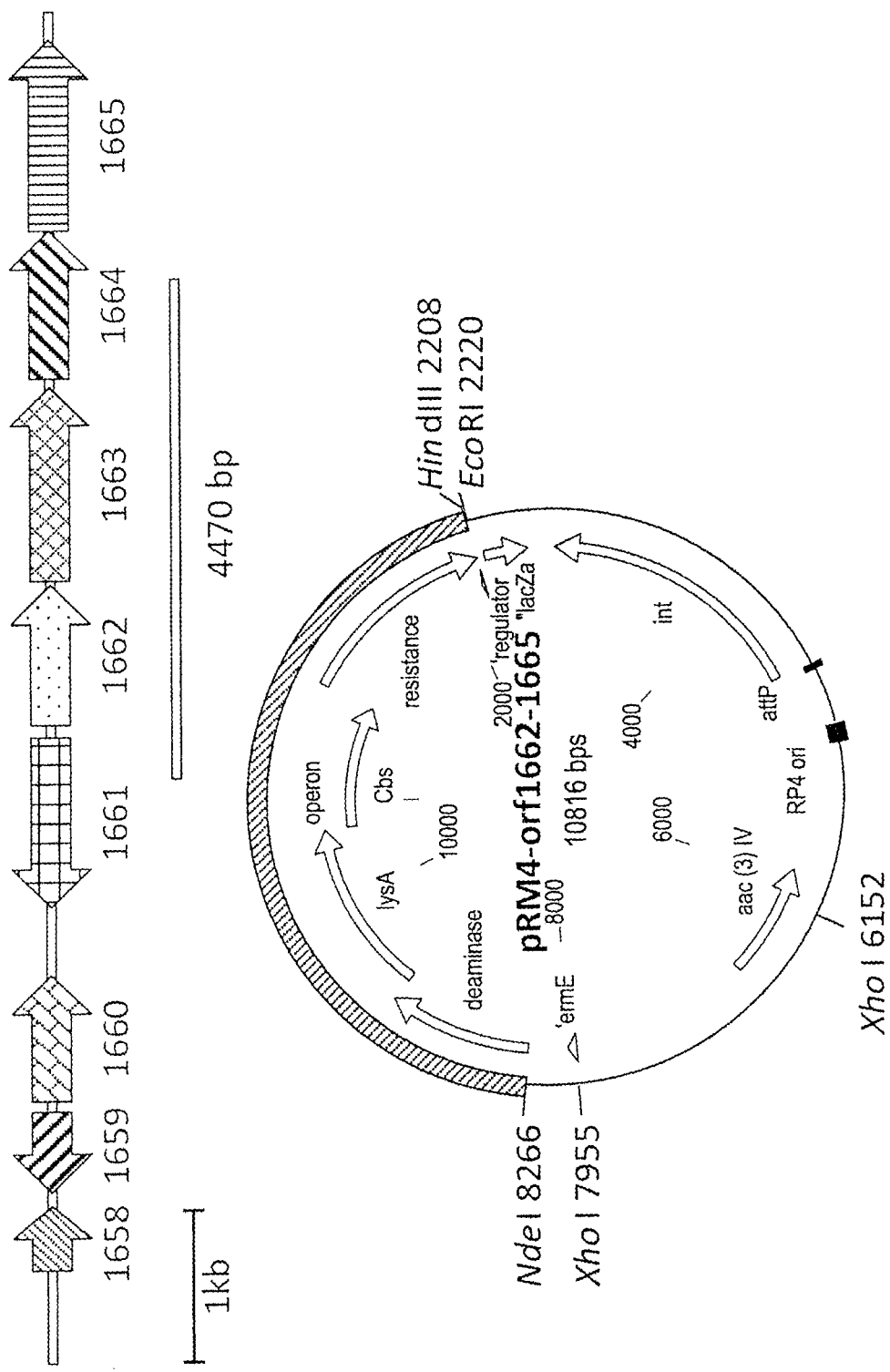
FIG. 14 shows a schematic representation of the construction of vector pRM4-PermE*orf1662-65. (Top) [S,S]-EDDS gene cluster orf1658-1665 (corresponding to SEQ ID No. 40, 42, 44, 46, 48, 50, 52, and 54). (Bottom) Illustration of the homologues expression vector pRM4-PermE*orf1662-65 in a plasmid map (orf1662 to orf1665 under control of PermE*. Grey bar: operon orf1662 to orf1665.

3.2 Expression of the [S,S]-EDDS Biosynthesis Genes Under the Control of None-Zinc-Repressed Promoters A second strategy to generate a zinc derepressed [S,S]-EDDS production strain is to avoid the Zur (proteins or peptides according to SEQ ID No. 61) mediated zinc repression by exchanging the Zur-target promoters by rather strong constitutively expressed or inducible promoters. The established, constitutively expressed promoter PermE* was chosen to express the [S,S]-EDDS operon (SEQ ID No. 48, 50, 52, and 54, corresponding to orf1662-65) under its control. The generated plasmid pRM4-PermE*orf1662-65 was transferred into A. japonicum WT, and thereby A. japonicum+pRM4-PermE*orf1662-65 was obtained (FIG. 14).

Figure 15:
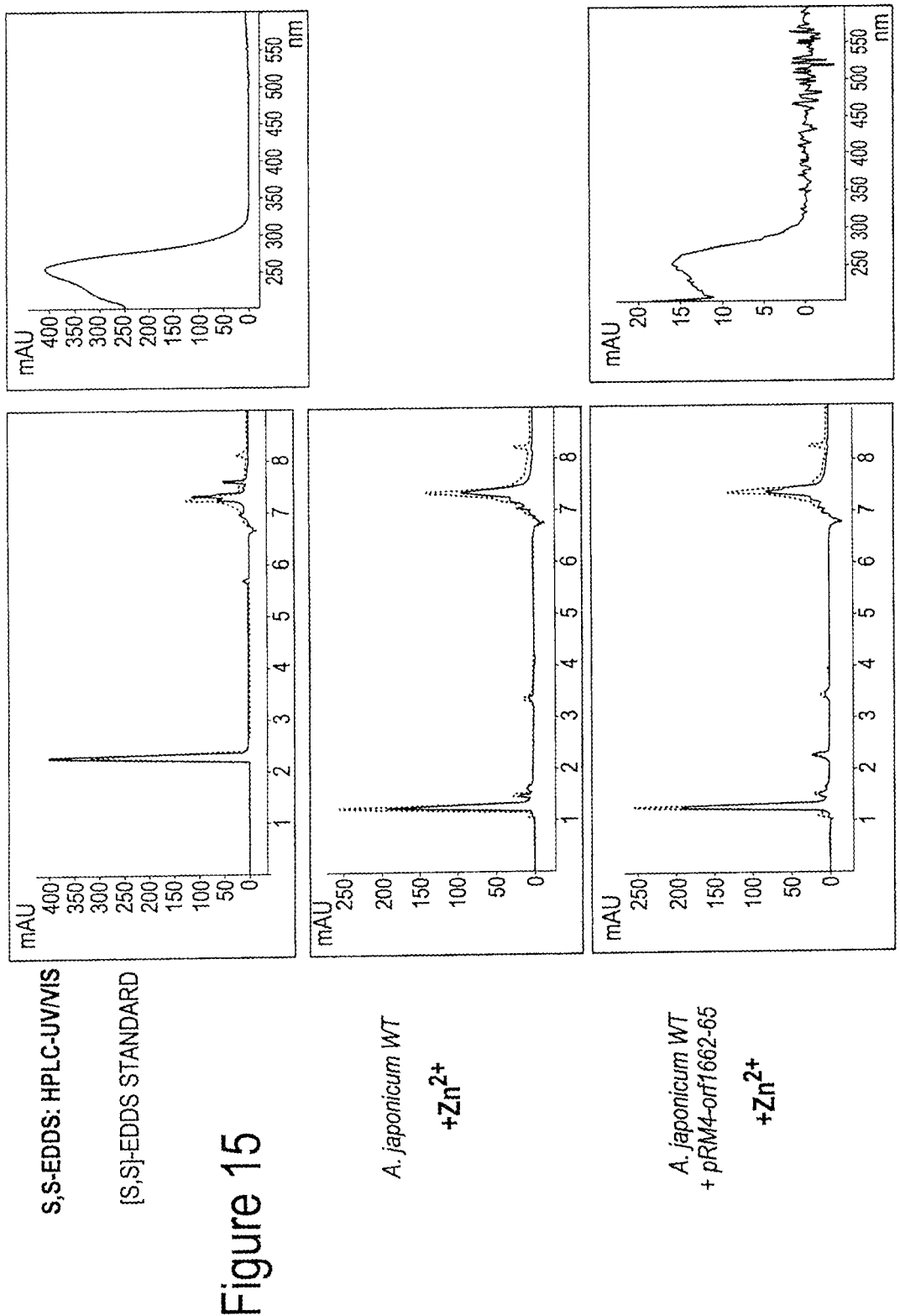
FIG. 15 shows a HPLC-UV/VIS analysis of the supernatants of *A. japonicum* WT and *A. japonicum*+pRM4-PermE*orf1662-65 after growth in M7 medium for 72 h with a supplementation of 6 µM $ZnSO_4$. (Top) [S,S]-EDDS standard [350 mg/L]. (Middle) *A. japonicum* WT+6 µM $ZnSO_4$. (Bottom) *A. japonicum* pRM4-PermE*orf1662-65+6 µM $ZnSO_4$. (Right) Specific UV/VIS spectra of [S,S]-EDDS.

A. japonicum WT and A. japonicum+pRM4-PermE*orf1662-65 were then grown in EDDS-production media (cf. Table 1) supplemented with 6 µM ZnSO$_4$. Data according to FIG. 15 show that there is no [S,S]-EDDS production by A. japonicum WT under the chosen conditions. However, there is detectable [S,S]-EDDS production in the presence of zinc by the A. japonicum strain expressing the [S,S]-EDDS operon orf1662-65 under control of the none-Zur-targeted promoter ermE* (FIG. 15).

These data demonstrate that a significant zinc-independent [S,S]-EDDS production may be achieved by exchanging the Zur$_{AJ}$-targeted (SEQ ID No. 61) promoters controlling the [S,S]-EDDS biosynthesis genes.

3.3 Heterologous Expression of the [S,S]-EDDS Biosynthesis Genes in Heterologous Host Cells The [S,S]-EDDS biosynthesis cluster is to be expressed in already biotechnologically applied bacterial strains, like S. coelicolor, for example.

Figure 16:
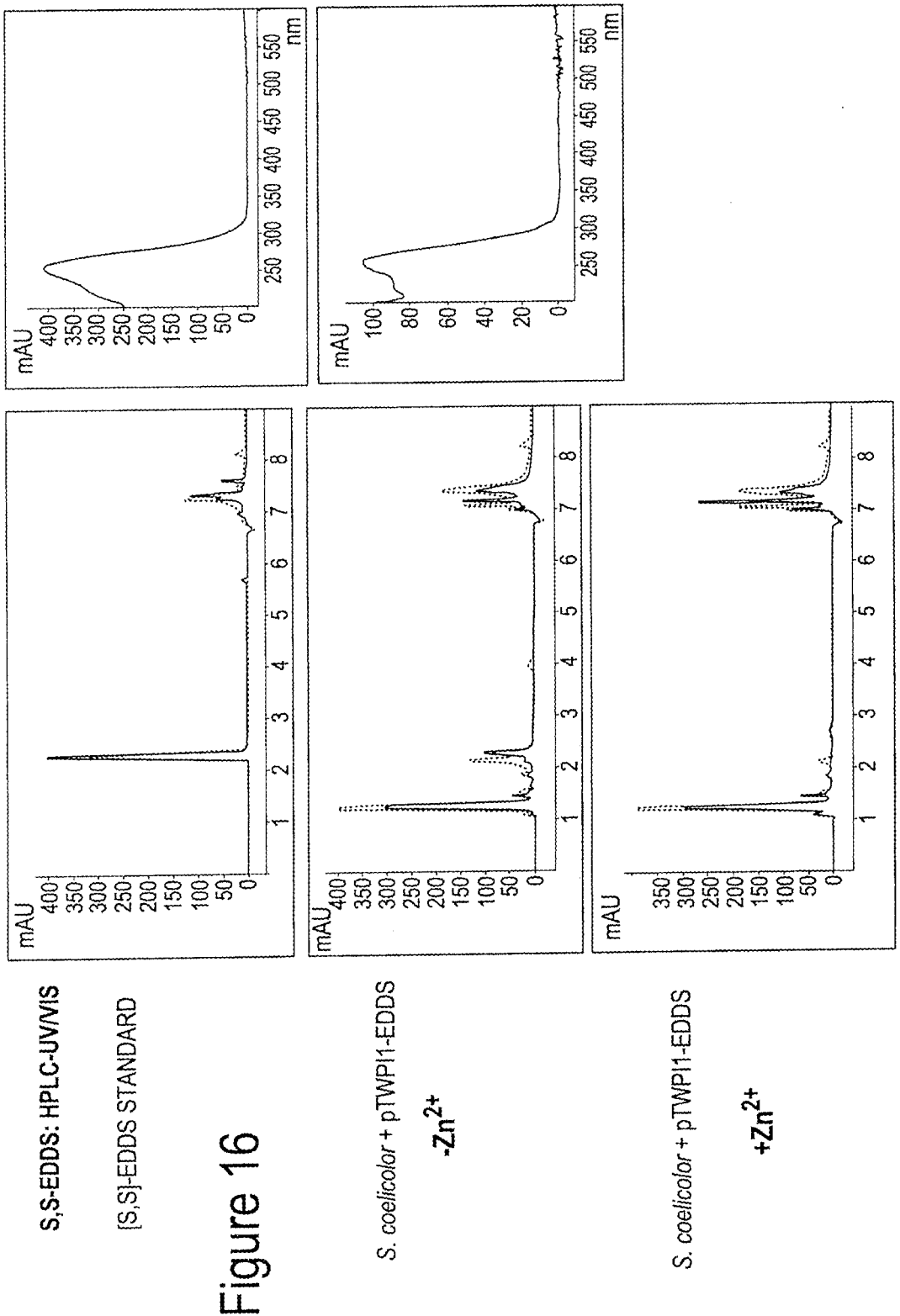
FIG. 16 shows a HPLC-UV/VIS analysis of the supernatants of *S. coelicolor*+pTWPL1-EDDS after growth in M7 medium for 72 h with supplementation of 6 µM $ZnSO_4$. (Top) [S,S]-EDDS standard [350 mg/L]. (Middle) *S. coelicolor*+pTWPL1-EDDS–6 µM $ZnSO_4$. (Bottom) *S. coelicolor*+pTWPL1-EDDS+6 µM $ZnSO_4$. (Right) Specific UV/VIS spectra of [S,S]-EDDS.

Therefore, the S. coelicolor strain with the cosmid pTWPL1-EDDS integrated in the genome was grown in EDDS production medium and screened for [S,S]-EDDS production (FIG. 16).

The data confirm that [S,S]-EDDS can be synthesized by heterologous expression in the host S. coelicolor in zinc-free EDDS production medium (FIG. 16, middle). These data also confirm that the genes identified are [S,S]-EDDS biosynthesis genes.

4. Culturing and Storing of A. japonicum

To produce cultures of A. japonicum, lyophilisates were plated on HA plates and incubated at 27° C. for 4 to 5 days. Subsequently, 100 ml M3 medium (cf. Table 1) were inoculated with mycelium and incubated at 27° C. for 48 h. The cultures were washed twice with saline solution (0.9% NaCl). The precipitate was suspended in 50 ml M2 medium (cf. Table 1), portioned in 2 ml aliquots, and stored at −20° C. for up to 6 months.

5. Culturing of A. japonicum for DNA Isolation 20 ml of TSB medium (cf. Table 1) were inoculated with mycelium and incubated at 27° C. for 2 days. Disperse growth and optimized oxygen supply were obtained in a 100 ml Erlenmeyer flask equipped with a baffle and a metal coil.

6. Culturing of A. japonicum Under [S,S]-EDDS Biosynthesis Conditions

A. japonicum was plated on HA plates and incubated at 27° C. for 3 to 5 days. Subsequently, about 1 cm$^2$ A. japonicum mycelium were wiped off the plate and used for inoculation of 100 ml M3 medium (cf. Table 1). After 48 h of incubation at 27° C. and 180 rpm in an agitator, 5 ml were used for inoculation of 100 ml M7 medium (cf. Table 1). M7 is a synthetic zinc-depleted medium, wherein A. japonicum will produce [S,S]-EDDS. To prevent biosynthesis of [S,S]-EDDS, ZnSO$_4$ was added up to a final concentration of 6 µM. For RT-PCR, there was addition of ZnSO$_4$, FeSO$_4$, MnSO$_4$, NiSO$_4$, and CoCl$_2$, respectively up to a final concentration of 25 µM (cf. FIG. 3, e.g.).

The nucleic acid and amino acid sequences correspond to the sequences listed in the annexed sequence listing.

The invention claimed is:

1. An expression vector, including 1) at least one nucleic acid including or composed of a nucleic acid sequence selected from the group consisting of
    a) a nucleic acid sequence encoding for a protein or peptide which is functional for a partial synthesis step of the biosynthesis of [S,S]-ethylenediamine-disuccinate, including or composed of an amino acid sequence selected from the group consisting of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, and combinations thereof;
    b) a nucleic acid sequence differing from the nucleic acid sequence according to a) in the exchange of at least one codon for a synonymous codon;
    c) a nucleic acid sequence corresponding to the complementary strand of the nucleic acid sequence according to a), and combinations thereof, or
    a gene cluster or operon including or composed of at least two nucleic acid sequences selected from the group consisting of SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and combinations thereof; and
    2) a promoter that is not subject to zinc regulation.

2. A host cell, including at least one protein or peptide which is functional for a partial synthesis step of the biosynthesis of [S,S]-ethylenediamine-disuccinate, including or composed of an amino acid sequence selected from the group consisting of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, and combinations thereof, at least one nucleic acid including or composed of a nucleic acid sequence selected from the group consisting of
    a) a nucleic acid sequence encoding for a protein or peptide, which is functional for a partial synthesis step of the biosynthesis of [S,S]-ethylenediamine-disuccinate, including or composed of an amino acid sequence selected from the group consisting of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, and combinations thereof;
    b) a nucleic acid sequence differing from the nucleic acid sequence according to a) in the exchange of at least one codon for a synonymous codon; and
    c) a nucleic acid sequence corresponding to the complementary strand of the nucleic acid sequence according to a), and combinations thereof;
    a gene cluster or operon including or composed of at least two nucleic acid sequences selected from the group consisting of SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and combinations thereof, and/or
    an expression vector, including at least one nucleic acid including or composed of a nucleic acid sequence selected from the group consisting of
    a) a nucleic acid sequence encoding for a protein or peptide, which is functional for a partial synthesis step of the biosynthesis of [S,S]-ethylenediamine-disuccinate, including or composed of an amino acid sequence selected from the group consisting of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, and combinations thereof;
    b) a nucleic acid sequence differing from the nucleic acid sequence according to a) in the exchange of at least one codon for a synonymous codon; and
    c) a nucleic acid sequence corresponding to the complementary strand of the nucleic acid sequence according to a), and combinations thereof; and
    a gene cluster or operon, including or composed of at least two nucleic acid sequences selected from the group consisting of SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and combinations thereof, wherein zinc repression is not allowed in the host cell.

3. The host cell according to claim 2, that does not include any nucleic acid encoding for a Zur protein and/or includes no Zur protein or a protein or peptide homologous thereto.

4. The host cell according to claim 2, that includes no nucleic acid according to nucleic acid sequence SEQ ID NO: 62 or a nucleic acid homologous thereto and/or no protein or peptide according to amino acid sequence SEQ ID NO: 61 or a protein or peptide homologous thereto.

* * * * *

SEQUENCE LISTING

```
<160> NUMBER OF SEQ ID NOS: 65

<210> SEQ ID NO 1
<211> LENGTH: 541
<212> TYPE: PRT
<213> ORGANISM: Amycolatopsis japonicum
<220> FEATURE:
<223> OTHER INFORMATION: ORF 1639

<400> SEQUENCE: 1

Met Thr Arg Lys Glu Pro Ala Asp Thr Pro Leu Gly Asp Ala Phe His
1               5                   10                  15

Leu Tyr Asp Thr Thr Leu Arg Asp Gly Ala Gln Arg Glu Gly Ile Ser
            20                  25                  30

Tyr Ser Val Ala Asp Lys Leu Ala Val Ala Arg Leu Leu Asp Glu Leu
        35                  40                  45

Gly Val Gly Phe Ile Glu Gly Gly Trp Pro Gly Ala Leu Pro Lys Asp
    50                  55                  60

Thr Glu Phe Phe Ala Arg Ala Ala Ser Gly Glu Leu Lys Leu Arg His
65                  70                  75                  80

Ala Ala Leu Val Ala Phe Gly Ala Thr Arg Lys Ala Gly Thr Lys Ala
                85                  90                  95

Glu Gln Asp Gln Gln Val Arg Ala Leu Leu Asp Ser Gln Ala Pro Val
            100                 105                 110

Val Thr Leu Val Ala Lys Ser Asp Leu Arg His Ile Glu Arg Ala Leu
```

-continued

```
            115                 120                 125
Arg Val Asp Val Asp Glu Ala Cys Glu Met Val Arg Asp Thr Val Ala
    130                 135                 140
Phe Leu Val Gly Glu Gly Arg Val Phe Leu Asp Ala Glu His Phe
145                 150                 155                 160
Phe Asp Gly Tyr Ala Phe Ser Pro Asp Thr Ala Leu Lys Val Leu Asp
                165                 170                 175
Ala Gly Val Asn Ala Gly Ala Asp Val Ala Val Leu Cys Asp Thr Asn
            180                 185                 190
Gly Gly Gln Leu Pro Leu Gly Leu Ala Glu Thr Val Arg Glu Val Lys
            195                 200                 205
Glu Arg Thr Gly Phe Arg Leu Gly Ile His Cys Gln Asp Asp Thr Ser
    210                 215                 220
Cys Ala Val Ala Asn Ser Val Ala Ala Val Gln Ala Gly Val Thr His
225                 230                 235                 240
Val Gln Cys Thr Ala Asn Gly Tyr Gly Glu Arg Ala Gly Asn Ala Asp
                245                 250                 255
Leu Phe Ala Val Thr Gly Asn Leu Val Thr Lys Leu Gly Met Glu Val
                260                 265                 270
Leu Pro Thr Gly Gly Ala Ala Glu Leu Thr Arg Val Ser His Ala Leu
            275                 280                 285
Ala Glu Ile Ala Asn Ile Ala Pro Tyr Thr His Gln Ala Tyr Val Gly
    290                 295                 300
Ala Ser Ala Phe Ala His Lys Ala Gly Leu His Ala Ser Ala Ile Lys
305                 310                 315                 320
Val Asp Pro Leu Leu Tyr Asn His Ile Asp Pro Ala Ser Val Gly Asn
                325                 330                 335
Asp Met Arg Val Leu Val Thr Glu Met Ala Gly Arg Ala Ser Leu Glu
            340                 345                 350
Leu Lys Gly Arg Glu Leu Gly Val Asp Leu Ala Gly Gln Pro Glu Ala
            355                 360                 365
Leu Thr Ser Ala Val Lys Lys Val Lys Arg Leu Glu Ser Glu Gly Trp
    370                 375                 380
Ser Phe Glu Ala Ala Asp Ala Ser Leu Glu Leu Leu Arg Arg Glu
385                 390                 395                 400
Val Asp Gly Pro Gln Ser Asp Val Leu Asp Glu Pro Pro Phe Glu Leu
                405                 410                 415
Glu Ser Tyr Arg Val Val Leu Asp His Arg Ser Asp Gly Glu Val Val
                420                 425                 430
Ser Glu Ala Thr Val Lys Val His Val Ala Gly Gln Arg Val Ile Ala
            435                 440                 445
Thr Ala Glu Gly Asn Gly Pro Val His Ala Leu Asp Ala Ala Leu Arg
            450                 455                 460
Glu Ala Leu Ser Pro His Leu Ser Trp Leu Asp Ser Val Glu Leu Ala
465                 470                 475                 480
Asp Tyr Lys Val Arg Ile Leu Pro Gly His Pro Gly Thr Asp Ala Val
                485                 490                 495
Thr Arg Val Leu Val Glu Thr Ser Asp Gly Glu Arg Glu Trp Thr Thr
            500                 505                 510
Val Gly Val His Gly Asn Ile Val Glu Ala Ser Trp Leu Ala Leu Cys
            515                 520                 525
Asp Ala Leu Val His Lys Ser Leu Ser Glu Gly Pro Ala
            530                 535                 540
```

<210> SEQ ID NO 2
<211> LENGTH: 1626
<212> TYPE: DNA
<213> ORGANISM: Amycolatopsis japonicum
<220> FEATURE:
<223> OTHER INFORMATION: orf 1639

<400> SEQUENCE: 2

| | | | | | |
|---|---|---|---|---|---|
| gtgacccgca | aggagcccgc | cgatacaccg | ctcggcgacg | ccttccacct | gtacgacacg | 60 |
| acgttgcgcg | acggtgcgca | gcgtgagggg | atctcctact | ccgtcgcgga | caaactggcg | 120 |
| gtggcgaggc | tgctcgacga | actcggggtc | gggttcatcg | aaggcggatg | gccgggcgcg | 180 |
| ctgcccaagg | acacggaatt | cttcgcccgt | gcggcttcgg | gcgagctgaa | acttcgccat | 240 |
| gccgcgctcg | tcgcgttcgg | cgcgacgcgg | aaggcgggca | ccaaggccga | gcaggatcag | 300 |
| caggtgcggg | ccctgctcga | ctcgcaggca | ccggtggtca | cgctcgtggc | caaatccgat | 360 |
| ctgcggcaca | tcgaacgcgc | gctgcgggtc | gacgtcgacg | aagcttgcga | gatggtgcgc | 420 |
| gacaccgtcg | cgttcctcgt | cggtgaagga | cgtcgcgtct | tccttgacgc | ggaacacttt | 480 |
| ttcgacggct | acgcgttctc | cccggacacc | gcgctgaagg | tgctcgacgc | gggcgtgaac | 540 |
| gcgggtgccg | acgtcgccgt | gctgtgcgac | accaacggcg | ggcaactgcc | gctcggactc | 600 |
| gcggaaaccg | tccgcgaggt | caaggaaagg | accggattcc | ggctcggaat | ccattgtcag | 660 |
| gacgacactt | cctgcgcggt | ggcgaattcc | gtcgccgccg | tgcaggccgg | cgtgacgcac | 720 |
| gtccagtgca | ccgccaatgg | ttacggcgag | cgggcgggta | acgccgatct | tttcgccgtg | 780 |
| acagggaatt | tggtgaccaa | gctcggtatg | gaggtgctcc | cgaccggagg | cgccgccgag | 840 |
| ctcacccggg | tctcccatgc | ccttgccgaa | atcgcgaaca | tcgccccta | cacccaccag | 900 |
| gcttacgtag | gggcgtcggc | cttcgcccac | aaggcgggac | tgcacgcgag | cgcgatcaag | 960 |
| gtggatccgt | tgctgtacaa | ccacatcgat | ccagcttctg | tcggcaatga | catgcgggta | 1020 |
| ctggtcaccg | agatggccgg | cagggccagc | ctggagctca | agggacgtga | gctcggggtc | 1080 |
| gaccttgccg | ccagcccga | ggcgctgacg | agcgccgtga | agaaggtgaa | acgcctcgaa | 1140 |
| tccgaaggct | ggtccttcga | agccgcggac | gcttcactgg | aactgctgct | gcggcgggag | 1200 |
| gtcgacggcc | cgcagagcga | cgtcctcgac | gaaccgccgt | tcgaactcga | gtcgtaccgg | 1260 |
| gtcgtcctcg | accaccggtc | cgacggcgag | gtcgtctccg | aggcgacggt | gaaggtgcac | 1320 |
| gtcgccgggc | agcgcgtgat | cgcgaccgcc | gagggcaacg | ggcccgtgca | cgcgctcgac | 1380 |
| gccgccctgc | gcgaggcgct | cagcccgcat | ctgtcctggt | tggacagtgt | cgagctggcc | 1440 |
| gactacaagg | tgcggatcct | gcccggccat | ccgggcaccg | acgccgtcac | ccgtgtgctc | 1500 |
| gtcgagacca | gcgacggcga | gcgcgagtgg | accaccgtcg | gcgtgcacgg | caacatcgtc | 1560 |
| gaggcgagct | ggctggcgct | gtgcgacgcg | ctcgtgcaca | gtccctcag | cgagggcccg | 1620 |
| gcgtga | | | | | | 1626 |

<210> SEQ ID NO 3
<211> LENGTH: 256
<212> TYPE: PRT
<213> ORGANISM: Amycolatopsis japonicum
<220> FEATURE:
<223> OTHER INFORMATION: ORF 1640

<400> SEQUENCE: 3

Met Arg Leu Ala Arg Ile Ala His Pro Gly Gly Val Ala Phe Ala Ser
1               5                   10                  15

Ile Glu Gly Asp Gly Asp Ala Gln Val Leu Glu Ile Ala Glu His
            20                  25                  30

Pro Phe Gly Asn Pro Asn Phe Thr Gly Lys Arg Trp Pro Leu Ala Asp
            35                  40                  45

Val Arg Leu Leu Ala Pro Ile Leu Pro Ser Lys Val Ile Ala Val Gly
 50                  55                  60

Arg Asn Tyr Ala Lys His Ala Ala Glu Phe Gly Asn Glu Val Pro Gln
 65                  70                  75                  80

Asp Pro Met Leu Phe Ile Lys Pro Ser Thr Thr Val Ile Gly Pro Asn
                 85                  90                  95

Val Pro Ile Arg Arg Pro Arg Gly Val Gly Arg Val Asp Phe Glu Gly
            100                 105                 110

Glu Leu Ala Ile Val Ile Gly Gln Pro Val Lys Asn Val Pro Ala Ala
            115                 120                 125

Arg Ala Ala Ser Ala Ile Leu Gly Tyr Thr Val Ala Asn Asp Val Ser
130                 135                 140

Ala Arg Asp Leu Gln Lys Ser Asp Gly Gln Trp Gly Arg Ala Lys Gly
145                 150                 155                 160

Phe Asp Thr Phe Cys Pro Leu Gly Pro Trp Ile Glu Thr Ser Leu Asp
                165                 170                 175

Ala Ala Asp Leu Ala Leu Lys Ser Glu Val Asp Gly Val Leu Lys Gln
            180                 185                 190

Asp Gly Arg Thr Ser Asp Leu Val His Lys Ile Pro Glu Leu Val Glu
            195                 200                 205

Phe Val Ser Gly Val Met Thr Leu Leu Pro Gly Asp Val Ile Leu Thr
            210                 215                 220

Gly Thr Pro Glu Gly Val Gly Pro Ile Glu Asp Gly Gln Ser Val Ser
225                 230                 235                 240

Ile Thr Ile Glu Gly Ile Gly Thr Leu Thr Asn Pro Val Gln Asp Ile
                245                 250                 255

<210> SEQ ID NO 4
<211> LENGTH: 771
<212> TYPE: DNA
<213> ORGANISM: Amycolatopsis japonicum
<220> FEATURE:
<223> OTHER INFORMATION: orf 1640

<400> SEQUENCE: 4
gtgcgtctag cccgaattgc tcatcccggt ggtgtcgcgt tcgcttcgat cgaagggac      60 ggcgacgacg cccaggtact ggaaatcgcc gagcacccct tcggcaaccc caacttcacc    120
ggcaaacgct ggccgctcgc cgacgtccgg ctgctcgcgc cgatcctgcc gtcgaaggtg    180
atcgcggtcg gccggaacta cgccaagcac gcggccgagt tcggcaacga ggtcccgcag    240
gacccgatgc tgttcatcaa gccgtcgacc acggtgatcg gcccgaacgt gccgatccgc    300
cgtccgcgcg gtgtcggccg tgtcgacttc gagggcgaac tggcgatcgt catcggccag    360
ccggtcaaga acgtgcccgc cgcccgcgcg gcgagcgcga tcctcggcta caccgtggcg    420
aacgacgtca gcgcgcgtga cctgcagaag tccgacggcc agtggggcag gcgaagggt    480 ttcgacacct tctgcccgct gggcccgtgg atcgagacct cgctcgacgc ggccgatctc    540
gcgctcaagt ccgaggtgga cggtgtgctc aagcaggacg gccggacgtc ggacctggtg    600
cacaagatcc ccgagctggt cgaattcgtg tccggggtga tgaccctgtt gcccggtgac    660
gtcatcctga ccggcacgcc cgagggcgtc ggcccgatcg aggacggcca gtccgtgtcg    720
atcaccatcg agggcatcgg caccctgacg aacccggttc aagacatcta g    771

<210> SEQ ID NO 5
<211> LENGTH: 411
<212> TYPE: PRT
<213> ORGANISM: Amycolatopsis japonicum
<220> FEATURE:
<223> OTHER INFORMATION: ORF 1641

<400> SEQUENCE: 5

```
Met Asn Glu Arg Thr Asn Cys Val Val Gly Gly Pro Ala Gly
1               5                   10                  15

Met Val Ala Gly Leu Leu Ala Arg Ala Gly Val Glu Val Thr Val
            20                  25                  30

Leu Glu Lys His Gln Asp Phe Leu Arg Asp Phe Arg Gly Asp Thr Val
        35                  40                  45

His Pro Ser Thr Leu Thr Leu Leu Asp Glu Leu Gly Leu Ser Glu Lys
    50                  55                  60

Phe Leu Ser Leu Pro His Ser Glu Ile Ala Tyr Ala Gly Phe Pro Ala
65                  70                  75                  80

Glu Asp Gly Thr Met Met Arg Leu Ala Asp Leu Thr Arg Leu Lys Val
                85                  90                  95

Ala His Pro Tyr Ile Ala Met Val Pro Gln Trp Asp Phe Leu Asp Leu
            100                 105                 110

Leu Ala Asp Ala Gly Ala Lys Glu Pro Thr Phe Thr Leu Arg Gln Ser
        115                 120                 125

Thr Glu Met Thr Gly Leu Ile Phe Glu His Gly Arg Val Ser Gly Val
    130                 135                 140

Arg Tyr Arg Asp Ala Asp Gly Lys Ala Gly Glu Leu Arg Ala Asp Leu
145                 150                 155                 160

Val Ile Ala Ala Asp Gly Arg Trp Ser Leu Ala Arg Arg Glu Ala Gly
                165                 170                 175

Leu Met Thr Lys Asp Tyr Pro Ile Pro Phe Asp Ala Trp Trp Phe Arg
            180                 185                 190

Ile Ser Arg Arg Asp Gly Glu Arg Glu Gly Met Leu Thr Pro Lys Met
        195                 200                 205

Arg Asp Arg Arg Phe Ala Val Pro Leu Pro Arg Lys Gly Tyr Phe Gln
    210                 215                 220

Ile Ala Tyr Leu Ser Pro Lys Gly Gln Asp Leu Arg Asp Lys Gly Ile
225                 230                 235                 240

Glu Ala Phe Arg Glu Asn Val Ala Ala Ile Leu Pro Glu Leu Ala Asp
                245                 250                 255

Arg Val Asp Glu Leu Lys Thr Thr Asp Asp Val Lys Phe Leu Asp Val
            260                 265                 270

Lys Met Asn Leu Leu Arg Lys Trp His Leu Asp Gly Leu Leu Cys Ile
        275                 280                 285

Gly Asp Ala Ala His Ala Met Ser Pro Val Gly Gly Val Gly Ile Asn
    290                 295                 300

Leu Ala Val Gln Asp Ala Val Ala Ala Thr Leu Leu Ala Glu Pro
305                 310                 315                 320

Leu Arg Arg Gly Arg Pro Ser Val Ala Asp Leu Ala Lys Val Arg Lys
                325                 330                 335

Arg Arg Leu Ala Pro Thr Met Leu Val Gln Gly Leu Gln Arg Ile Leu
            340                 345                 350
```

His Lys Asn Val Met Gly Pro Val Met Ala Gly Lys Arg Asn Gly Pro
            355                 360                 365

Pro Ala Pro Met Val Lys Leu Phe Ser Arg Phe Pro Ala Leu Ser Tyr
        370                 375                 380

Ile Pro Ala Arg Leu Leu Gly Leu Gly Leu Arg Pro Glu His Ala Pro
385                 390                 395                 400

Ala Phe Ala Arg Arg Ala Met Glu Pro Ala Gly
                405                 410

<210> SEQ ID NO 6
<211> LENGTH: 1236
<212> TYPE: DNA
<213> ORGANISM: Amycolatopsis japonicum
<220> FEATURE:
<223> OTHER INFORMATION: orf 1641

<400> SEQUENCE: 6

```
atgaacgaac gtacgaactg cgtggtcgtc ggcggtggcc ccgcgggtat ggtcgccgga    60
ttgctgctgg ccagggccgg ggtcgaggtc accgtgctgg agaagcacca ggacttcctg   120
cgggacttcc gcggcgacac cgtgcacccg tcgacgttga cgttgctgga cgagctgggc   180
ctcagcgaga aattcctcag cctgccgcac agcgagatcg cctacgccgg cttccccgcc   240
gaggacggca cgatgatgcg cctcgccgac ctgaccaggc tgaaggtggc gcaccgtac    300
atcgccatgg tcccgcagtg ggacttcctg gacctgctcg ccgacgccgg ggcgaaggaa   360
cccacgttca cgctgcggca gagcaccgag atgaccgggc tgatcttcga cacggccgg    420
gtgagcgggg tccgctaccg cgacgccgac gggaaggccg cgaactgcg cgccgacctg    480
gtgatcgccg ccgacggacg ctggtcgctg gcccgccgcg aggccgggct catgacgaag   540
gactacccca tcccgttcga cgcgtggtgg ttccggatct cacggcggga cggggaacgc   600
gaaggcatgc tgaccccgaa gatgcgggat cgccgcttcg ccgtgccgct gccccgcaag   660
ggctacttcc agatcgccta cctcagcccc aagggccagg acctgcgcga caagggcatc   720
gaggcgttcc gggagaacgt ggccgcgatc ctgcccgagc tggccgaccg cgtggacgag   780
ctgaagacga cggacgacgt caaattcctc gacgtcaaga tgaacctgct gcggaagtgg   840
catctcgacg gctgctgtg catcggtgac gcggcgcacg cgatgtcgcc ggtcggcggg   900
gtcggcatca acctcgcggt gcaggacgcg gtcgcggccg ccaccctgct cgccgaaccg   960
ctgcgccgcg gcaggccgtc ggtggcggat ctggcgaagg tccgcaagcg ccgtctcgcg  1020
cccacgatgc tggtgcaggg gctgcagcgg attctgcaca gaacgtgat ggggccggtg   1080
atggcgggca agcgcaacgg cccgcccgcg ccgatggtga agctgttcag ccggttcccc   1140
gcgctgtcct acatccccgc gcggctgctg ggcctggggc tgcggcccga gcacgccccg  1200
gccttcgcgc ggcgggcgat ggaaccggcc ggttag                             1236
```

<210> SEQ ID NO 7
<211> LENGTH: 244
<212> TYPE: PRT
<213> ORGANISM: Amycolatopsis japonicum
<220> FEATURE:
<223> OTHER INFORMATION: ORF 1642

<400> SEQUENCE: 7

Met Cys Leu Asp Ile Asp Asp Thr Leu Ile Asp Cys Thr Ala Ala Ile
1               5                   10                  15

Arg Leu Ser Leu Ser Ala Leu Thr Gly Gln Asn Asp Leu Trp Pro Leu
            20                  25                  30

```
Trp Asp Leu Ile Thr Glu Glu His Val Ala Leu Val Val Ala Gly Glu
         35                  40                  45

Ile Asp Tyr Ala Thr Met His Tyr Lys Arg Thr Glu Cys Phe Leu Ala
 50                  55                  60

Glu Ile Gly Ile Leu Ala Asp Glu Gln Gln Val Ser Gly Phe Glu Arg
 65                  70                  75                  80

Arg Arg Arg Glu Ile Leu Thr Arg Ser Trp Gln Leu Phe Glu Asp Val
                 85                  90                  95

Leu Pro Cys Leu Glu Trp Leu Arg Ala Ala Gly Val Leu Val Ala Ala
                100                 105                 110

Val Thr Asn Ala Ser Gly Ala His Gln Arg Lys Lys Ile Ala Asp Leu
                115                 120                 125

Gly Leu Ala Arg Phe Phe Asp His Val Ala Ile Ala Gly Glu Leu Gly
130                 135                 140

Val Ala Lys Pro Asp Pro Ala Met Phe His Ser Val Cys Leu Gly Leu
145                 150                 155                 160

Gly Cys Asp Pro Ala Gln Ala Val His Val Gly Asp Lys Leu Asp Thr
                165                 170                 175

Asp Ala Ile Gly Ala Arg Asp Ala Gly Leu Gly Ala Val Trp Leu Asp
                180                 185                 190

Arg Asp Gly Ile Ala Glu Arg Ala Pro Ala Gly Val His Thr Ile Ser
                195                 200                 205

Gly Leu Asp Glu Leu Pro Glu Leu Leu Val Ser Glu Phe Ala Lys Leu
210                 215                 220

Gly Val Pro Ala Gln Arg Ala Thr Glu Thr Pro Ala Phe Thr Val Arg
225                 230                 235                 240

Asn Ser Val Leu

<210> SEQ ID NO 8
<211> LENGTH: 735
<212> TYPE: DNA
<213> ORGANISM: Amycolatopsis japonicum
<220> FEATURE:
<223> OTHER INFORMATION: orf 1642

<400> SEQUENCE: 8
gtgtgcctcg acatcgatga cacgttgatc gactgcacgg cggcgatccg cctcagcctg      60
agcgccctca ctggccagaa cgaccttttgg ccgctgtggg atctcatcac cgaagagcat    120
gtcgcgctgg tggtcgcggg cgaaatcgat tacgcgacca tgcattacaa gcgtacggaa    180
tgtttcctcg ccgagatcgg cattttggcc gacgaacagc aggtcagcgg cttcgaaaga    240
cgtcgtcgtg aaattctcac ccgttcgtgg caattgttcg aagatgtcct cccatgcctt    300
gaatggctgc gggccgccgg tgttctcgtc gccgcggtca cgaacgcctc gggcgcgcat    360
cagcgcaaga gatcgccga cctcggcctc gcccggttct cgatcacgt ggccatcgcc    420 ggtgaactcg gagtagccaa acccgacccg gcgatgttcc actcggtctg cctcggcctc    480
ggctgcgacc cggcgcaggc cgtccacgtc ggcgacaaac tcgacaccga cgccatcggc    540
gcgcgcgacg ccggcctggg ggccgtctgg ctcgaccggg acggcatcgc cgagcgcgcc    600
ccggcgggcg tgcacaccat ctcgggcctc gacgagctgc ctgagctgct cgtttccgag    660
ttcgcgaagc tcggcgtgcc cgctcagcgc gctactgaga ccccgctttt cacggtgcgg    720
aacagcgtgc tctag                                                     735
```

```
<210> SEQ ID NO 9
<211> LENGTH: 70
<212> TYPE: PRT
<213> ORGANISM: Amycolatopsis japonicum
<220> FEATURE:
<223> OTHER INFORMATION: ORF 1643

<400> SEQUENCE: 9

Met Val Glu Gly Arg Gln Thr Thr Pro Ala Thr Phe Asp His Pro Leu
1               5                   10                  15

Val Thr Ser Gly Ser Arg Leu Asn Asp Gly Gly Val Val Val Glu His
            20                  25                  30

Gly Phe Ala Gly Ala Gly Ala Gly Leu Thr Leu Ser Val Ala Ala Ile
        35                  40                  45

Ala Thr Ile Pro Ala Ala Phe Asp Ala His Val Pro Val Thr Pro Val
    50                  55                  60

Leu Lys Ala Glu Thr Ala
65                  70

<210> SEQ ID NO 10
<211> LENGTH: 213
<212> TYPE: DNA
<213> ORGANISM: Amycolatopsis japonicum
<220> FEATURE:
<223> OTHER INFORMATION: orf 1643

<400> SEQUENCE: 10
gtggttgaag gccgccagac gacaccagcc accttcgacc accgctggt gacttccgga        60 agccggctga acgacggcgg cgtggtggtc gaacacggtt cgccgggc cggggccggc        120 ctcacgctct ccgtcgccgc gatcgccacc atccccgccg ccttcgacgc acacgtcccg      180
gtcactccgg tactcaaagc ggagaccgct tag                                    213

<210> SEQ ID NO 11
<211> LENGTH: 135
<212> TYPE: PRT
<213> ORGANISM: Amycolatopsis japonicum
<220> FEATURE:
<223> OTHER INFORMATION: ORF 1644

<400> SEQUENCE: 11

Met Arg Gln Ala Gly Phe Asp Gly Glu Leu Pro Asp Arg Ile Arg Ala
1               5                   10                  15

Phe Asp Glu Ile Val Lys Thr His Glu Trp Ser Glu Ser Ala Gly Ser
            20                  25                  30

Ile Thr Gln Pro Ile Asp Tyr Tyr Arg Gln Phe Arg Gly Arg Pro Glu
        35                  40                  45

Gly Pro Asn Arg Val Tyr Asp Ala Ser Asp Leu Pro Gly Val Gly Tyr
    50                  55                  60

Thr Arg Gln Val Ala Asp Thr Thr Arg Met Gly Leu Gly Glu Ser Trp
65                  70                  75                  80

Thr Glu Ala Gly Gln Pro Val Arg Glu His Pro Glu Pro Ser Ser Asp
                85                  90                  95

Leu Phe Thr His Thr Ser Gly Pro Asn Gln His Ala Leu Ile Thr Glu
            100                 105                 110

Gln Leu Thr Arg His His Tyr Val Met Thr Leu Thr Met Ser Thr Arg
        115                 120                 125

Gln Thr Tyr Pro Thr Cys Arg
    130                 135
```

<210> SEQ ID NO 12
<211> LENGTH: 408
<212> TYPE: DNA
<213> ORGANISM: Amycolatopsis japonicum
<220> FEATURE:
<223> OTHER INFORMATION: orf 1644

<400> SEQUENCE: 12

```
gtgcggcaag caggcttcga cggcgaactg cctgaccgga tccgagcttt cgacgagatc      60
gtcaagacac acgagtggtc tgaaagtgca ggctcgatca cacaacccat cgactactac     120
cgccagttcc ggggtcgccc ggaaggaccg aaccgggtct acgacgcgag cgacctcccc     180
ggcgtcggct acacccggca ggtggccgac accacccgca tgggactcgg cgagtcctgg     240
accgaagcgg acagccggt acgggagcac cccgagccgt cgtcagacct tttcacccat     300
accagcggac cgaaccagca tgccttgatc accgagcagc tgacccgaca ccattacgtg     360
atgaccttga ccatgagcac caggcagacc tatccgacgt gtcggtga                 408
```

<210> SEQ ID NO 13
<211> LENGTH: 325
<212> TYPE: PRT
<213> ORGANISM: Amycolatopsis japonicum
<220> FEATURE:
<223> OTHER INFORMATION: ORF 1645

<400> SEQUENCE: 13

Met Thr Met Arg Ala Ala Tyr Leu Ala Glu Pro Gly Val Val Ala Val
1               5                   10                  15

Gly Arg Phe Pro Ile Pro Arg Pro Glu Gly Gln Val Leu Val Glu
            20                  25                  30

Met Arg His Ala Ser Ile Cys Gly Ser Asp Val His Ile Val Phe Asp
        35                  40                  45

Gly Phe His Asp Gln Glu Arg Leu Gly Ser Pro Gly Tyr Pro Gly His
    50                  55                  60

Glu Gly Ile Gly Val Val Ala Glu Ser Arg Ser Arg Ala Phe Ala Ala
65                  70                  75                  80

Gly Asp Pro Val Leu Thr Val Pro Pro Val Glu His Thr Gly Cys Phe
                85                  90                  95

Ala Glu Tyr Gln Val Val Asp Glu Gly Ser Leu Val Pro Val Pro Arg
            100                 105                 110

Glu Gly Asp Leu Ser Arg Leu Leu Leu Ala Gln Gln Leu Gly Thr Thr
        115                 120                 125

Val Phe Gly Met Ala Lys Phe Val Asp Gly Pro Pro Arg Thr Ala
    130                 135                 140

Ala Val Ile Gly Ala Gly Ser Ala Gly Leu Phe Phe Leu Gln Leu Leu
145                 150                 155                 160

Arg Arg Met Gly Cys Glu Ser Val Leu Val Ser Asp Leu Asp Pro Gly
                165                 170                 175

Arg Leu Val Val Ala Asp Arg Leu Gly Ala Gln Val Val Asp Ala Arg
            180                 185                 190

Arg Ala Ala Leu Ala Asp Thr Ala Arg Glu Met Thr Gly Gly Ile Gly
        195                 200                 205

Val Asp Leu Val Val Glu Ala Ala Gly Pro Asp Ala Cys Arg Val Glu
    210                 215                 220

Ala Val Glu Ala Val Arg Glu Arg Gly Thr Ile Gly Phe Phe Gly Phe
225                 230                 235                 240

```
Pro Glu Arg Lys Gly Thr Ala Pro Phe Pro Val Glu Arg Ala Phe Arg
            245                 250                 255

Lys Ser Val Arg Met Glu Trp Val Asn Gly Thr Gln Lys Glu Pro Gly
        260                 265                 270

Leu Val Ser Phe Arg Arg Ala Val Asp Leu Ile Arg Ser Gly Glu Ile
    275                 280                 285

Val Val Asp His Cys Leu Glu His Ala Phe Asp Leu Gly Asp Ile Ala
290                 295                 300

Glu Ala Phe Ala Ser Ala Arg Arg His Gly Asp Gly His Pro Lys Val
305                 310                 315                 320

Gly Ile Ile Leu Arg
            325

<210> SEQ ID NO 14
<211> LENGTH: 978
<212> TYPE: DNA
<213> ORGANISM: Amycolatopsis japonicum
<220> FEATURE:
<223> OTHER INFORMATION: orf 1645

<400> SEQUENCE: 14
atgaccatgc gggcggcata tctggcagag cccggagtgg tcgcggtcgg gcggttcccg      60
ataccgcgcc ccgaggaagg gcaagtgctc gtcgaaatgc ggcacgcctc gatctgcggc     120
tcggacgtgc acatcgtgtt cgacggcttc acgatcaag agcggttggg cagccctggc      180
tatccagggc acgagggcat cggagtggtg gcggaaagcc gcagccgagc cttcgccgcc     240
ggcgatcctg tgctcaccgt gccgcctgtg aacacaccg ttgcttcgc cgaataccag       300 gtcgtcgacg aggggagcct ggtaccggtt ccgcgcgagg cgacctgtc ccgcctgctg      360 ctcgcacaac aactcgggac cacgtgttc gggatggcga aattcgtcga cggaccccca      420
ccccggaccg cggccgtgat cggtgcgggc tccgcgggat tgttcttctt gcagttgctg     480
cgccgcatgg gatgtgagtc cgtgctcgtg tcggacctcg atcccggcag gctcgtcgtc     540
gcggaccggc tgggcgcaca gtggtcgac gcacgacgag cggctctcgc ggacacggca     600
cgcgagatga ccggcggtat cggcgtggac ctcgtcgtcg aagccgccgg gcccgacgcc    660
tgcagggtgg aggcggtcga agccgtccgg gagcgcggca cgatcgggtt cttcggcttc    720
cccgaacgca agggcacggc cccgttcccg gtggagcggg cattccgcaa gtcggtacgg    780
atggaatggg tcaacggaac gcagaaggaa ccgggcctgg tgtcgttccg gcgagccgtg    840
gatctgatcc gaagcggcga gatagtggtc gaccattgcc tcgagcacgc cttcgacctc    900
ggagacatcg ccgaggcgtt cgcgtccgcc cgccgccacg gtgatggcca cccgaaggtg    960
ggaatcattc tgcgctga                                                   978

<210> SEQ ID NO 15
<211> LENGTH: 448
<212> TYPE: PRT
<213> ORGANISM: Amycolatopsis japonicum
<220> FEATURE:
<223> OTHER INFORMATION: ORF 1646

<400> SEQUENCE: 15

Met Asn Trp Ser Gln Leu Leu Val Pro Val Thr Ser Gly Val Ser Val
1               5                   10                  15

Ala Leu Ile Val Ala Thr Val Arg Phe Leu Trp Arg Arg Thr Arg Leu
            20                  25                  30

Pro Thr Gly Leu Ser Gln Arg Met Thr Arg Arg Asn Tyr Leu Ala Glu
```

```
                35                  40                  45
Met Leu Val Ile Ser Lys Asn Asp Asn Val Asp Arg Leu Asp Ala Leu
 50                  55                  60

Val Pro Asn Leu Leu Pro Ala Gln Gly Ser Pro Val Leu Val Glu Ile
 65                  70                  75                  80

Gln Glu Ser Trp Thr Gln Ile Asn Gly Arg Gly Val Arg Val Ile
                 85                  90                  95

Thr Arg Thr Glu Pro Ala Ser Leu Thr Ala Gly Ala Glu Leu Leu Ala
                100                 105                 110

Ala Gly Ile Glu Val Arg Val Ser Arg Ala Leu Thr Ala Asp His Leu
            115                 120                 125

Ser Tyr His Leu Phe Ser Gly Ser Glu His His Thr Val Leu Asn Arg
        130                 135                 140

Arg Asn Gly Gly Lys Asp Arg Pro Glu Arg Leu Asp Glu Ile Ser Ala
145                 150                 155                 160

Ala Lys Val Phe Arg Ser His Phe Asp Glu Thr Trp Ser Glu Ser Glu
                165                 170                 175

Pro Ile Glu Ser Phe Leu Ala Gly Gln Leu Leu Ala Gly Pro Asp Ser
            180                 185                 190

Gly Leu Ala Asp Arg Ile Arg Glu Gln Arg Ala Ala Tyr Gln Leu Pro
        195                 200                 205

Ala Lys Ala Glu Asp Ala Ile Leu Arg His Leu Ala Phe Arg His Arg
210                 215                 220

Ala Pro Val Val Phe Val Thr Gly Leu Pro Gly Ala Gly Lys Ser Leu
225                 230                 235                 240

Val Arg Arg Ala Leu Ala Glu Glu Leu Arg Arg Trp Arg Met Gln Val
                245                 250                 255

Asp Glu Leu Asn Asp Tyr Val Tyr Ala Phe Glu Glu Phe Leu His Ala
            260                 265                 270

Leu Met Leu Leu Gly Asp Gly Arg Gly Ala Gly Phe Ser Ala Gln Gln
        275                 280                 285

Gly Gly Ala Phe Gln Val Glu Arg Glu Asp Asp Leu Arg Pro Ala Leu
    290                 295                 300

His Thr Leu Gly His Arg Val Trp Glu Asn Arg Arg Ser Asn Pro Ile
305                 310                 315                 320

Thr Ile Val Glu Phe Ala Arg Ala Asp Thr Ile Gly Ala Leu Gln Val
                325                 330                 335

Phe Gly Asp Glu Val Leu Ala Ala Ser Gln Ile His Val Arg Ala
            340                 345                 350

Ser Asp Thr Glu Arg Ser Ala Arg Leu Ala Arg Arg Gly Glu Pro Pro
        355                 360                 365

Lys Ile Ser Val Ala Gly Gln Ser Ile Ser Leu Glu Val Ser Asp Glu
    370                 375                 380

His Arg Leu Pro Ser Asn Ala Ala Asp Thr Leu Tyr Ser Arg Asp Asp
385                 390                 395                 400

Phe Ala Leu Leu Lys Ala Gln Lys Asn Ile Ala Asn Arg Leu Phe Leu
                405                 410                 415

Val Glu Asn Asp Ala Glu Glu Lys Ala His Val Asp Glu Gln Val Thr
            420                 425                 430

Ala Phe Val Glu Ala Val Val Arg Pro Tyr Arg Val Leu Ala Arg Thr
        435                 440                 445

<210> SEQ ID NO 16
```

<211> LENGTH: 1347
<212> TYPE: DNA
<213> ORGANISM: Amycolatopsis japonicum
<220> FEATURE:
<223> OTHER INFORMATION: orf 1646

<400> SEQUENCE: 16

| | | | |
|---|---|---|---|
| atgaactgga gtcagctcct cgttcccgtg accagcggtg tgtccgtcgc cctcatcgtg | 60 |
| gcgaccgtca ggttcctgtg gcggcgcacc cgtctgccga ccggcctctc ccagcggatg | 120 |
| acccggcgga actacctggc ggagatgctc gtcatctcca agaacgacaa cgtcgaccgg | 180 |
| ctcgacgcac tggtcccgaa tctgctgccg gcacaaggct cccccgtgct cgtcgagatc | 240 |
| caggagtcgt ggacgcagat caacggccgg cgcggcgtcc gggtgatcac ccggaccgag | 300 |
| cccgcgtccc tgaccgccgg agccgagttg ctcgcagcgg ggatcgaggt tcgcgtgtcc | 360 |
| cgcgcactga ccgcggatca cctgtcgtac cacctgttct ccggttcgga acaccacacg | 420 |
| gtgctcaacc gccgcaacgg cgggaaggac cggcccgaac gactggacga gatctccgca | 480 |
| gccaaggtgt tccgcagcca cttcgacgag acgtggagcg agtccgaacc catcgaatcg | 540 |
| ttcctggccg ggcaactcct ggccgggccc gactccggcc tcgcggaccg gatccgggag | 600 |
| cagcgcgcgg cgtaccagct gcccgccaag gcggaggacg cgatcctgcg gcatctggcg | 660 |
| ttccgccacc gggcgccggt cgtcttcgtc accggcctgc cgggtgccgg caagtcactg | 720 |
| gttcgacgag ctctcgccga agagcttcgg cggtggcgga tgcaggtcga cgagctgaac | 780 |
| gactacgtct acgcgttcga ggaattcctc cacgccttga tgctcctcgg cgacggtcgc | 840 |
| ggtgccggct tcagcgccca gcagggcggc gcgttccagg tggagcgcga ggacgatctc | 900 |
| cggcccgccc tgcacacgct cggccaccgc gtctgggaaa accgccggag caacccgatc | 960 |
| acgatcgtcg agttcgccag ggccgacacg atcggagcgc tccaggtgtt cggcgacgag | 1020 |
| gtactggcgg cgtcgcagat catccacgtc cgcgcctccg acaccgagcg ctccgcccgg | 1080 |
| ctggccagac ggggcgaacc accgaagatc tcggtggcgg gtcagtcgat cagtctcgaa | 1140 |
| gtgtccgacg agcatcggct gcccagcaac gccgcggaca ccctgtacag cagggatgac | 1200 |
| ttcgcactcc tgaaggcaca gaagaacatc gccaaccgcc ttttcctcgt cgagaacgac | 1260 |
| gccgaggaaa aggcgcacgt cgacgaacag gtcacggcgt tcgtcgaggc ggtcgtgcgc | 1320 |
| ccctaccgag tactcgcgcg tacctag | 1347 |

<210> SEQ ID NO 17
<211> LENGTH: 110
<212> TYPE: PRT
<213> ORGANISM: Amycolatopsis japonicum
<220> FEATURE:
<223> OTHER INFORMATION: ORF 1647

<400> SEQUENCE: 17

Met Thr Glu Gln Ala Phe Phe Val Leu Thr Ala Leu Val Asp Thr Pro
1               5                   10                  15

Arg His Gly Tyr Gly Ile Val Gly Glu Val Ser Gly Leu Ser Asp Gly
            20                  25                  30

Arg Val Lys Leu Lys Val Gly Thr Leu Tyr Gly Val Leu Asp Arg Leu
        35                  40                  45

Val Ala Asp Gly Leu Val Glu Pro Asp Arg Glu Glu Val Ala Asn Gly
    50                  55                  60

Arg Leu Arg Arg Tyr Tyr Arg Leu Thr Glu Asp Gly Arg Thr Ala Leu
65                  70                  75                  80

```
Ala Ala Glu Val Gln Arg Gln Ala Ser Asn Ala Arg Ala Ser Glu
             85                  90                  95

Arg Leu Arg Ala Trp Arg Pro Ala Asp Thr Gly Gly Leu Ala
        100                 105                 110
```

<210> SEQ ID NO 18
<211> LENGTH: 333
<212> TYPE: DNA
<213> ORGANISM: Amycolatopsis japonicum
<220> FEATURE:
<223> OTHER INFORMATION: orf 1647

<400> SEQUENCE: 18

```
atgacggagc aggcgttctt cgtgctcacc gcgctggtgg acacgccgcg gcatgggtac      60
gggatcgtcg gcgaggtgag cggtctctcg gacggccggg tgaagctgaa ggtcggcacg     120
ctgtacggcg tgctggatcg gctggtcgcg gacggtttgg tcgagccgga tcggaggag      180 gtcgccaacg gcggctccg ccggtactac cggctgaccg aggacggccg cacggcgctc     240
gcggccgagg tccaacggca ggcctcgaac gcccgcgccg cctcggaacg gctgcgcgcg     300
tggcggccgg cggacaccgg gggcctggcg tga                                  333
```

<210> SEQ ID NO 19
<211> LENGTH: 331
<212> TYPE: PRT
<213> ORGANISM: Amycolatopsis japonicum
<220> FEATURE:
<223> OTHER INFORMATION: ORF 1648

<400> SEQUENCE: 19

```
Met Asn Arg Leu Glu Glu Arg Tyr Arg Arg Val Leu Arg Leu Pro
1               5                   10                  15

Ala Ser Tyr Arg Gln Ala Trp Glu Glu Asp Met Val Ala Thr Phe Leu
                20                  25                  30

His Ser Glu Met Pro Glu Asp Ala Glu Asp Ala Glu Phe Ala Val Asp
            35                  40                  45

His Gly Arg Pro Ser Trp Pro Glu Val Ala Ser Val Val Ala Leu Ala
        50                  55                  60

Val Arg Leu Arg Leu Gly Gly Asp Gly Ala Pro Leu Arg Tyr Leu Val
65                  70                  75                  80

Trp Gly Glu Thr Val Arg Arg Leu Ala Leu Val Gly Leu Leu Val Gln
                85                  90                  95

Ala Val Ala Ala Leu Val Gly Ile Gly Ala Trp Leu Trp Ser Pro Ser
            100                 105                 110

Val Thr Asn Pro Ile Pro Ala Asp Val Gln Thr Leu Leu Gly Leu Val
        115                 120                 125

Trp Val Ala Ala Tyr Leu Cys Leu Val Thr Gly Arg Arg Arg Ala Ala
    130                 135                 140

Arg Trp Leu Ala Val Thr Ala Leu Ala Gln Ala Ser Val Phe Phe Gly
145                 150                 155                 160

Val Asp Leu Val Ala Val Glu Gly Ala Tyr Gly Leu Ser Gly Thr Val
                165                 170                 175

Gly Leu Leu Leu Glu Ala Leu Pro Val Val Ala Leu Val Ala Phe His
            180                 185                 190

Arg Gln Ala Pro Pro Val Lys Ala Arg Pro Trp Leu Val Ala Leu Leu
        195                 200                 205

Ala Gly Val Gly Leu Leu Thr Val Ala Met Ser Val Thr Tyr Val Ser
    210                 215                 220
```

Val Pro Ala Leu Val Asp Trp Pro Gly Val Asp Cys Ala Ala Val Phe
225                 230                 235                 240

Val Ala Ala Val Val Tyr Leu Ser Val Pro Arg Leu Gly Trp Arg Ser
            245                 250                 255

Ala Ala Val Ser Trp Ser Thr Thr Leu Ala Ser Leu Ala Leu Val Ala
        260                 265                 270

Leu Val Gln Arg Val Val Thr Leu Leu Asp Tyr Leu Arg Leu Ala Ala
    275                 280                 285

Arg Thr Ala Glu Leu Asp Ile Met Ile Ala Ile Ala Ala Gly Gln Thr
290                 295                 300

Val Ala Val Leu Ala Ile Ser Val Pro Leu Ala Met Leu Ala Val Lys
305                 310                 315                 320

Ala Val Arg Ala Leu Pro Pro Val Ala Ala Arg
                325                 330

<210> SEQ ID NO 20
<211> LENGTH: 996
<212> TYPE: DNA
<213> ORGANISM: Amycolatopsis japonicum
<220> FEATURE:
<223> OTHER INFORMATION: orf 1648

<400> SEQUENCE: 20
gtgaaccgcc tggaggagcg gtaccggcgg gtgctgcggc tgctccccgc ctcctatcgt      60
caggcgtggg aggaggacat ggtcgccacc ttcctgcaca gcagatgcc ggaggacgcc     120 gaggacgcg agttcgccgt cgaccacggc aggccgagct ggccggaggt ggcgagcgtc     180
gtggcgctgg cggtgcggct gcggctggga ggcgacggcg cgcccctccg ctacctcgtg     240
tggggtgaga cggtccggcg gctggcgctg gtggggttgc tcgtgcaggc ggtggccgcg     300
ctggtcggta tcggggcgtg gctgtggtct ccctcggtga cgaatccgat cccggccgac     360
gtgcagaccc tgctcggctt ggtctgggtg cggcttatc tgtgcctggt gaccggcagg     420
cggcgcgcgg cgcggtggct cgcggtgacg cgctggctc aagcctcggt cttcttcggc     480
gtggatctcg tggccgtcga gggcgcgtac gggctgtccg gaccgtcgg actcctgctg     540 gaggcgctgc cggtggtggc actggtcgcg ttccatcggc aggccccacc ggtgaaagcg     600
cggccgtggc tcgtcgcgct gcttgccggt gtcggcctcc tgacggtcgc gatgtcggtc     660
acctatgtca gcgttccggc gctcgtggac tggccgggcg tggactgtgc ggcggttttc     720
gtcgccgcgg tcgtctactt gagcgtgcct cgcctgggct ggcggagtgc gcgcggtgtcg     780 tggtcgacga cgctcgcttc gctcgcgctg gtcgccctcg tgcagcgggt cgtgacgctg     840
ctggactacc tccggctcgc ggcccgcacc gcggaactgg acatcatgat cgcgatcgcc     900
gccgggcaga ccgtggcggt tctggcgata tcggtgccgc tcgcgatgct cgccgtcaag     960
gccgtgcgcg cgctgccgcc ggtggctgcc cggtga                               996

<210> SEQ ID NO 21
<211> LENGTH: 339
<212> TYPE: PRT
<213> ORGANISM: Amycolatopsis japonicum
<220> FEATURE:
<223> OTHER INFORMATION: ORF 1649

<400> SEQUENCE: 21

Met Val Leu Ala Leu Pro Phe Val Asp Gln Val Trp Gln Ile Tyr Val
1               5                   10                  15

```
Leu Ile Val Ile Leu Gln Ser Ala Ser Ala Ser Phe Thr Pro Ala Phe
         20                  25                  30

Gln Ala Val Leu Pro Asp Leu Leu Pro Asp Glu Arg Asp Tyr Thr Lys
     35                  40                  45

Ala Leu Ser Leu Ser Gln Leu Ala Ser Thr Met Glu Ser Leu Leu Ser
 50                  55                  60

Pro Leu Leu Ala Ala Ala Val Leu Ser Leu Val Ser Phe His Trp Leu
 65                  70                  75                  80

Phe Thr Gly Thr Ser Leu Gly Phe Ala Ala Ser Ala Ala Leu Val Leu
                 85                  90                  95

Ser Thr Arg Ile Pro Asp Ala Ala Arg Gly Asp Arg Gly Gly Ala Trp
            100                 105                 110

Asp Arg Thr Met Ala Gly Ile Lys Met Tyr Leu Ala Thr Pro Arg Leu
            115                 120                 125

Arg Gly Thr Leu Gly Leu Asp Leu Val Val Ala Ala Ala Gly Ser Val
        130                 135                 140

Val Met Val Asn Thr Val Asn Tyr Val Arg Asp Thr Leu Gly Gly Thr
145                 150                 155                 160

Gln Ser Asp Val Ala Leu Leu Ala Ala Asn Gly Ala Gly Thr Ile
                165                 170                 175

Leu Ala Ala Leu Leu Leu Pro Arg Val Leu Asp Gly Ile Pro Asp Arg
                180                 185                 190

Thr Val Met Leu Thr Gly Gly Thr Leu Leu Ala Gly Leu Thr Gly
            195                 200                 205

Ala Ile Ala Leu Ser Thr Val Glu His Gly Ala Ala Ala Pro Val Val
        210                 215                 220

Trp Ala Val Ile Gly Leu Gly Thr Gly Leu Val Leu Thr Pro Val Gly
225                 230                 235                 240

Arg Val Leu Arg Arg Ser Ser Arg Pro Ala Asp Arg Pro Ala Ile Phe
                245                 250                 255

Ala Ala Arg Phe Ser Leu Ser His Ala Cys Trp Leu Leu Ala Tyr Pro
                260                 265                 270

Ile Ala Gly Arg Leu Ala Thr Asp Ala Gly Phe Thr Val Thr Trp Leu
            275                 280                 285

Val Leu Gly Ala Leu Gly Val Ile Gly Leu Val Thr Ala Val Arg Ala
        290                 295                 300

Trp Pro Arg Asn Asp Asp Glu Asp Arg Pro Arg Pro Lys Ser Arg Pro
305                 310                 315                 320

Gly Gln Pro Phe Glu Asp Ile Thr Gly Gln Pro Pro Ala Ala Ala Arg
                325                 330                 335

Ala Arg Pro

<210> SEQ ID NO 22
<211> LENGTH: 1020
<212> TYPE: DNA
<213> ORGANISM: Amycolatopsis japonicum
<220> FEATURE:
<223> OTHER INFORMATION: orf 1649

<400> SEQUENCE: 22
gtggtgctcg ccctgccctt cgtcgaccag gtctggcaga tctacgtcct gatcgtgatc       60
ctccagtccg cgtcggcctc gttcaccccg gcgttccagg ccgtgctccc cgatctcctt      120
cccgacgaac gcgactacac gaaggcactg tcgctgtccc agctggcttc gacgatggag      180
agcctcctca gtccgctcct ggccgccgcc gtgctcagtc tcgtgtcctt ccactggctg      240
```

```
ttcaccggca cttcgctcgg tttcgcggcc tccgccgcac tggtgctgag cacccggatc    300
ccggacgcgg cgcgcggcga ccgcggcggg gcctgggatc gcaccatggc cgggatcaag    360
atgtacctcg cgaccccgcg cctgcggggc accctcggcc tcgacctggt ggtcgcggcg    420
gccggctccg tggtcatggt caataccgtg aactacgtcc gagacaccct cggcggaaca    480
cagtccgacg tcgccctgct cctggcggcc aacggcgccg gcaccatcct ggccgcgctc    540
ctgctccccc gtgtactcga cgggatcccc gaccgcaccg tcatgctcac cggcggcgga    600
accctgctcg ccggactgac cggcgccatc gcactgtcca cagtggagca cggggccgcg    660
gcgccggtcg tatgggccgt catcgggctc ggcaccgggc tcgtcctcac tcccgtcggc    720
cgggtactgc gcagatccag ccgtcccgcc gaccggcccg cgatcttcgc cgcccggttc    780
tccctttccc acgcctgctg gctactcgcc tacccgatcg ccggacggct cgccaccgac    840
gccgggttca ccgtcacctg gctcgtcctc ggcgcactcg gcgtcatcgg cctcgtcacg    900
gccgtccgcg cgtggccacg aaacgacgac gaggaccgac cgcggccgaa atcccggcca    960
ggtcaaccct tcgaggacat caccgggcag ccaccggcgg cagcgcgcgc acggccttga   1020
```

<210> SEQ ID NO 23
<211> LENGTH: 103
<212> TYPE: PRT
<213> ORGANISM: Amycolatopsis japonicum
<220> FEATURE:
<223> OTHER INFORMATION: ORF 1650

<400> SEQUENCE: 23

```
Met Ser Leu Phe Gly His Arg Asp Tyr Arg His Leu Phe Gly Ala Gln
1               5                   10                  15

Leu Val Ala Leu Phe Gly Thr Gly Leu Thr Thr Val Ala Leu Gly Leu
            20                  25                  30

Leu Ala Tyr Asp Leu Ala Gly Ser Asp Ala Gly Ala Val Leu Gly Thr
        35                  40                  45

Ala Leu Ala Ile Lys Met Ile Thr Tyr Val Thr Val Ala Pro Leu Ala
    50                  55                  60

Val Ala Tyr Ala Ala Thr Gly Cys Arg Ala Val Ser Ser Ser Ser Arg
65                  70                  75                  80

Trp Thr Arg Ser Ala Arg Trp Trp Cys Ser Pro Cys Pro Ser Ser Thr
                85                  90                  95

Arg Ser Gly Arg Ser Thr Ser
            100
```

<210> SEQ ID NO 24
<211> LENGTH: 312
<212> TYPE: DNA
<213> ORGANISM: Amycolatopsis japonicum
<220> FEATURE:
<223> OTHER INFORMATION: orf 1650

<400> SEQUENCE: 24

```
atgtcgctgt tcggtcatcg tgactatcgg catctgttcg gggcgcagct ggtcgcgctg     60
ttcggcactg gattgacgac cgtagcgctc gggctgctgg cctacgactt ggcggggtcc    120
gacgcgggcg ccgtcctggg caccgcgctg gccatcaaga tgatcaccta cgtcacggtg    180
gcgccgctcg ccgtcgcgta cgccgcgacc gggtgccgcg ccgtttcttc ctcgtcacgc    240
tggacgcgat ccgcgcgctg gtggtgctcg ccctgcccct cgtcgaccag gtctggcaga    300
tctacgtcct ga                                                        312
```

<210> SEQ ID NO 25
<211> LENGTH: 116
<212> TYPE: PRT
<213> ORGANISM: Amycolatopsis japonicum
<220> FEATURE:
<223> OTHER INFORMATION: ORF 1651

<400> SEQUENCE: 25

```
Met Tyr Ala His Asp Glu Ser Gly Gly Gln Trp Ser Arg Leu Pro Pro
1               5                   10                  15

Asp Asp Gln Ile Glu Ala Ala Ser Thr Ala Leu Arg Met Leu Ala Asp
            20                  25                  30

Pro Thr Arg Met Arg Met Leu Trp Leu Ile Ser Gly Glu Glu Tyr Asp
        35                  40                  45

Val Ala Ser Leu Ala Ala Ala Val Gly Ile Ala Arg Pro Ala Val Ser
    50                  55                  60

Gln His Leu Ala Lys Leu Lys Leu Ala Gly Leu Val Thr Gln Arg Arg
65                  70                  75                  80

Asp Gly Arg Arg Ile Leu Tyr Arg Ala Arg Gly Gly His Val Arg Arg
                85                  90                  95

Leu Leu Ala Glu Val Met Asn Ala Ala Asp His His Leu His Gly Ile
            100                 105                 110

Pro Asp His Asp
        115
```

<210> SEQ ID NO 26
<211> LENGTH: 351
<212> TYPE: DNA
<213> ORGANISM: Amycolatopsis japonicum
<220> FEATURE:
<223> OTHER INFORMATION: orf 1651

<400> SEQUENCE: 26

```
atgtacgcac atgacgaatc aggcggccaa tggtcccggc tgccgccgga cgaccagatc      60
gaagccgcgt ccacggcgtt gcggatgctc gcggatccca cccggatgcg gatgctgtgg     120
ctgatcagcg gcgaggagta cgacgtcgcg tcactggcgg ccgcggtggg catcgcgcgt     180
ccggcggtgt cccagcatct ggccaagctc aagctggccg gattggtcac ccagcgcagg     240
gacggccgcc ggatcctta ccgggcccgc ggcgggcacg tccggaggct gctggcggag     300
gtcatgaacg cggccgatca ccaccttcac gggatccccg accacgactg a             351
```

<210> SEQ ID NO 27
<211> LENGTH: 375
<212> TYPE: PRT
<213> ORGANISM: Amycolatopsis japonicum
<220> FEATURE:
<223> OTHER INFORMATION: ORF 1652

<400> SEQUENCE: 27

```
Met Asp Gly Pro Asp Ala Thr Arg Ser Leu Leu Pro Ala Gly Phe Gln
1               5                   10                  15

Arg Tyr Gly Arg Thr Lys Ala Thr Ala Ala Ala Gly Asp Asp Leu
            20                  25                  30

Leu Asp Ile Ile Gly Leu Ser Glu Thr Asp Val Glu Val Tyr Asp Ala
        35                  40                  45

Phe Ala Gly Thr Gly Ser Leu Thr Val Ala Glu Ile Arg Arg Arg Thr
    50                  55                  60
```

Gly Ile Pro Gln Gln Arg Leu Leu Arg Val Leu Gly Ala Leu Thr Glu
65                  70                  75                  80

Lys Gly Leu Leu Val Arg Leu Pro Gly Arg Ala Glu Val Tyr Ser Ala
            85                  90                  95

Val Arg Pro Glu Ile Ala Leu Glu Ala Met Leu Arg Leu Lys Glu Gln
        100                 105                 110

Glu Leu Ala Ser Ala Arg Leu Val Ala Asp Arg Leu Arg Glu Arg Tyr
    115                 120                 125

Arg Ala Thr Ser Gly Glu Arg Ala Val Asp Leu Ile Glu Val Ile His
130                 135                 140

Gly Asp Ala Leu Ile Ala Glu Arg Ala Asp Gln Leu Leu Arg Ser Ala
145                 150                 155                 160

Glu Arg Glu Val Ala Phe Val Asp Lys Pro Pro Tyr Ala Arg Thr Pro
                165                 170                 175

Ser Val Leu His Pro Ala Glu Arg Asp Leu Leu Gly Arg Gly Val Arg
            180                 185                 190

Phe Arg Gly Val Tyr Glu Arg Ser Ala Leu Glu Met His Asp Leu Ser
        195                 200                 205

Ser Asp Leu Glu Ala Gly Leu Ala Leu Gly Glu Glu Ala Arg Val Val
    210                 215                 220

Thr Ser Ala Pro Leu Lys Met Ile Val Val Asp Gln Arg Val Gly Leu
225                 230                 235                 240

Val Pro Leu Arg Ser Asp Arg Pro Glu Val Gly Ala Ala Leu Val Ile
                245                 250                 255

His Pro Cys Ala Leu Leu Asp Ala Leu Gly Ala Val Phe Ala Phe Leu
            260                 265                 270

Trp Gln Ser Gly Leu Pro Leu Arg Leu Pro Gly Ser Ala Glu Leu Ala
        275                 280                 285

Asp Val Ala Pro Ser Asp Ala Arg Leu Leu Ala Leu Leu Thr Thr
    290                 295                 300

Gly Leu Pro Asp Arg Ser Ile Ala Lys Gln Leu Gly Met Ser Tyr Arg
305                 310                 315                 320

Thr Phe Gln Arg Arg Leu Arg Asp Leu Met Thr Ala Leu Gly Ala Thr
                325                 330                 335

Thr Arg Phe Gln Ala Gly Leu Gln Val Ala Thr Arg Gly Trp Val Thr
            340                 345                 350

Leu Pro Ser Thr Gln Pro Pro Ile Glu Asp Asp Val Ser Glu Arg Ala
        355                 360                 365

Gly Ser Pro Ser Pro Arg Pro
370                 375

<210> SEQ ID NO 28
<211> LENGTH: 1128
<212> TYPE: DNA
<213> ORGANISM: Amycolatopsis japonicum
<220> FEATURE:
<223> OTHER INFORMATION: orf 1652

<400> SEQUENCE: 28
gtggacggtc cggacgcgac gcggtccctt tgcccgccg gattccagcg gtatggtcgg      60
acgaaggcga ccgcggctgc ggcgggagac gatttgctgg acatcatcgg tctgagtgaa     120
accgacgtcg aggtctacga tgccttcgcc ggcaccggtt cgctgaccgt cgccgaaatc     180
cggcggcgaa ccgggattcc gcaacaacgg ctgctgcgcg tactgggcgc gctgacggaa     240
aaaggtttgc tcgtcaggct tcccggccgg gcggaggtgt attcggcggt gcggccggag     300

```
atcgcgctgg aggcgatgct ccggctgaag gaacaggaac tcgcgagcgc gcggctggtc     360
gccgaccggt tgcgcgagcg gtaccgggcg acgtccggcg aacgcgcggt cgatctcatc     420
gaagtgatcc acggcgacgc gctgatcgcc gagcgggcgg atcagctgct gcgctcggcc     480
gagcgggagg tcgccttcgt cgacaaaccg ccttacgcgc gaacgccgag tgtgctgcat     540
cccgccgaac gtgatctcct cggccggggg gtgcgctttc gcggggttta cgagcgcagt     600
gcgctggaaa tgcacgacct gtcatccgac ctggaggcag gcctcgcgct cggcgaggag     660
gcccgcgtgg tcaccagcgc cccgctcaag atgatcgtgg tcgaccagcg cgtcggactg     720
gtaccactgc ggtccgatcg ccccgaggtc ggcgcggcct ggtgatccaa cccgtgcgca     780
ctgctcgacg cgctcggcgc ggtcttcgct ttcctttggc agagcgggct ccgctgcgc     840 ctgcccggtt cggccgaact ggcggacgtc gcccttccg acgacccg cctgctcgcc     900 ttgctgacca cgggcctgcc ggaccggagc atcgccaaac aactcggcat gagctaccgg     960
accttccagc gacggctccg cgacctcatg accgcgctcg gcgcgaccac ccggttccag    1020
gccgggcttc aggtcgccac gcggggttgg gtcaccttgc cgtcgaccca accccgatc    1080 gaggacgacg tcagcgagcg cgcggggttcg ccttcgccac gtccgtga                1128
```

<210> SEQ ID NO 29
<211> LENGTH: 1347
<212> TYPE: PRT
<213> ORGANISM: Amycolatopsis japonicum
<220> FEATURE:
<223> OTHER INFORMATION: ORF 1653

<400> SEQUENCE: 29

```
Met Phe Pro Arg Ser Pro His Leu Thr Arg His Pro Trp His Pro Val
 1               5                  10                  15

Ala Ile Leu Ala Ala Ser Ala Leu Val Ala Leu Thr Pro Leu Pro Val
            20                  25                  30

Ile Ala Thr Ala Ala Thr Ala Ala Val Ser Gly Pro Ala Pro Val Thr
        35                  40                  45

Gly Arg Pro Asp Val His Arg Val Thr Leu Leu Thr Gly Asp Val Val
    50                  55                  60

Thr Tyr Glu Arg Asp Gly Ala His Gly Thr Ala Gln Val Glu Pro
65                  70                  75                  80

Ala Val Arg Pro Asp Arg Pro Ser Pro Ala Phe Gln Ile Thr Thr Thr
                85                  90                  95

Ala Glu Gly Leu Met Val Tyr Pro Ser Asp Ala Leu Pro Phe Val Gly
            100                 105                 110

Lys Gly Leu Leu Ser Pro Asp Leu Phe Asn Val Thr Thr Leu Val Gly
        115                 120                 125

Asp Arg Arg Asp Ala Ala Ser Thr Thr Ile Pro Val Ile Val Arg
    130                 135                 140

Tyr Gly Asp Arg Ser Gly Leu Ser Ala Arg Thr Leu Asp Ala Lys Ala
145                 150                 155                 160

Lys Ala Leu Pro Gln Thr Gln Arg Leu Thr Pro Leu Val Thr Ala Asn
                165                 170                 175

Gly Val Gly Val Gln Val Lys Lys Ala Gly Thr Gly Glu Phe Trp Arg
            180                 185                 190

Ser Leu Val Ala Phe Asp Ala Ser Gly Lys Pro Val Leu Asn Gln Gly
        195                 200                 205

Ile Ser Gln Val Arg Leu Asp Arg Lys Val Arg Val Thr Leu Asp Lys
```

```
            210                 215                 220
Ser Thr Ala Arg Val Gly Ala Pro Ser Ala Trp Ser Gly Trp Thr
225                 230                 235                 240

Gly Lys Gly Thr Thr Val Ala Val Val Asp Thr Gly Ile Asp Glu Asn
                    245                 250                 255

His Pro Asp Leu Ala Gly Lys Thr Val Ala Ser Ala Asp Phe Ser Gly
                260                 265                 270

Glu Gly Asp Val Val Asp Arg His Gly His Gly Thr His Val Ala Ser
                275                 280                 285

Ile Val Ala Gly Thr Gly Ala Ala Ser Gly Gly Arg Tyr Lys Gly Val
            290                 295                 300

Ala Pro Asp Ala Asn Leu Val Val Ala Lys Val Phe Asp Ala Ser Gly
305                 310                 315                 320

Glu Gly Asp Thr Ala Gln Val Met Ala Gly Ile Asp Trp Ala Val Ala
                325                 330                 335

Gln Gly Ala Lys Ile Val Asn Leu Ser Leu Gly Ala Gly Val Ser Asp
                340                 345                 350

Gly Ala Asp Pro Met Ser Glu Gln Ile Asp Ser Leu Ser Ala Lys Ser
                355                 360                 365

Gly Thr Leu Phe Val Val Ala Ala Gly Asn Ser Gly Pro Gly Asp Arg
            370                 375                 380

Thr Val Thr Thr Pro Gly Ala Ala Thr Ser Ala Leu Thr Val Gly Ala
385                 390                 395                 400

Leu Asp Arg Glu Asp Lys Ile Ala Trp Phe Ser Ser Arg Gly Pro Arg
                405                 410                 415

Leu Arg Asp Ala Ser Val Lys Pro Glu Ile Thr Ala Pro Gly Val Gly
                420                 425                 430

Ile Val Ala Ala Arg Ala Ala Asp Thr Ala Leu Gly Glu Pro Val Asp
            435                 440                 445

Asp Ser Tyr Thr Ala Ala Ser Gly Thr Ser Met Ala Thr Pro His Val
450                 455                 460

Ala Gly Ala Ala Ala Ile Leu Leu Gln Gln Arg Pro Gly Leu Thr Gly
465                 470                 475                 480

Gln Ala Leu Lys Asn Thr Leu Val Thr Thr Ala Lys Asp Val Gly Leu
                485                 490                 495

His Trp Phe Glu Gln Gly Ala Gly Ile Leu Asp Val Arg Ala Val
                500                 505                 510

Ser Gln Lys Ala Thr Gly Thr Ala Val Ala Ser Phe Gly Arg Asn Glu
                515                 520                 525

Arg Thr Thr Asn Ala Ser Ala Gln Val Val Arg Gln Leu Ser Tyr Thr
                530                 535                 540

Asn Thr Gly Asp Gln Pro Leu Asn Leu Asn Leu Lys Leu Thr Val Arg
545                 550                 555                 560

Pro Trp Asp Gly Gly Ala Ala Pro Gly Thr Gly Met Arg Leu Ala Lys
                565                 570                 575

Thr Asp Leu Ser Ile Pro Pro Lys Ser Ser Thr Thr Val Asp Leu Ala
                580                 585                 590

Val Asn Pro Asn Glu Gly Thr Ala Gly Val Tyr Gly Gly Ala Val Val
                595                 600                 605

Ala Thr Thr Ala Asp Gly Thr Asn Ala Val Arg Thr Pro Val Ser Thr
            610                 615                 620

Tyr Asn Ala Ala Glu Leu Phe Pro Val Thr Ile Arg Val Arg Asp Ser
625                 630                 635                 640
```

```
Ala Gly Gly Pro Ala Gln Ser Ala Ser Ala Gln Leu Ile Asp Asp Ala
            645                 650                 655

Ala Gly Ala Gly Asn Arg Asn Asp Pro Phe Leu Asp Gln Val Ser Gln
            660                 665                 670

Gln Val Gly Leu Val Asp Gly Val Gly Arg Val Leu Val Pro Ala Gly
            675                 680                 685

Arg Tyr Ser Ala Leu Gly Trp Val Met Glu Arg Gly Leu Thr Val Arg
            690                 695                 700

Arg Trp Ser Ala Met Ser Ala Thr Gln Val Ala Val Ser Gly Pro Ala
705                 710                 715                 720

Glu Ile Ala Leu Asn Ala Ala Asn Ala Val Pro Ala Gly Leu Ile Thr
                725                 730                 735

Pro Thr Pro Thr Asp Leu Arg Asp Arg Thr Val Met Leu Arg Arg Val
            740                 745                 750

Ile Pro Gly Gly Ala Gly Val Asn Gly Tyr Val Gly Glu Ala Gly Leu
            755                 760                 765

Ala Ser Gly Ala Gly Trp Glu Val Arg Val Thr Pro Ala Ala Ala Thr
770                 775                 780

Ser Ala Gly Ala Ile Ser Leu Gln Asp Ser Ala Thr Leu Ser Gln Thr
785                 790                 795                 800

Ala Val Glu Met Arg Ile Val Gly Gly Pro Ala Val Leu Asn Pro
                805                 810                 815

Ala Tyr Asp Val Pro Thr Leu Thr Ala Lys Ser Pro Gly Glu Arg Thr
                820                 825                 830

Leu Pro Val Val Phe Gly Gly Ala Gly Asp Leu Thr Gly Leu Asp Val
            835                 840                 845

Arg Gly Lys Ala Val Leu Val Arg Ile Pro Val Pro Ala Gly Ala Pro
850                 855                 860

Asp Pro Val Ser Ala Val Ser Ala Gly Ile Ala Asn Ala Ser Arg Ala
865                 870                 875                 880

Val Ser Ala Ala Gly Gly Ala Ala Leu Ile Pro Tyr Ala Gly Ser Pro
                885                 890                 895

Gly Ser Leu Ser Val Pro Gly Leu Ser Ser Ala Val Val Pro Thr Leu
            900                 905                 910

Ser Leu Gly Trp Asp Glu Gly Glu Lys Leu Arg Thr Ala Gly Ala Val
            915                 920                 925

Ser Val Arg Leu Leu Val Arg Ser Ala Pro Ala Met Tyr Asn Leu
            930                 935                 940

Ser Tyr Leu Asp Ala Asn Gly Val Pro Lys Glu Leu Val Arg Arg Val
945                 950                 955                 960

Asp Gln Lys Thr Leu Val Ala Thr Lys Thr Gly Tyr Gln Ala Glu Lys
                965                 970                 975

Pro Gly Leu Thr Gly Gln Lys Asn Trp Tyr Ala Phe Pro Thr Gly Leu
            980                 985                 990

Trp Lys Thr Gln Ala Val Gln Gly Thr Lys Ile Pro Val Pro Gly Ser
            995                 1000                1005

Trp Thr Glu Tyr Thr Gly Pro Ala Asn Asp Arg Leu Val Trp Lys
            1010                1015                1020

Arg Val Val Thr Leu Ser Gly Asn Asp Thr Ala Gly Arg Arg Ala
            1025                1030                1035

Ala Leu Ser Met Asn Ala Gln Asn Val Tyr Arg Ala Gly Glu Arg
            1040                1045                1050
```

| | | | | | | | | | |
|---|---|---|---|---|---|---|---|---|---|
| Ser | Arg | Pro | Asp | Glu | Phe | Trp | Phe | Arg | Ala | Pro | Leu | His | Ser | Gly |
| | 1055 | | | | 1060 | | | | 1065 |

Ser Arg Pro Asp Glu Phe Trp Phe Arg Ala Pro Leu His Ser Gly
     1055                       1060               1065

Thr Val Glu Leu Pro Ala Asp His Pro Ala Arg Tyr Pro Ala Thr
     1070                       1075               1080

Ala Ser Gly Trp Ala Val Leu Cys Ser Met Cys Arg Gly Gly Thr
     1085                       1090               1095

Asp Pro Asp Leu Phe Leu Pro Gly Leu Gln Trp Met Asp Gly Thr
     1100                       1105               1110

Thr Gly Ala Gly Gly His Tyr Ala Asn Pro Tyr Glu Asn Ala Arg
     1115                       1120               1125

Tyr Phe Ala Ala Thr Thr Ala Arg Leu Tyr Arg Asp Gly Thr Glu
     1130                       1135               1140

Ile Pro Arg Ser Asn Ala Asp Asp Pro Leu Ala Leu Ile Pro Glu
     1145                       1150               1155

Phe Arg Leu Ala Pro Thr Pro Ala Thr Tyr Arg Leu Asp Val Thr
     1160                       1165               1170

Asp Val Leu Pro Gly Gln Ala Gln Val Gly Ile Pro Ser Gly Ala
     1175                       1180               1185

Leu Phe Gln His Ala Pro Arg Thr Asp Thr Ser Trp Thr Phe Ala
     1190                       1195               1200

Ser Ala Arg Ser Asp Ala Ala Ala Pro Leu Gly Phe Ser Cys His
     1205                       1210               1215

Asn Ala Gly Lys Ser Cys Ser Phe Gln Pro Leu Ile Gln Leu Asp
     1220                       1225               1230

His Arg Leu Pro Leu Asp Leu Gly Gly Arg Ala Pro Ala Gly Arg
     1235                       1240               1245

Pro Phe Thr Phe Asp Val Ser Ala Gly Ser His Ser Gly Ala Arg
     1250                       1255               1260

Gly Gly Gly Pro Val Thr Arg Leu Gln Val Ser Ala Ser Thr Asp
     1265                       1270               1275

Gly Gly Arg Thr Trp Thr Ala Ala Thr Val Arg Pro Gly Ala Asn
     1280                       1285               1290

Gly Leu Trp Ser Val Thr Val Ala His Pro Pro Leu Ala Ala Thr
     1295                       1300               1305

Asp Gly Phe Val Trp Leu Arg Ser Glu Ala Arg Asp Ser Ser Gly
     1310                       1315               1320

Asn Thr Val Thr Gln Thr Val Gln Arg Ala Tyr Ala Leu Thr Asp
     1325                       1330               1335

Val Ala Lys Ala Asn Pro Arg Ala Arg
     1340                       1345

<210> SEQ ID NO 30
<211> LENGTH: 4044
<212> TYPE: DNA
<213> ORGANISM: Amycolatopsis japonicum
<220> FEATURE:
<223> OTHER INFORMATION: orf 1653

<400> SEQUENCE: 30

| | | | | |
|---|---|---|---|---|
| atgttccccc | gttcccctca | cctgacgaga | caccctggc | accgggtggc gatcctggcg | 60 |
| gcctccgcac | tggtcgccct | cacccccttt | ccggtgatcg | cgaccgccgc gaccgccgcc | 120 |
| gtatccggcc | ccgctcccgt | caccgggcgg | ccggacgtcc | atcgcgtcac gttgctcacc | 180 |
| ggcgacgtgg | tgacctacga | acgagacggc | gccgggcacg | gcaccgcaca ggtcgaaccg | 240 |
| gcggtgcggc | cggaccggcc | gagcccggcg | ttccagatca | cgaccacggc cgaagggctg | 300 |

```
atggtgtatc cgtcggacgc gcttccgttc gtcggcaagg gactgctgag cccggacctg    360
ttcaacgtca ccacgctcgt cggagaccgg cgtgacgacg cggcgagcac cacgatcccc    420
gtcatcgtgc gttacggcga ccggtcgggg ctgtccgccc ggactctgga cgcgaaggcg    480
aaggcgctcc cgcagaccca gcggctcacc ccgctggtca cggccaacgg agtgggggtt    540
caggtcaaga aagcggggac gggcgaattc tggcgttccc tcgtcgcgtt cgatgcgagc    600
gggaaacccg ttttgaacca agggatttcg caagtccggc tggacaggaa ggtccgggtg    660
acgctggaca agagcaccgc gcgggtcggt gcgccgtcgg cgtggagcgg tgggtggacc    720
gggaagggga ccacggtcgc ggtggtggac accgggatcg acgagaacca tcccgacctg    780
gcgggcaaga cggtcgcctc cgcggacttc agcggcgagg gcgacgtcgt ggaccgccac    840
ggccacggca cgcacgtcgc gtcgatcgtc gccggtaccg gcgcggcatc gggcggccgg    900
tacaagggtg tggcaccgga cgcgaatctg gtggtggcca aggttttcga cgcgtccggc    960
gagggtgaca ccgcacaggt gatggccggg atcgactggg ccgtcgcgca gggcgcgaag   1020
atcgtgaacc tcagcctcgg cgccggcgtc agcgacgggg ccgacccgat gagcgagcag   1080
atcgactcgc tttcggcgaa gtccggcacg ctgttcgtgg tcgcggccgg gaactcgggg   1140
ccgggcgacc ggacagtcac gacaccgggg gcggcgacgt ccgcgctcac cgtcggagcg   1200
ctcgaccggg aggacaagat cgcgtggttc agcagccgcg gcccgcggtt gcgggacgcc   1260
tcggtcaaac cggagatcac cgcgcccggc gtcgggatcg tcgccgccag ggctgcggac   1320
acggcgctgg cgaaccggt ggacgactcc tacaccgccg cgtcgggcac ctcaatggcg   1380
acaccgcatg tcgcgggcgc cgcggcgatc ctgctgcagc agcgaccggg actgaccggg   1440
caggcactga agaacaccct cgtcaccacg gccaaggacg tcggtcttca ctggttcgag   1500
cagggcgccg gaatcctcga cgtcgcgcgg gccgtgtctc agaaggcgac cggcaccgcc   1560
gtcgcgagct tcggccgcaa cgaacggacg accaacgcct cggcacaggt cgtccggcag   1620
ctgtcctaca ccaacaccgg ggaccagccg ctgaacctca acctgaagct gaccgtgcga   1680
ccttgggacg gcggcgccgc gccgggtacc gggatgcgcc tggcgaagac ggatctgtcg   1740
atcccgccga agtcgagtac caccgtcgac ctcgccgtga cccgaacga aggaacggcg   1800 ggcgtctacg gcggcgccgt ggtggccacg accgcggacg ggaccaacgc ggtgcggact   1860
cccgtgagca cctacaacgc ggccgaactg ttccccggtga cgatccgggt ccgggactcg   1920
gcgggcgggc ccgctcagtc cgcgtcggcc cagctgatcg acgacgcggc cggtgcgggt   1980
aaccgcaacg acccgttcct cgaccaggtc agccagcagg tcggcctggt ggacggggtc   2040
ggccgggtgc tcgtgccagc cggacgctat tcggcgctcg gctgggtgat ggagcgcggg   2100
ctgacggtgc gccgctggtc ggcgatgagc gcgacgcagg tcgctgtcag cggcccggcg   2160
gagatcgcgc tgaacgcggc gaacgccgtc ccggcggggc tgatcacgcc cactcccacc   2220
gatctgcgga atcgcacggt gatgctgcgg cgcgtgatcc ccggcggagc cggtgtgaac   2280
ggttacgtcg gcgaagccgg gctggcttcg ggcgcgggct gggaggtgcg cgtgacccc   2340 gcggccgcca cctcggcggg cgcgattttcg ttgcaggaca gcgcgacact gtcccagacc   2400
gcggtcgaga tgcggatcgt cggtggcggt ccggccgtgc tgaacccggc gtacgacgtg   2460
ccgacgttga cggcgaagtc gcccggtgag cgaacgctgc cggtcgtgtt cggtggcgcg   2520
ggtgatctca ccggtctcga cgtccgcgga aaggccgtcc tggtaaggat tccggtcccg   2580
gccggggcac cggacccggt gagcgcggtc tccgcgggca tcgcgaacgc ttcacgcgcg   2640
```

```
gtgtccgccg cgggtggggc ggcgttgatc ccctacgccg ttctccggg ttcgctgagc   2700
gttccgggtc tcagcagcgc ggtggtgccg accttgtccc tcggctggga cgaaggcgaa   2760
aagttgcgga ccgccggtgc cgtttcggtg cgcttgctgg tgcgctcggc tccggacgcg   2820
atgtacaacc tcagctatct cgacgccaac ggcgtgccga aggagctcgt ccggcgggtc   2880
gaccagaaga ccttggtcgc cacgaaaacc ggctaccagg ccgaaaaacc gggactgacc   2940
ggacagaaga actggtacgc cttcccgacc ggcctgtgga agacacaggc ggtgcagggc   3000
acgaagatcc cggttccggg ctcctggacc gaatacaccg gcccggcgaa cgatcggctg   3060
gtctggaaac gggtcgtcac cctgtccggc aacgacaccg cggggcgccg cgccgcgctg   3120
agcatgaacg cgcagaacgt ctaccgcgcg ggcgagcggt cgagaccgga cgagttctgg   3180
ttccgcgcgc cactgcacag cggcacggtg gaactgcccg ccgatcatcc ggcccggtac   3240
ccggcgacgg cctccggctg gcggtgctg tgctcgatgt gccgtggtgg cacggatccc   3300
gacctgttcc tccccggcct gcagtggatg gacggcacga ccggggcggg cgggcattac   3360
gcgaatccct acgagaacgc gcggtacttc gcggcgacca cggcacggct gtaccgggac   3420
gggaccgaga tcccgcggtc caatgcggac gatccgctcg cgctcatccc ggagttccgg   3480
ctcgcgccga ccccgccac ctaccggctg acgtgaccg acgtgctgcc cggccaggcg   3540
caggtcggca tcccgagcgg ggcgctgttc cagcacgccc cgaggacgga cacgtcgtgg   3600
acgttcgcct cggcgcggtc agacgccgcg gcaccgctcg gcttctcctg ccacaacgcg   3660
ggcaagtcgt gttccttcca gccactcatc cagctggacc accggttgcc gctcgatctc   3720
ggcggccgcg ccccggccgg acgcccgttc accttcgacg tgtccgccgg ctcgcacagc   3780
ggcgcgcggg gcggcggacc ggtgacgcgg ctgcaggtgt cggcgtcgac ggacggcggg   3840
cgtacctgga cggcggcgac cgtccggccg ggcgcgaacg ggctgtggtc ggtgacggtg   3900
gcccacccgc cactcgcggc gacggacggg ttcgtctggc tgcgctcgga agcacgggac   3960
agctcgggca acaccgtgac gcagacggtc cagcgggcct acgcgctcac ggacgtggcg   4020
aaggcgaacc cgcgcgctcg ctga                                          4044
```

<210> SEQ ID NO 31
<211> LENGTH: 197
<212> TYPE: PRT
<213> ORGANISM: Amycolatopsis japonicum
<220> FEATURE:
<223> OTHER INFORMATION: ORF 1654

<400> SEQUENCE: 31

```
Met Leu Ala Met Gly Met Ala Gly Gly Val Ala Asn Ala Ala Gly Glu
1               5                   10                  15

Ser Glu Gly Thr Glu Ala Ala Pro Leu Val Ser Thr Val Val Ile
            20                  25                  30

Asn Glu Val Ser Thr Arg Gly Val Asn Gly Leu Leu Asp Glu Phe Ile
        35                  40                  45

Glu Leu Arg Asn Val Ser Asn Gln Pro Gln Asp Val Ser Gly Tyr Val
    50                  55                  60

Ile Arg Ile Tyr Ser Pro Ser Asn Val Val Thr Asp Thr Ile Val Leu
65                  70                  75                  80

Pro Ala Gly Thr Ile Leu Gln Pro Lys Gly Asn Ala Gly Gln Tyr Ala
                85                  90                  95

Val Leu Val Gly Gln Asn Phe Ser Gly Thr Val Val Asp Gln Thr Tyr
            100                 105                 110
```

Val Ile Pro Phe Thr Leu Thr Gly Ala Glu Gly Ile Pro Thr Ala Gly
            115                 120                 125

Gly Leu Ser Leu Gln Asn Met Ala Ala Lys Ile Asp Gly Val Ala
        130                 135                 140

Phe Ser Asn Ala Val Val Ala Pro Arg Glu Gly Gln Ala Ala Ile Pro
145                 150                 155                 160

Glu Asn Val Ile Thr Asp Gln Leu Asn Ala Ala Asn Thr Arg Asn Ile
                165                 170                 175

Leu Ser Thr Asp Thr Asp Asn Asn Arg Gln Asp Phe Ser Leu Gln Leu
            180                 185                 190

Arg Thr Pro Gly Leu
        195

<210> SEQ ID NO 32
<211> LENGTH: 594
<212> TYPE: DNA
<213> ORGANISM: Amycolatopsis japonicum
<220> FEATURE:
<223> OTHER INFORMATION: orf 1654

<400> SEQUENCE: 32
atgctggcga tgggtatggc cggtggtgtc gcgaacgcgg caggcgagag cgagggcacc      60
gaggccgccc cgctcgtgtc gtccaccgtg gtcatcaacg aggtttcgac ccgcggcgtg     120
aacggtctgc tcgacgagtt catcgagctg cgcaacgttt cgaaccagcc gcaggacgtg     180
agcggctacg tgatccggat ctactcgccg tcgaacgtcg tgaccgacac gatcgtcctg     240
ccggcgggca cgatcctgca gccgaagggc aacgcgggcc agtacgcggt gctcgtcggg     300
cagaacttct ccggcaccgt cgtcgaccag acctacgtca tccccttcac cctgaccggc     360
gccgagggca tcccgacggc cggtggcctt tcgctgcaga catggcggc cgcgaagatc     420 gacggtgtgg ccttcagcaa cgccgtcgtg gccccgcgtg aaggccaggc cgcgatcccg     480
gagaacgtca tcaccgatca gctcaacgcg gcgaacaccc gcaacatcct gagcaccgac     540
accgacaaca accggcagga cttctcgctg cagctgcgca ccccgggtct gtaa           594

<210> SEQ ID NO 33
<211> LENGTH: 94
<212> TYPE: PRT
<213> ORGANISM: Amycolatopsis japonicum
<220> FEATURE:
<223> OTHER INFORMATION: ORF 1655

<400> SEQUENCE: 33

Met Thr Ala Asn Ser Glu Arg Gly Ala Ala Ala Pro Leu Cys Glu Leu
1               5                   10                  15

Leu Ala Glu Gln Arg Ile Ala Lys Gly Trp Ser Gln Gly Asp Leu Val
            20                  25                  30

Val Lys Leu His Thr Arg Ser Gly Asn Asp Ser Val Thr Arg Glu Glu
        35                  40                  45

Ile Ser Arg Trp Glu Arg Gly Lys Arg Ile Pro Gly Pro Tyr Trp Arg
    50                  55                  60

Gln Trp Leu Ser Asp Val Leu Asp Thr Ser Ser Arg Glu Leu Glu Leu
65                  70                  75                  80

Ala Ala Ala Val Ala Arg Arg Arg Arg Asn Ile Ile Ala
            85                  90

<210> SEQ ID NO 34
<211> LENGTH: 285

```
<212> TYPE: DNA
<213> ORGANISM: Amycolatopsis japonicum
<220> FEATURE:
<223> OTHER INFORMATION: orf 1655

<400> SEQUENCE: 34
gtgaccgcga acagcgaacg cggggccgcg gccccgcttt gcgaactgct cgccgaacaa      60
cgaatcgcga aaggatggtc acaaggcgat ctggtcgtga agttgcacac ccgctccggc     120
aacgacagtg tcaccaggga agagatttcc cgctgggagc ggggaaaacg cattcccggt     180
ccctattggc ggcagtggct cagcgatgtg ctggacacct ccagccgcga gctcgaactc     240
gccgccgcgg tcgcgagaag gcggcgccgg aacattatcg cgtga                    285

<210> SEQ ID NO 35
<211> LENGTH: 166
<212> TYPE: PRT
<213> ORGANISM: Amycolatopsis japonicum
<220> FEATURE:
<223> OTHER INFORMATION: ORF 1656

<400> SEQUENCE: 35
```

Met Thr Lys Pro Gly Ser Leu Phe Leu Leu Ala Leu Ala Gly Thr
1               5                   10                  15

Pro Ala Pro Asp Thr Val Arg Ala Ser Ser Ala Lys Ile His Glu Val
            20                  25                  30

Leu Gly Gly Pro Ala Gly Tyr Ile Asp Leu His Asn Thr Gly Ala Thr
        35                  40                  45

Thr Leu Asp Ile Gly Gly Trp Ser Val Gln Ala Cys Thr Gly Ala
50                  55                  60

Thr Pro Val Glu Leu Ala Ala Met Pro Ala Gly Ser Glu Ile Pro Ala
65                  70                  75                  80

Gly Asp His Phe Leu Ile Thr Ala Gln Gly Phe Gly Gly Thr Met Gln
                85                  90                  95

Gln Val Val Val Glu Ala Ile Val Gly Asp Gly Glu Ile Leu Leu Asp
            100                 105                 110

Arg Arg Gly Ala Arg Val Asp Ser Val Gly Trp Ala Pro Ser Ser Pro
        115                 120                 125

Cys Arg Glu Asn Gln Ala Ala Val Ser Cys Pro Gly Leu Ala Gln Ser
    130                 135                 140

Arg Asp Ala Val Ser Arg Asp Thr Asp Asn Asn Lys Ala Asp Phe Gly
145                 150                 155                 160

Cys Val Arg Pro Ala Gly
                165

```
<210> SEQ ID NO 36
<211> LENGTH: 501
<212> TYPE: DNA
<213> ORGANISM: Amycolatopsis japonicum
<220> FEATURE:
<223> OTHER INFORMATION: orf 1656

<400> SEQUENCE: 36
atgacgaagc caggttccct gttcctgctc ctcgcactcg ccggaacccc ggccccggac      60
accgtccggg cttcgtcggc caagatccac gaggtgctcg gcggcccggc aggctacatc     120
gacctgcaca acaccggcgc caccacccct gacatcggcg gctggtccgt tcaggcgtgc     180
acgggcgggg cgacacccgt cgaactggcc gccatgcccg ccgggagcga gatccccgcc     240
ggtgaccatt tcctcatcac cgcacagggt ttcggcggga cgatgcagca ggtggtcgtc     300
```

```
gaggctatcg tcggggacgg cgagatactg ctggaccggc gcgggcgag ggtcgacagc        360 gtcggatggg cgccgtcgtc gccctgccgc gagaaccagg ccgccgtctc ctgccccggg        420
ctcgcccagt cgagggacgc cgtcagccgc gacaccgaca acaacaaggc cgacttcggc        480
tgtgtacggc cggccggctg a                                                  501
```

<210> SEQ ID NO 37
<211> LENGTH: 231
<212> TYPE: PRT
<213> ORGANISM: Amycolatopsis japonicum
<220> FEATURE:
<223> OTHER INFORMATION: ORF 1657

<400> SEQUENCE: 37

```
Met Asn Arg Val Thr Thr Leu Val Val Asp Asp Gln Pro Leu Ile Arg
 1               5                  10                  15

Tyr Ala Leu Ser Arg Leu Leu Arg Asp Ser Ala Gly Val Gly Ala Val
            20                  25                  30

Ala Glu Ala Ala Ser Glu Pro Glu Ala Leu Trp Gln Cys Glu Lys Ser
        35                  40                  45

His Pro Asp Met Val Ile Thr Glu Leu Ser Ile Trp Gly Glu Pro Ala
    50                  55                  60

Gly Thr Ala Ile Cys Arg Phe Val Lys Glu Gln Phe Glu Arg Ala Ala
65                  70                  75                  80

Val Leu Val Phe Ala Gly Asp Ser Ser Pro Ser Ala Ile Ala Met Ala
                85                  90                  95

Leu Asn Ala Gly Ala Asp Ser Phe Val His Lys Ser Ala Ser Gly Gly
            100                 105                 110

Gln Val Met Ser Ala Val Arg Ser Thr Leu Ala Gly Gln Arg Val Cys
        115                 120                 125

Leu Gln Ala Gly Gly Thr Pro Pro Ala Val Thr Glu Ala Val Arg Tyr
    130                 135                 140

Ala Ser Ala Met Thr Arg Arg Glu Glu Ile Leu Ala Leu Ile Leu
145                 150                 155                 160

Tyr Arg Trp Ser Asn Asp Glu Ile Ala Glu Glu Leu His Leu Ala Thr
                165                 170                 175

Gln Thr Val Lys Asn Tyr Val Ser Arg Ile Leu Gln Lys Leu Gly Phe
            180                 185                 190

Gly Ser Arg Arg Asp Leu Phe Arg Ala Leu Arg Phe Arg Pro Gly Gly
        195                 200                 205

Asn Leu Leu Pro Arg Leu Glu Thr Thr Glu Arg Glu Gly Glu Leu His
    210                 215                 220

Thr Ala Asp Gly Tyr Arg Gly
225                 230
```

<210> SEQ ID NO 38
<211> LENGTH: 696
<212> TYPE: DNA
<213> ORGANISM: Amycolatopsis japonicum
<220> FEATURE:
<223> OTHER INFORMATION: orf 1657

<400> SEQUENCE: 38

```
atgaaccgcg tcaccacgct cgtagtagac gatcaacccc tcatcagata cgcgctcagc         60
aggctgttgc gggattcggc gggggtgggg cggtggccg aagccgcgag tgagcctgaa        120
gcgttgtggc agtgcgaaaa gagccatccc gacatggtca tcaccgagct gtcgatctgg       180
```

```
ggtgagcctg ccgggaccgc gatctgccgg ttcgtgaagg aacagttcga acgcgctgcc        240
gtcctggtct cgccggtga ttcgtcgcca tcggccatcg cgatggcgct gaacgcgggt        300
gcggacagct tcgtgcacaa gtcggccagc ggcggccagg tgatgtcggc ggtgcgctcg        360 acgtcgccg gcagcgggt gtgcctgcag gcgggcggaa ccccgccggc ggtcaccgag          420
gccgtgcgct acgcgagcgc gatgaccaga cgggaggagg agatcctcgc gctgatcctc        480
taccggtggt cgaacgacga gatcgccgag gaactgcatc tcgccacgca gaccgtgaag        540
aactacgtca gccggatcct gcagaagctg ggcttcggca gcagacgcga cctcttccgg        600
gcgctgcgtt tccggccggg cggaaacctg ttgccgcgcc tggagacgac cgagcgcgaa        660
ggcgagttgc acacggcgga cgggtaccgg ggctag                                  696

<210> SEQ ID NO 39
<211> LENGTH: 139
<212> TYPE: PRT
<213> ORGANISM: Amycolatopsis japonicum
<220> FEATURE:
<223> OTHER INFORMATION: ORF 1658

<400> SEQUENCE: 39

Met Asp Asp Ser Tyr Arg Leu Glu Ala Gly Ser Pro Ser Val Asp
1               5                   10                  15

Tyr Leu Arg Leu Arg Arg Glu Ala Gly Leu Ser Glu Pro Pro Arg Glu
                20                  25                  30

Gln Ala Glu Arg Gly Val Arg Gly Ala Trp Thr Ser Val Arg Val Val
            35                  40                  45

His Arg Pro Thr Gly Glu Thr Val Gly Met Gly Arg Val Ile Ser Asp
        50                  55                  60

Gly Gly Trp Tyr Phe His Ile Val Asp Met Ala Val Leu Pro Ala His
65                  70                  75                  80

Gln Arg Arg Gly Ile Gly Asp Ala Val Leu Glu Ala Leu Leu Ala Ala
                85                  90                  95

Ile Asp Thr Ala Ala Pro Gly Ala Tyr Val Asn Leu Leu Gly Asp Pro
            100                 105                 110

Pro Gly Trp Arg Leu Tyr Lys Arg His Gly Phe Val Glu Thr Ala Pro
        115                 120                 125

Gly Thr Ile Gly Met Arg Arg Gln Asn Ala Gly
    130                 135

<210> SEQ ID NO 40
<211> LENGTH: 420
<212> TYPE: DNA
<213> ORGANISM: Amycolatopsis japonicum
<220> FEATURE:
<223> OTHER INFORMATION: orf 1658

<400> SEQUENCE: 40
atggacgact cttaccgcct ggaagcaggc tccccgtcgg tcgacgacta cctgcggctg        60
cgccgcgagg ccggtctcag cgaaccgccg agggaacagg cggagcgcgg ggttcgcggc       120
gcctggacgt cggtccgggt ggtccaccgg cccaccggcg agaccgtcgg gatgggccgg       180
gtgatcagcg acggtgggtg gtacttccac atcgtcgaca tggccgttct gcccgcccat       240
cagcgccgcg gcatcgggga cgccgtcctc gaggcccttc tcgcggcgat cgacaccgcg       300 gcgccggggtg cgtacgtcaa tctgctcggc gatccaccg gatggcggct ctacaaacgc       360
cacggtttcg tggagaccgc tcccgggacc atcggcatgc ggcgccaaaa cgccggataa       420
```

<210> SEQ ID NO 41
<211> LENGTH: 174
<212> TYPE: PRT
<213> ORGANISM: Amycolatopsis japonicum
<220> FEATURE:
<223> OTHER INFORMATION: ORF 1659

<400> SEQUENCE: 41

```
Met Thr Val Thr Thr Leu Arg Pro Gly Leu Pro Glu Leu Ile Lys Arg
 1               5                  10                  15

Leu Arg Gln Cys Thr Gly Arg Pro Ser Glu Pro Leu Val Thr Ala Gln
            20                  25                  30

Ala Val Ala Asn Val Leu Thr Glu Leu Arg Pro Thr Pro Gln Leu Leu
        35                  40                  45

Thr Ala Thr Glu Arg Ala Gly Ser Pro Asp Gly Tyr Thr Arg Thr Thr
    50                  55                  60

Leu His Ala Glu Ser Ala Phe Ser Ile Val Gly Leu Val Trp Arg Pro
65                  70                  75                  80

Gly Gln Leu Thr Glu Ile His Asp His Leu Val Trp Cys Thr Phe Leu
                85                  90                  95

Val Leu Gln Gly Thr Glu Thr Glu Thr Ile Phe Asp Ile Asp Asp Asp
           100                 105                 110

Arg Leu Val Arg Lys Ala Gln Arg Gln Arg Pro Ala Gly Ser Val Ser
       115                 120                 125

Gly Val Ala Pro Pro Asp Asp Ile His Gln Val His Asn Ala Gly Asp
   130                 135                 140

Thr Val Ala Ile Thr Leu His Val Tyr Gly Ala Asp Leu Ser Lys Gly
145                 150                 155                 160

Thr Ser Val Arg Arg Asn Tyr Arg Met Arg Ala Thr Ser Arg
                165                 170
```

<210> SEQ ID NO 42
<211> LENGTH: 525
<212> TYPE: DNA
<213> ORGANISM: Amycolatopsis japonicum
<220> FEATURE:
<223> OTHER INFORMATION: orf 1659

<400> SEQUENCE: 42

```
atgaccgtca cgaccctcag accaggcctt ccggagctga tcaaacgtct gcgccaatgc      60
accggaagac catccgaacc ccttgtcacc gcacaagccg tggcgaacgt tctcaccgaa     120
ctccgcccga ctccgcaact gctcaccgcg acggaacgcg ccggctcccc cgacggctac     180
acccgcacca ccctgcacgc cgagtccgcc ttttcgatcg tcggactggt ctggcggccc     240
ggtcagctca ccgagatcca cgatcacctg gtgtggtgta cattccttgt cctgcaagga     300
accgagaccg agaccatctt cgacatcgac gacgatcggc tggtccggaa ggcccagcgg     360
caacgcccgg cggggtcggt gagcggcgtc gcgccgcccg acgacatcca ccaggtgcac     420
aacgcgggcg acaccgtcgc catcaccttg cacgtgtacg gcgccgacct gagcaaggga     480
accagcgtgc gccgcaatta ccggatgcgc gccacttcgc ggtga                      525
```

<210> SEQ ID NO 43
<211> LENGTH: 288
<212> TYPE: PRT
<213> ORGANISM: Amycolatopsis japonicum
<220> FEATURE:
<223> OTHER INFORMATION: ORF 1660

<400> SEQUENCE: 43

Met Leu Asn Leu Val Gln Leu Thr Val Leu Ala Ala Val Ala Arg His
1               5                   10                  15

Gly Ser Met Thr Ala Ala Ala Lys Glu Leu His Tyr Thr Gln Pro Ala
            20                  25                  30

Val Ser His His Leu Ala Arg Leu Glu Ala Thr Gly Ala Lys Leu
        35                  40                  45

Val Gln Arg Ile Gly Arg Gly Ile Arg Leu Thr Pro Glu Gly Glu Leu
    50                  55                  60

Leu Ala Ala Arg Ala Ala Glu Ile Val Gly Arg Val Glu Gly Ala Glu
65                  70                  75                  80

Ala Glu Leu Ala Ala Gln Val Gly Leu Arg Ala Gly Arg Val Arg Met
                85                  90                  95

Ala Gly Phe Gln Ser Ile Leu Ser Thr Ile Val Pro Asp Ala Ala Ala
            100                 105                 110

Thr Leu Ala Arg Ala His Pro Gly Leu Glu Leu Gly Leu Val Asp Glu
        115                 120                 125

His Pro Gly Glu Ala Leu Arg Met Leu Arg Glu Gly Arg Ile Asp Val
130                 135                 140

Ala Leu Ile Phe Arg Tyr Ala Asp Thr Pro Arg Glu Glu Gln Gly Leu
145                 150                 155                 160

Arg Leu Val His Leu Leu Glu Asp Pro Ile Tyr Leu Leu Thr Ser Glu
                165                 170                 175

Pro Gly Gln Thr Ile Ala Asp His Arg Asp Ser Thr Trp Ile Gly Gly
            180                 185                 190

Cys Ala Arg Cys Gln Asp Glu Leu Val Thr Ile Cys Gly Arg Ala Gly
        195                 200                 205

Phe Ala Pro Arg Ile Ser Met Val Ser Asp Ile Val Val Met Gln
210                 215                 220

Ala Leu Val Ala Ala Arg Met Gly Val Thr Thr Leu Pro Arg Leu Ala
225                 230                 235                 240

Leu Arg Ala His Arg Met Pro Gly Val His Ala Thr Glu Leu Ala Glu
                245                 250                 255

Asp Pro Arg Gln Ile Tyr Ala Val Thr Tyr Gly Asp Pro Pro Asp Pro
            260                 265                 270

Pro Ala Ala Ala Leu Ile Asp Ala Leu Gln Thr Ser Ile Arg Ala
        275                 280                 285

<210> SEQ ID NO 44
<211> LENGTH: 867
<212> TYPE: DNA
<213> ORGANISM: Amycolatopsis japonicum
<220> FEATURE:
<223> OTHER INFORMATION: orf 1660

<400> SEQUENCE: 44
atgctgaatc tggtgcagct cacggtgctg gcggcggtcg cgcggcacgg ttcgatgacc      60
gcggcggcga aggaactgca ctacacgcag cccgcggtga gccaccatct cgcgaggttg     120
gaggcggcga cgggcgcgaa gctggtccag cggatcggcc gcggcatccg gctcacaccg     180 gaagggaac tgctcgccgc ccgcgcggcc gagatcgtcg gcgggtcga aggcgccgaa       240 gccgagttgg ccgcgcaggt gggcttgcgc gccgggcggg tcggatggc ggggttccag      300 tcgatcctga gcacgatcgt ccccgacgcg gccgcgacgc tggcccgtgc gcatcccgga     360

-continued

```
ctcgaactcg ggctggtgga cgaacatccg ggcgaggcgc tgcgcatgct gcgggagggg       420
cggatcgacg tcgccctgat cttccggtac gcggacacgc cccgcgagga cagggggctc       480
cggctcgtgc acctgctgga ggacccgatc tacctgctca ccagcgaacc ggggcagacc       540
atcgccgatc atcgtgactc gacctggatc ggcggctgcg cccgatgcca ggacgaactc       600
gtcacgatct gcgggcgggc cgggttcgcc ccgcgtattt cgatggtcag cgacgacatc       660
gtggtcatgc aggcgctggt cgcggcccgg atgggcgtca ccacgctgcc ccggctggcg       720
ctgcgtgcgc atcggatgcc cggtgtgcac gccacggagc tggccgaaga cccgcgtcag       780
atctatgccg tcacctatgg cgacccgccc gatcctccgg ccgcagcggc gttgatcgac       840
gcgcttcaga cgagcatccg ggcttag                                            867
```

<210> SEQ ID NO 45
<211> LENGTH: 411
<212> TYPE: PRT
<213> ORGANISM: Amycolatopsis japonicum
<220> FEATURE:
<223> OTHER INFORMATION: ORF 1661

<400> SEQUENCE: 45

```
Met Arg His Leu Asn Ala Ile Gly His Leu Ala Pro His Asp His Ala
1               5                   10                  15

Ala Ala Pro Ala Gly Pro Leu Ser Gly Ile Pro Leu Val Val Lys Asp
            20                  25                  30

Asn Ile His Val Ala Gly Met Pro Asn Thr Ala Gly Thr Pro Ala Leu
        35                  40                  45

Ala Gly His Val Pro Arg Glu His Ala Thr Val Val Arg Arg Leu Thr
    50                  55                  60

Asp Ala Gly Ala Val Val Val Gly Lys Ala Thr Met His Glu Leu Ala
65                  70                  75                  80

Leu Gly Ile Thr Cys Asp Thr Thr Pro Leu Gly Pro Val Arg Asn Ala
                85                  90                  95

Cys Asp Pro Ser Arg Phe Ala Gly Gly Ser Ser Gly Gly Thr Ala Val
            100                 105                 110

Ala Val Ala Ala Gly Ile Val Pro Ala Gly Leu Gly Thr Asp Thr Gly
        115                 120                 125

Gly Ser Ala Arg Val Pro Ala Ala Leu Asn Gly Val Cys Gly Phe Arg
130                 135                 140

Pro Thr Thr Gly Arg Tyr Pro Ser Asp Gly Met Thr Pro Leu Ser Ser
145                 150                 155                 160

Thr Arg Asp Thr Ala Gly Pro Ile Ala Arg Thr Val Ala Asp Leu Ala
                165                 170                 175

Leu Leu Asp Ala Val Leu Ala Glu Glu Pro Thr Pro Leu Ile Glu
            180                 185                 190

Ser Thr Ser Val Arg Leu Gly Val Pro His Gly Phe Leu Thr Gly Asp
        195                 200                 205

Leu Ser Glu Asp Val Glu Glu Leu Trp Glu Ala Ala Leu Ala Arg Leu
    210                 215                 220

Gly Ala Ala Gly Val Thr Leu Val Pro Leu Asp Asp Thr Pro Leu Ala
225                 230                 235                 240

Glu Leu Val Val Asp Gln Gly Met Pro Leu Val Ile His Glu Ala Gly
                245                 250                 255

Val Gly Leu Arg Ser Tyr Leu Ala Glu His Val Pro Glu Val Ser Phe
            260                 265                 270
```

```
Glu Arg Leu Val Arg Glu Ile Ala Ala Pro Asp Val Arg Ala Ile Phe
            275                 280                 285

Ala Glu Ala Val Val Pro Gly Val Glu Pro Ala Val Tyr Glu Ala Ala
        290                 295                 300

Ile Thr Thr Arg Ser Ala Leu Arg Arg Ala Tyr Ala Lys Ile Phe Asp
305                 310                 315                 320

Glu Ser Gly Ile Asp Ala Leu Ala Phe Pro Thr Thr Pro Ala Thr Ala
                325                 330                 335

Arg Asp Phe Ser Ala Val Gly Ser Phe Val His Arg Gly Arg Glu Val
            340                 345                 350

Pro Thr Phe Pro Thr Phe Ile Arg Asn Cys Gln Pro Gly Ser Ile Ala
        355                 360                 365

Gly Phe Pro Gly Leu Thr Val Pro Met Gly Arg Ala Arg Asp Gly Leu
    370                 375                 380

Pro Ala Gly Leu Ala Leu Asp Gly Leu Val Gly Asp Asp Arg Lys Leu
385                 390                 395                 400

Leu Gly Val Gly Ala Phe Val Glu Arg Val Leu
                405                 410

<210> SEQ ID NO 46
<211> LENGTH: 1236
<212> TYPE: DNA
<213> ORGANISM: Amycolatopsis japonicum
<220> FEATURE:
<223> OTHER INFORMATION: orf 1661

<400> SEQUENCE: 46
gtgcggcatc tcaacgcgat cggccacctg gcgccgcacg atcacgcggc cgcgccggcc       60
ggcccgctca gcgggatccc gttggtggtc aaggacaaca tccacgtcgc cgggatgccg      120
aacaccgcgg gtaccccggc gctggcgggc acgttccgc gcgagcacgc gaccgtggtc       180
cgacggctga ccgacgcggg cgccgtcgtc gtcggcaagg cgaccatgca cgaactcgcc      240
ctcggcatca cctgcgacac gaccccgctc ggcccggtgc gcaacgcgtg cgacccgtcc      300
cggttcgccg gggcagcag cggcgggacc gcgtcgccg tcgcggcggg catcgtgccc        360
gcgggtctgg gcaccgacac cggcggttcg gcccgtgttc ccgccgcgct caacggggtt      420
tgcggcttcc ggccgaccac gggccgctac ccgtccgacg gcatgacgcc gctgagcagc      480
acgcgggaca cggccgggcc gatcgcccgc acggtcgccg atctcgcgct cctcgacgcg      540
gtcctcgcgg cggaagagcc gacacccctg atcgagagca cgtcggtcag gctgggtgtg      600
ccgcacggtt tcctgaccgg cgacctgtcc gaggacgtcg aagaactctg gaagccgcg       660 cttgcccgct tgggcgcggc aggcgtcacc ctggtgccgc tcgacgacac gccgctcgcc      720
gaactcgtcg tcgatcaggg aatgccgctg gtgatccacg aagcaggcgt cgggctccgc      780
tcctacctcg ccgagcacgt acccgaggtt tcgttcgagc ggctcgttcg cgagatcgcc      840
gcgcccgacg tccgggcgat cttcgccgaa gcgtcgtgc cgggcgtcga accgccgtc        900 tacgaagcgg ccatcaccac ccgctccgcc ttgcgtcgcg cctacgcgaa gatcttcgac      960
gagagcggca tcgacgcgct ggccttcccc accacaccgg cgacggcccg ggacttctcg     1020
gccgtcggga gcttcgtgca ccgagggcgc gaggtcccga ccttccccac cttcatccgc     1080
aactgccagc ccggcagtat cgcgggattc cccggcctga ccgtcccgat ggggcgcgca     1140
cgcgacggcc tgcccgccgg gctggcgctc gacggcctgg tcggggacga ccggaagttg     1200
ctgggcgtgg gggctttcgt cgaacgggtt ctgtag                               1236
```

<210> SEQ ID NO 47
<211> LENGTH: 327
<212> TYPE: PRT
<213> ORGANISM: Amycolatopsis japonicum
<220> FEATURE:
<223> OTHER INFORMATION: ORF 1662

<400> SEQUENCE: 47

Met Ser Ser Gly Pro Ser Leu His Val Leu Thr Arg Ser Asp Leu His
1               5                   10                  15

Ser Leu Glu Leu Thr Pro Gly Glu Ala Ile Thr Met Val Glu Asp Gly
            20                  25                  30

Tyr Leu Ala Tyr Ala Ala Gly Ala Ser Arg Asn Pro Ala Lys Leu Met
        35                  40                  45

Val Pro Ile Pro Asp Pro Ala Arg Asp Ala Val Ala Tyr Ser Met Leu
    50                  55                  60

Gly Tyr Asp Gly Ser Leu Glu Gln Ala Ala Phe Lys Thr Ser Tyr Arg
65                  70                  75                  80

Gln Gly Ser Thr Ser Ala Glu Lys Tyr Tyr Thr Thr Ile Thr Leu Tyr
                85                  90                  95

Asp Asp Thr Thr Gly Leu Pro Phe Ala Leu Met Asp Cys His Arg Val
            100                 105                 110

Gly Ala Thr Arg Thr Pro Ala Ser Thr Ala Leu Ile Ala Arg Ser Cys
        115                 120                 125

Ala Arg Pro Gly Ala Arg Ser Ala Leu Met Val Gly Thr Gly Ala Gln
    130                 135                 140

Gly Ile Arg Thr Leu Pro Tyr Leu Leu Thr Ala Leu Pro Glu Leu Glu
145                 150                 155                 160

Arg Leu Arg Leu Phe Gly Thr His Pro Asp Gly Leu Arg Asp Ser Val
                165                 170                 175

Ala Ala Leu Lys Glu Arg Phe Pro Asp Arg Glu Val Glu Leu Val Asp
            180                 185                 190

Asp Val Glu Ala Ala Ala Arg Glu Ser Asp Ile Val Val Ala Ala Ser
        195                 200                 205

Gly Arg Ala Ala His Pro Lys Ile Arg Leu Gly Trp Leu Pro Pro Gly
    210                 215                 220

Gly Leu Leu Ile Ser Val Ala Ser Lys Gly Val Gln Glu Gly Thr Leu
225                 230                 235                 240

Ala Glu Ala Asp Tyr Thr Val Ala Thr Ser Gly Ala Gln Val Glu Val
                245                 250                 255

Thr Gly Gln Arg Met Ala Gly Pro Asp Gly Val Phe Arg Ile Asp Ala
            260                 265                 270

Glu Leu Pro Glu Ile Leu Ala Gly Lys Ala Pro Gly Arg Arg Gly Asp
        275                 280                 285

Glu Asp Arg Val Phe Ala Phe Ser Ser Gly Met Ile Ile Thr Asp Ile
    290                 295                 300

Pro Val Ala His Ala Leu Ala Ala Arg Ala Ile Ala Ala Gly Arg Gly
305                 310                 315                 320

Arg Glu Val Ala Leu Trp Thr
                325

<210> SEQ ID NO 48
<211> LENGTH: 984
<212> TYPE: DNA
<213> ORGANISM: Amycolatopsis japonicum
<220> FEATURE:

<223> OTHER INFORMATION: orf 1662

<400> SEQUENCE: 48

```
atgagctccg gtccctcgct gcacgtactc acgcgctcgg atctgcacag cctcgaactc      60
accctggcg aggcgatcac gatggtcgaa gacggctatc tggcctacgc ggccggggcc     120
tcgcggaacc cggcgaagct gatggtgccg atcccggatc ccgcgcggga cgccgtcgcg     180
tactcgatgc tcggctacga cggttccctc gaacaggccg cgttcaagac gagctaccgc     240
caaggcagca cgtcggccga aagtactac acgaccatca ccctgtacga cgacaccacg     300
ggcctgccgt tcgcgctcat ggactgccac cgcgtcggcg ccaccccgca gcccgcgagc     360
accgcgttga tcgcgcggtc ctgcgctcgg ccgggcgcgc gatccgcgct catggtcggc     420
accggcgcgc aggggatccg gacgctgccg tacctgctca ccgcgctgcc ggagctggaa     480
cggctgcggc tgttcggcac gcatcccgac ggtcttcgcg acagcgtcgc cgcgctgaag     540
gagcgcttcc cggaccgcga ggtcgaactc gtcgacgacg tggaggccgc ggcgcgcgag     600
tccgacatcg tggtcgccgc gtcgggccgg gcggcccacc cgaagatccg tctcggctgg     660
ctgccgccgg gcgggctgct gatctccgtc gccagcaagg gagtccagga aggcacgctc     720
gccgaggccg actacacggt ggccaccagc ggcgcgcagg tcgaggtgac cgggcagcgg     780
atggcgggtc cggacggcgt gttccggatc gacgccgaac tcccggagat cctcgcgggc     840
aaggcccccg ccgccgcgg cgacgaagac cgggtgttcg ccttcagcag cggcatgatc     900
atcaccgaca tcccggtggc gcacgcgctg gccgcccgcg ccatcgccgc cggccgcggc     960
cgcgaggtgg ccctgtggac ctga                                            984
```

<210> SEQ ID NO 49
<211> LENGTH: 448
<212> TYPE: PRT
<213> ORGANISM: Amycolatopsis japonicum
<220> FEATURE:
<223> OTHER INFORMATION: ORF 1663

<400> SEQUENCE: 49

```
Met Asp Leu Ile Asp Thr Leu Ser Pro Pro Leu Pro Ala Leu Glu Arg
1               5                   10                  15

Pro Trp Ala His Arg Leu Arg Ala Ser Glu Thr Leu Trp Glu Ile Ala
            20                  25                  30

Arg Gly Val Gly Gly Gly Pro Phe His Val Val His Pro Ala Thr Phe
        35                  40                  45

Ala Glu Asn Leu Gly Glu Met Val Asp Ala Leu Ala Ala Glu Arg Val
    50                  55                  60

Glu Gly Thr Val Tyr Tyr Gly Lys Lys Ala Asn Lys Ala Ala Ala Trp
65                  70                  75                  80

Leu Arg Glu Cys Thr Arg Pro Gly Thr Gly Val Asp Val Ala Ser Val
                85                  90                  95

Pro Glu Leu Val His Ala Leu Gly Asn Gly Leu Arg Gly Glu Ala Ile
            100                 105                 110

Gly Val Thr Gly Ala Ala Lys Pro Asp Gly Leu Leu Trp Leu Ala Leu
        115                 120                 125

Arg His Arg Cys Leu Ile Ala Val Asp Ala Ala Asp Glu Leu Glu Arg
    130                 135                 140

Val Ala Arg Leu Ala Thr Glu Leu Gly Glu Thr Ala Glu Val Leu Leu
145                 150                 155                 160

Arg Val Arg Pro Pro Ser Ala Pro Glu Ser Arg Phe Gly Phe Ala Pro
```

```
                    165                 170                 175
Asp Ala Val Lys Ala Ala Val Arg Gln Cys Gly Gly Pro Val Val Leu
                180                 185                 190

Arg Gly Phe Ser Phe His Leu Asp Gly Tyr Asp Pro Val Pro Arg Ala
            195                 200                 205

Glu Leu Ala Ala Tyr Leu Ile Asp Leu Cys His Asp Ala Arg Ala Leu
        210                 215                 220

Gly His Pro Ala Ser Lys Ile Ser Ala Gly Gly Ile Ala Val Ser
225                 230                 235                 240

Tyr Val Asp Ala Gly Asp Trp Ala Arg Phe Glu Ser Gly Arg His Asp
                245                 250                 255

Gly Trp Phe His Ala Gly Arg Asn Pro Ala Arg Thr Tyr Pro Tyr His
            260                 265                 270

Gln Ala Pro Thr Gly Ala Ala Met Val Thr Ala Ile Leu Arg His Glu
        275                 280                 285

Ile Ala Gly Lys Thr Leu Ala Glu Arg Leu Arg Ala Ala Gly Ile Glu
    290                 295                 300

Leu Leu Leu Glu Pro Gly Arg Ala Leu Val Asp Gly Ala Gly Phe Ser
305                 310                 315                 320

Val Phe Pro Val Leu Gly Cys Lys Pro Ala Glu Asp His Leu Ile Thr
                325                 330                 335

Thr Val Ala Gly Leu Ser Met Ser Leu Ser Gln Trp Lys Gly Ser
            340                 345                 350

Glu Phe Leu Pro Asp Pro Leu Leu Val Arg Arg Asp Gly Pro Gly Gly
        355                 360                 365

Thr Pro Val Arg Thr Ile Val Ala Gly Ser Ser Cys Met Glu Tyr Asp
    370                 375                 380

Val Leu Thr Trp Arg Ala Val Glu Leu Pro Ala Gln Pro Arg Thr Gly
385                 390                 395                 400

Asp Leu Leu Val Tyr Pro Asn Thr Ala Gly Tyr Gln Met Asp Lys Asn
                405                 410                 415

Glu Ser Gly Phe His Gln Leu Pro Leu Pro Pro Lys Val Val Val Asp
            420                 425                 430

Gly Asp Arg Trp His Leu Asp Thr Asp His Pro Ile Gln Glu Ile Arg
        435                 440                 445
```

<210> SEQ ID NO 50
<211> LENGTH: 1347
<212> TYPE: DNA
<213> ORGANISM: Amycolatopsis japonicum
<220> FEATURE:
<223> OTHER INFORMATION: orf 1663

<400> SEQUENCE: 50

```
gtggacctga tcgacaccct gtccccgccc ctgcccgcgc tcgaacgtcc ctgggcgcac     60
cggctgcgtg cttcggagac gctgtgggag atcgcccgcg ggtcggcgg cggcccgttc    120
cacgtggtcc atccggccac tttcgccgag aacctcgggg aaatggtcga cgcgctcgcc    180
gccgaacggg tcgaaggcac cgtctactac gggaagaagg cgaacaaggc ggcggcctgg    240
ctgcgggaat gcacgcgtcc cggcacgggg gtcgacgtcg cgagtgtgcc cgaactggtg    300
cacgccctcg gaaacgggct gcgcggcgaa gcgatcgggg tcaccggcgc cgccaaaccc    360
gacgcctcc tttggctcgc cctgcggcat cgctgtctca tcgcggtgga cgcggccgac    420
gagctggaac gcgtcgcccg gctggccacc gaactcgggg agaccgccga agtgctgctg    480
```

-continued

```
cgagtgcggc cgccgtccgc gccggagagc cggttcggtt tcgcgcccga cgcggtgaaa    540
gcggccgtgc gacagtgcgg cggcccggtc gtcctgcggg gtttctcgtt ccacctcgac    600
ggctacgacc ccgtgccgag ggcggaactc gccgcatacc tgatcgatct gtgtcacgac    660
gcccgcgcgc tcggacatcc cgcgtcgaag atcagtgcgg gcggcgggat cgctgtgtcc    720
tatgtggacg ccggtgactg ggcgcggttc gagtccggca ggcacgacgg ctggttccac    780
gccggccgta atccggccag gacctatcca taccaccagg cgccgaccgg ggcggcgatg    840
gtgaccgcga tcctccggca cgagatcgcc gggaagacac tggccgagcg cctgcgcgcg    900
gccgggatcg agctgctgct cgaacccggc cgagccctcg tcgacggcgc cgggttctcg    960
gtgttcccgg tgctgggctg caaaccggcc gaagaccacc tgatcaccac ggtcgcgggc   1020
ctgtccatga gcctgtccga acagtggaag ggcagcgagt tcctgcccga cccgctgctc   1080
gtgcgcaggg acggaccggg cggtacgcca gtgcggacca tcgtcgcggg gtcgagctgc   1140
atggagtacg acgtgctgac ctggcgcgcg gtggagctgc ccgcgcaacc gaggaccggc   1200
gacctgctcg tgtaccccaa cacggccggc taccagatgg acaagaacga gagcggtttc   1260
caccagcttc cgttgccgcc gaaagtggtg gtcgacggcg accgctggca cctcgacacc   1320
gaccacccga tccaggagat ccgatga                                        1347
```

<210> SEQ ID NO 51
<211> LENGTH: 352
<212> TYPE: PRT
<213> ORGANISM: Amycolatopsis japonicum
<220> FEATURE:
<223> OTHER INFORMATION: ORF 1664

<400> SEQUENCE: 51

```
Met Thr Ile Val Arg Arg Ala Ser Asp Leu Ile Gly Asn Thr Pro Leu
1               5                   10                  15

Leu Glu Leu Ala Arg Thr Gly Thr Gly Thr Arg Leu Leu Leu Lys Leu
            20                  25                  30

Asp His Leu Asn Pro Thr Gly Ser Cys Lys Val Arg Met Ala Arg Gln
        35                  40                  45

Met Ile Asp Glu Ala Glu Leu Asp Gly Arg Leu Arg Pro Gly Gly His
    50                  55                  60

Ile Val Glu Pro Thr Ser Gly Asn Thr Gly Asn Gly Leu Ala Leu Val
65                  70                  75                  80

Ala Leu Glu Arg Gly Tyr Arg Phe Thr Ala Val Val Asp His His Ala
                85                  90                  95

Ala Arg Glu Lys Leu Gly Met Leu Arg Ala Leu Gly Ala Glu Leu Val
            100                 105                 110

Phe Val Glu Cys Pro Pro Asp Gly Gly Val Ser Ser Val Gln Arg Arg
        115                 120                 125

Arg Val Ala Ala Arg Ile Ala Ala Glu Thr Gly Ala Tyr His Pro Asp
    130                 135                 140

Gln His Asn His Pro Gly Asn Gly Asn Gly Tyr Thr Gly Leu Ala Arg
145                 150                 155                 160

Glu Leu Val Glu Gln Leu Gly Asp Val Asp Val Leu Val Ala Ala Ile
                165                 170                 175

Gly Thr Gly Gly Ser Leu Cys Gly Thr Ala Arg Ala Leu Arg Ala Ala
            180                 185                 190

Gly Ala Ser Thr His Ala Val Ala Val Glu Pro Val Gly Ser Ile Ile
        195                 200                 205
```

```
Phe Gly Gly Ala Pro Gly Ile Tyr His Gln Thr Gly Ala Gly Ser Pro
    210                 215                 220
Ala Gly Phe Pro Ile Gly Asp Asn Val Asp Arg Ser Val Ile Gly Glu
225                 230                 235                 240
Ala His Arg Val Ser Asp Ser Asp Ala Phe Ala Gly Ala Arg Val Val
                245                 250                 255
Ala Arg Arg Thr Gly Val Leu Val Gly Gly Thr Gly Gly Ala Ile
                260                 265                 270
His Val Ala Leu Arg Arg Leu Tyr Ala Tyr Pro Ala Gly Ser Val Val
            275                 280                 285
Val Val Leu Cys Asn Asp Ala Gly Glu Lys Tyr Leu Asp Ser Val Tyr
290                 295                 300
Asp Asp Glu Trp Leu Arg Ala Arg Gly Val Leu Asp Glu Leu Ala His
305                 310                 315                 320
Arg Arg Met Asp Arg Trp Phe Ala Thr Tyr Ala Glu Ser Val Lys Val
                325                 330                 335
Ala Thr Arg Asp Arg Ala Val Arg Thr Pro Val Ala Val Gly Gly
            340                 345                 350
```

<210> SEQ ID NO 52
<211> LENGTH: 1059
<212> TYPE: DNA
<213> ORGANISM: Amycolatopsis japonicum
<220> FEATURE:
<223> OTHER INFORMATION: orf 1664

<400> SEQUENCE: 52

```
atgacgatcg tccggcgcgc gtccgacctg atcgggaaca cgccgctgct ggagctcgcg     60
cgtaccggca ccgggacgcg tctgctgctc aaactcgacc acctcaaccc caccggctcg    120
tgcaaggtac gcatggcgag gcagatgatc gacgaggcgg agctggacgg acggctgcgg    180
ccgggcgggc atatcgtcga acccacgtcc ggcaacaccg gaacgggct cgccctggtc    240
gcgctggaac gcggctaccg gttcaccgcc gtggtcgatc accacgccgc ccgcgagaaa    300
ctcgggatgc tgcgcgcgct cggcgcggaa ctggtgttcg tcgaatgccc gccggacggc    360
ggggtcagtt cggtccagcg gcggcgggtc gcggcccgca tcgccgcgga aaccggtgcc    420
taccatcccg atcagcacaa ccatcccggc aacggcaacg ggtacaccgg gctggcgcgg    480
gaactcgtcg agcagctcgg cgacgtcgac gtgctcgtcg cggcgatcgg caccggcggc    540
tccctgtgcg gtacggcccg cgccctgcgc gcggcgggag cgagcaccca cgcggtggcg    600
gtcgaacctg tcggctcgat catcttcggt ggtgcgccgg ggatctacca ccagaccggg    660
gcgggcagcc cggccggttt cccgatcggg gacaacgtcg accggtcggt gatcggcgaa    720
gcccaccgcg tttccgacag cgacgcgttc gccggggccc gcgtcgtcgc caggcgcacc    780
ggcgtgctgg tcggcgggac caccggcggc gcgatccacg tcgcgctgcg gcggctttac    840
gcgtatccgg ccgaaagcgt cgtcgtggtg ctgtgcaacg acgcggggga gaagtacctc    900
gattcggtgt acgacgacga atggctgcgc gccaggggcg tactcgacga actggcccac    960
cgccggatgg accgctggtt cgccacctac gccgaatccg tgaaggtcgc cacgcgcgac   1020
cgggcggtgc gccggacccc ggtggcggtg ggcggatga                          1059
```

<210> SEQ ID NO 53
<211> LENGTH: 460
<212> TYPE: PRT
<213> ORGANISM: Amycolatopsis japonicum
<220> FEATURE:

<223> OTHER INFORMATION: ORF 1665

<400> SEQUENCE: 53

```
Met Ser Thr Ala Val Thr Thr Arg Gly Tyr Arg Ala Leu Ala Gly Leu
1               5                   10                  15

Ala Ala Pro Ile Ala Gly Ile Gln Leu Ala Gln Val Ala Leu Thr Ser
            20                  25                  30

Val Asp Leu Ala Met Leu Gly Leu Gly Val Thr Ala Val Ala Ala
        35                  40                  45

Gly Gly Leu Ala Ile Leu Leu Tyr Asn Gln Ile Arg Thr Met Cys Val
    50                  55                  60

Gly Met Val Thr Gly Val Gly Asn Leu Val Ala Thr Ala Ala Gly Ala
65                  70                  75                  80

Gly Glu Leu Arg Thr Gly Thr Gly Glu Leu Asp Glu Arg Ala Arg Asp
                85                  90                  95

Glu Ile Arg Ser Leu Leu Arg Ser Ala Leu Leu Val Ala Thr Leu Thr
            100                 105                 110

Ala Ala Leu Gly Ala Ala Val Leu Cys Gly Leu Ala Val Ala Leu Pro
        115                 120                 125

Ser Leu Gly Gln Lys Pro Glu Ile Val Ser Leu Ala Gly Pro Met Met
130                 135                 140

Phe Ala Leu Ala Gly Gly Leu Phe Pro Met Val Trp Leu Asn Val Val
145                 150                 155                 160

Arg Gln Phe Ala Val Gly Leu Arg Arg Pro Gly Ser Leu Leu Ala Val
                165                 170                 175

Thr Leu Val Ser Ile Ala Val Asn Ala Ala Leu Asn Ala Ala Phe Ile
            180                 185                 190

Tyr Gly Trp Ala Gly Leu Pro Glu Leu Gly Val Ala Gly Ile Gly Leu
        195                 200                 205

Ala Thr Thr Leu Val Gln Phe Phe Thr Leu Ala Val Phe Ala Ser Ala
210                 215                 220

Leu Arg Arg Asp Pro Leu Leu Arg Pro Met Val Ser Leu Ala Leu Trp
225                 230                 235                 240

Arg Ala Asp Arg Ala Val Val Arg Ile Val Arg His Gly Thr Pro
                245                 250                 255

Ile Cys Phe Thr Tyr Gly Ser Glu Ala Ala Ile Thr Ser Ile Ala Thr
            260                 265                 270

Met Leu Met Gly Ala Phe Gly Pro Ala Met Leu Ala Ala Ser Asn Val
        275                 280                 285

Ala Asn Gln Leu Ala Tyr Ile Val Tyr Gln Ala Asn Ile Gly Leu Ser
290                 295                 300

Gln Gly Ser Ser Ile Leu Val Ser Arg Ala Val Ala His Gly Asp Arg
305                 310                 315                 320

Asp Arg Ala Pro Val Ile Ala Arg Gln Ala Phe Thr Leu Ser Trp Ser
                325                 330                 335

Leu Met Ala Val Val Ser Leu Ala Tyr Leu Leu Val Pro Gln Val Leu
            340                 345                 350

Leu Trp Pro Phe Leu His Asp Glu Thr Asp Ala Val Val Leu Gly Thr
        355                 360                 365

Ala Ser Thr Leu Leu Val Phe Ala Ile Ala Gln Gln Tyr Ser Lys Gly
370                 375                 380

Thr Gln Asn Ile Leu Val Gly Leu Leu Arg Gly Leu Gly Asp Thr Val
385                 390                 395                 400
```

Ser Gly Leu Arg Cys Thr Leu Val Gly Tyr Trp Ala Val Gly Val Pro
         405                 410                 415

Ala Met Phe Leu Cys Ala Tyr Val Phe Ala Trp Gly Gly Trp Gly Val
             420                 425                 430

Trp Ala Gly Leu Cys Leu Gly Phe Ala Thr Thr Ala Val Leu Leu Gly
         435                 440                 445

Arg Ser Phe Ala Gly Gln Gly Ala Gly Ser Ala Arg
     450                 455                 460

<210> SEQ ID NO 54
<211> LENGTH: 1383
<212> TYPE: DNA
<213> ORGANISM: Amycolatopsis japonicum
<220> FEATURE:
<223> OTHER INFORMATION: orf 1665

<400> SEQUENCE: 54

```
atgagcacgg cggtgacgac ccgcggctac cgggccctcg ccgggctggc cgcgccgatc      60
gcgggaatcc agctggcaca ggtcgcgctc accagcgtcg acctggccat gctcgggctg     120
ctcggggtga ccgcggtggc ggcgggcggg ctggcgatcc tgctctacaa ccagatccgc     180
accatgtgcg tcggcatggt caccggcgtc gggaacctcg tggcgacggc ggccggggcc     240
gggaactcc gcaccggcac cggcgaactc gacgagcggg cgcgggacga gatccggtcg     300
ctcctgcggt cggcgctgct cgtcgcgacc ctgaccgcgg cgctcggcgc ggccgtcctt     360
tgtggactgg ccgtcgcgct gccttcgctc ggccagaaac cggagatcgt ttcgctcgcc     420
ggtccgatga tgttcgcact ggccggcggg ctgttcccga tggtgtggct gaacgtggtg     480
cgccagttcg ccgtcgggtt gcggcggccg ggttcgctcc tcgccgtgac gctggtgtcg     540
atcgcggtca acgccgccct caacgccgcc ttcatctacg gctgggcggg tctgcccgag     600
ctgggcgtcg ccggtatcgg cctggcgacg accttggtcc agttcttcac gctcgccgtg     660
ttcgcctcgg ccctccggcg ggacccgctg ttgcgcccca tggtgtcgct cgcgctgtgg     720
cgcgcggatc gggcggtggt ccggcgcatc gtccggcacg ggacgccgat ctgcttcacc     780
tacggctcgg aggcggcgat cacctcgatc gcgacgatgc tgatgggtgc gttcggcccg     840
gcgatgctcg ccgcgtcgaa cgtcgcgaac cagctcgcct acatcgtcta ccaggccaac     900
atcgggctgt cgcaaggatc gtccattttg gtcagccgcg cggtcgccca cggtgaccgg     960
gatcgcgcac cggtgatcgc cgccaggcg ttcaccctct cctggtcctt gatggcggtg    1020
gtgagcctgg cgtacctgct ggtgccgcag gtgctgctgt ggccgttcct gcacgacgag    1080
accgacgcgg tggtgctcgg cacggcgtcg accctgctgg tgttcgccat cgcgcagcag    1140
tacagcaagg gaacgcagaa catcctcgtc ggcctgctgc gcgggctcgg tgacaccgtc    1200
tccggcctcc gctgcacgct cgtggggtac tgggcggtgg gcgtgcccgc gatgttcttg    1260
tgcgcctacg tgttcgcctg gggcggctgg ggggtctggg ccgggctgtg tctcggcttc    1320
gcgacgaccg cggtcctgct cggacggagt ttcgccggtc agggagccgg ttctgcgcga    1380
tag                                                                  1383
```

<210> SEQ ID NO 55
<211> LENGTH: 313
<212> TYPE: PRT
<213> ORGANISM: Amycolatopsis japonicum
<220> FEATURE:
<223> OTHER INFORMATION: ORF 1666

<400> SEQUENCE: 55

Met Thr Thr Thr Gly Arg Ile Gly Ile Ala Asp Val Glu Cys Leu Glu
1               5                   10                  15

Asn Ala Val Asp Thr Leu Arg Ala Leu Asp Tyr Arg Gln Gly Gly Ala
            20                  25                  30

Phe Ser His Asp Ala Val His Val Val Lys Ser Val Ser Leu Leu Leu
        35                  40                  45

Thr Trp Gly Ala Val Pro Gly Gly Leu Arg Ser Arg Leu Leu Thr Val
    50                  55                  60

Leu Ala Asp Leu His Asn Leu Leu Gly Trp Thr Glu Phe Asp Ile Gly
65                  70                  75                  80

Arg Arg Val Pro Ala Arg Leu Arg Phe Asp Arg Ala Leu Gly Leu Ala
                85                  90                  95

Ala Ala Ala Gly Asn Asp Asn Leu Met Ala Asn Ile Cys Tyr Arg Leu
            100                 105                 110

Gly Arg Leu Ala Leu His His Asp Asp Val Glu Gly Gly Leu Asp His
        115                 120                 125

Leu Arg Gln Gly Gln Ala Ala Ala His Arg Ser Gly Ser Leu Arg Ala
130                 135                 140

Gln Ala Ile Leu Thr Ile Asn Glu Ala Trp Ala Leu Ala Lys Ala Gly
145                 150                 155                 160

Asp Glu Arg Ala Ala Leu Thr Ser Leu Ala Arg Ala Glu Cys Glu Phe
                165                 170                 175

Glu Asn Ala Gly Thr Trp Ala Ala Pro Arg Pro Trp Glu Ala Phe Phe
            180                 185                 190

Gly Ala Thr Asp Met Ala Ala Met Arg Gly Thr Val Leu Thr Glu Leu
        195                 200                 205

Ala Arg Thr Val Ala Ser Arg His Ser Glu Glu Ala Ile Glu Arg Leu
210                 215                 220

Arg Asp Ala Val Asp Gly Tyr Gly Ala Glu Met Ser Arg Ser Leu Ala
225                 230                 235                 240

Leu Thr Leu Ile Met Leu Ala Gln Asn His Ala Leu Gln Gly Asp Phe
                245                 250                 255

Gly Glu Ala Val Arg Thr Gly Asp Glu Ala Leu Asp Leu Ala Arg Gly
            260                 265                 270

Leu Gly Ser Thr Arg Thr Lys Asp Arg Leu Ala Pro Leu Ala Ala Leu
        275                 280                 285

Leu Arg Gly Asp Ala Asp Pro Ala Ser Arg Asp Leu Leu Ala Arg Ile
290                 295                 300

Asp Arg Tyr Arg Ala Glu Pro Ala Pro
305                 310

<210> SEQ ID NO 56
<211> LENGTH: 942
<212> TYPE: DNA
<213> ORGANISM: Amycolatopsis japonicum
<220> FEATURE:
<223> OTHER INFORMATION: orf 1666

<400> SEQUENCE: 56
atgacaacga ccggccgtat cggtatcgcc gacgtcgaat gtctcgaaaa cgcggtcgat    60
actctgcgcg cgttggacta tcggcagggc ggcgcctttt cccacgacgc ggtgcacgtc   120
gtgaagtcgg tcagcctgct gctcacttgg ggcgccgtcc ccggcggact ccggtcacgg   180
ttgctgaccg tgctcgcgga tctgcacaat ctgctgggct ggacggaatt cgacatcggc   240

-continued

```
cgccgcgttc cggcacggct ccggttcgac cgcgcgctcg gtctcgccgc cgcggcgggc    300
aacgacaatc tcatggccaa catctgttac cgcctcggca ggctggcgtt gcatcatgac    360
gacgtcgaag gcgggttgga ccatctccgg caaggccaag ccgccgccca ccgctccggt    420
tccctgcggg cccaggcgat cctgacgatc aacgaggcgt gggcactggc caaggccggt    480
gacgagcgcg cggccctcac gagcctggcg cgggcggagt gcgagttcga aacgcgggc     540 acctgggcgg cgccacgacc gtgggaagcc ttcttcggcg ccacggacat ggccgcgatg    600
cgcgggaccg tcctgaccga attggccagg acggtcgcct cccggcacag cgaagaagcg    660
atcgagcggt tacgcgacgc cgtcgacggc tacggcgccg agatgtcccg cagcctcgcg    720
ctcaccttga tcatgctcgc gcagaaccac gcgctccagg gcgacttcgg cgaagccgtc    780
cgcaccggcg acgaggcgct ggaccctcgc cggggcctcg gttccacccg caccaaggac    840
cggctcgcac cgctggcggc acttctgcgc ggagacgccg atcccgcctc ccgcgacctg    900
ctcgcccgga tcgaccgcta tcgcgcagaa ccggctccct ga                      942
```

<210> SEQ ID NO 57
<211> LENGTH: 140
<212> TYPE: PRT
<213> ORGANISM: Amycolatopsis japonicum
<220> FEATURE:
<223> OTHER INFORMATION: ORF 1667

<400> SEQUENCE: 57

```
Met Ser Asp Phe Glu Ala Gln Leu Arg Ala Val Ser Leu Arg Val Thr
 1               5                  10                  15

Arg Pro Arg Leu Ala Val Leu Ala Ala Leu Arg Asp His Pro His Val
            20                  25                  30

Asp Thr Glu Thr Val Ile Ala Leu Val Arg Ala Asp Leu Pro Thr Val
        35                  40                  45

Ser His Gln Ala Val Tyr Asp Val Leu Arg Ala Leu Thr Glu Thr Gly
    50                  55                  60

Leu Ile Arg Arg Ile Gln Pro Ala Gly Ala Leu Ala Arg Tyr Glu Thr
65                  70                  75                  80

Arg Val Gly Asp Asn His His Val Val Cys Arg Ser Cys Gly Ala
                85                  90                  95

Ile Ala Asp Val Asp Cys Ala Val Gly His Ala Pro Cys Leu Thr Ala
            100                 105                 110

Ser Gly Asp His Gly Phe Val Ile Asp Glu Ala Glu Val Val Tyr Trp
        115                 120                 125

Gly Leu Cys Pro Gly Cys Ala Ala Glu Pro Val Gln
    130                 135                 140
```

<210> SEQ ID NO 58
<211> LENGTH: 423
<212> TYPE: DNA
<213> ORGANISM: Amycolatopsis japonicum
<220> FEATURE:
<223> OTHER INFORMATION: orf 1667

<400> SEQUENCE: 58

```
atgtccgact tcgaggcaca gctgcgagcg gtttcgttgc gcgtgacgcg gcctcggctg     60
gccgtgctcg cggcgctgcg cgatcatccg cacgtcgaca ccgaaacggt gatcgcgctg    120
gtgcgggccg atctgccgac ggtctcgcac caggcggtgt acgacgtgct gcgggcgctc    180
accgaaaccg gtctgatccg gcggatccag cccgccggcg cgctcgcccg ttacgagacc    240
```

-continued

```
cgggtgggggg acaaccatca ccatgtcgtg tgccgttcct gcggtgcgat cgcggacgtc    300
gattgcgccg tcggccatgc ccctgtctc accgcttcgg gcgatcacgg gttcgtgatc     360
gacgaggcgg aggtcgtcta ctggggcctg tgccccggct gtgcggccga acctgtccag    420
tga                                                                  423
```

```
<210> SEQ ID NO 59
<211> LENGTH: 744
<212> TYPE: PRT
<213> ORGANISM: Amycolatopsis japonicum
<220> FEATURE:
<223> OTHER INFORMATION: ORF 1668

<400> SEQUENCE: 59
```

| Met | Ser | Asp | Asn | Pro | Glu | Lys | Gly | Cys | Pro | Val | Ala | His | Asp | Ser | Val |
|---|---|---|---|---|---|---|---|---|---|---|---|---|---|---|---|
| 1 | | | | 5 | | | | | 10 | | | | | 15 | |

| Thr | Ala | His | Gly | Ser | Glu | Ser | Glu | Asn | Pro | Ala | Ile | Asp | Ser | Pro | Thr |
| | | | 20 | | | | | 25 | | | | | 30 | | |

| Pro | Lys | Ser | Gly | Gly | Arg | Pro | Arg | Thr | Asn | Lys | Asp | Trp | Trp | Pro | Asn |
| | | 35 | | | | | 40 | | | | | 45 | | | |

| Gln | Leu | Asp | Leu | Ser | Val | Leu | His | Ala | His | Ser | Ser | Lys | Ser | Asn | Pro |
| 50 | | | | | 55 | | | | | 60 | | | | | |

| Leu | Gly | Ala | Asp | Phe | Ser | Tyr | Ala | Lys | Glu | Phe | Ala | Lys | Leu | Asp | Val |
| 65 | | | | | 70 | | | | | 75 | | | | | 80 |

| Glu | Ala | Leu | Lys | Arg | Asp | Ile | Thr | Glu | Val | Leu | Thr | Thr | Ser | Gln | Asp |
| | | | | 85 | | | | | 90 | | | | | 95 | |

| Trp | Trp | Pro | Ala | Asp | Phe | Gly | His | Tyr | Gly | Gly | Leu | Met | Ile | Arg | Met |
| | | | 100 | | | | | 105 | | | | | 110 | | |

| Ser | Trp | His | Ala | Ala | Gly | Thr | Tyr | Arg | Ile | His | Asp | Gly | Arg | Gly | Gly |
| | | 115 | | | | | 120 | | | | | 125 | | | |

| Ala | Gly | Asp | Gly | Ala | Gln | Arg | Phe | Ala | Pro | Leu | Asn | Ser | Trp | Pro | Asp |
| 130 | | | | | 135 | | | | | 140 | | | | | |

| Asn | Ala | Asn | Leu | Asp | Lys | Ala | Arg | Arg | Leu | Leu | Trp | Pro | Val | Lys | Glu |
| 145 | | | | | 150 | | | | | 155 | | | | | 160 |

| Lys | Tyr | Gly | Gln | Gln | Ile | Ser | Trp | Ala | Asp | Leu | Leu | Val | Leu | Ala | Gly |
| | | | | 165 | | | | | 170 | | | | | 175 | |

| Asn | Val | Ala | Leu | Glu | Ser | Met | Gly | Phe | Lys | Thr | Phe | Gly | Phe | Gly | Phe |
| | | | 180 | | | | | 185 | | | | | 190 | | |

| Gly | Arg | Val | Asp | Thr | Trp | Glu | Pro | Glu | Glu | Ile | Phe | Trp | Gly | Pro | Glu |
| | | 195 | | | | | 200 | | | | | 205 | | | |

| Asp | Thr | Trp | Leu | Gly | Asp | Glu | Arg | Tyr | Ala | Ser | Asp | Thr | Glu | Met | Val |
| 210 | | | | | 215 | | | | | 220 | | | | | |

| Pro | Asp | Val | Gly | Ala | Thr | Glu | Met | Gly | Leu | Ile | Tyr | Val | Asn | Pro | Glu |
| 225 | | | | | 230 | | | | | 235 | | | | | 240 |

| Gly | Pro | Arg | Gly | Asn | Ala | Asp | Pro | Ala | Ala | Ala | His | Phe | Ile | Arg |
| | | | | 245 | | | | | 250 | | | | | 255 |

| Glu | Thr | Phe | Ala | Arg | Met | Ala | Met | Asn | Asp | Glu | Glu | Thr | Val | Ala | Leu |
| | | | 260 | | | | | 265 | | | | | 270 | | |

| Ile | Ala | Gly | Gly | His | Thr | Phe | Gly | Lys | Thr | His | Gly | Ala | Gly | Ile | Ala |
| | | 275 | | | | | 280 | | | | | 285 | | | |

| Asp | Asp | His | Val | Gly | Pro | Glu | Pro | Glu | Ala | Ala | Pro | Leu | Glu | Thr | Gln |
| | | 290 | | | | | 295 | | | | | 300 | | | |

| Gly | Leu | Gly | Trp | Leu | Ser | Thr | His | Gly | Ser | Gly | Lys | Gly | Ala | Asp | Ala |
| 305 | | | | | 310 | | | | | 315 | | | | | 320 |

| Ile | Thr | Ser | Gly | Leu | Glu | Val | Thr | Trp | Thr | Asp | Lys | Pro | Thr | Gln | Trp |

-continued

```
               325                 330                 335
Ser Asn Arg Phe Phe Glu Ile Leu Phe Gly Tyr Glu Trp Glu Leu Thr
            340                 345                 350
Thr Ser Pro Gly Gly Ala Lys Gln Tyr Val Ala Lys Asp Ala Glu Ala
            355                 360                 365
Ile Ile Pro Asp Ala His Asp Pro Ala Lys Lys His Lys Pro Thr Met
370                 375                 380
Leu Thr Thr Asp Leu Ala Leu Arg Val Asp Pro Glu Tyr Glu Lys Ile
385                 390                 395                 400
Ser Arg Arg Phe Leu Glu Asn Pro Asp Asp Phe Ala Leu Ala Phe Ala
                405                 410                 415
Lys Ala Trp Tyr Lys Leu Leu His Arg Asp Met Gly Pro Val Ser Arg
                420                 425                 430
Phe Leu Gly Pro Trp Val Pro Glu Pro Gln Leu Trp Gln Asp Pro Val
                435                 440                 445
Pro Asp Val Asp His Glu Leu Val Gly Asp Ala Asp Ile Ala Ala Leu
            450                 455                 460
Lys Thr Lys Val Leu Glu Ser Gly Leu Thr Val Glu Gln Leu Val Gly
465                 470                 475                 480
Thr Ala Trp Ala Ser Ala Ala Ser Phe Arg Ser Thr Asp Lys Arg Gly
                485                 490                 495
Gly Ala Asn Gly Ala Arg Ile Arg Leu Ala Pro Gln Arg Asp Trp Glu
                500                 505                 510
Val Asn Arg Pro Glu Glu Leu Ala Ser Val Leu Glu Thr Leu Glu Gly
                515                 520                 525
Ile Gln Arg Glu Phe Asn Asp Ala Gly Gly Ala Lys Ile Ser Leu Ala
                530                 535                 540
Asp Leu Ile Val Leu Ala Gly Thr Ala Ala Val Glu Lys Ala Ala Arg
545                 550                 555                 560
Asp Ala Gly Thr Asp Val Thr Val Ala Phe His Pro Gly Arg Thr Asp
                565                 570                 575
Ala Thr Gln Glu Asp Thr Asp Val Glu Ser Phe Thr Leu Leu Glu Pro
                580                 585                 590
Arg Ala Asp Gly Phe Arg Asn His Leu Arg Pro Glu Glu Lys Leu Gln
                595                 600                 605
Pro Glu Val Leu Leu Val Glu Arg Ala Tyr Met Leu Asp Leu Thr Ala
                610                 615                 620
Pro Glu Met Thr Val Leu Val Gly Gly Leu Arg Ala Leu Gly Ile Thr
625                 630                 635                 640
Ala Gly Asp Thr Arg His Gly Val Leu Thr Asp Arg Pro Gly Val Leu
                645                 650                 655
Thr Asn Asp Phe Phe Thr Asn Leu Leu Ser Pro Gly Thr Arg Trp Lys
                660                 665                 670
Val Ser Glu Ser Glu Glu Asn Val Tyr Glu Ile Arg Asp Ala Gly Thr
                675                 680                 685
Asp Ala Val Lys Trp Thr Ala Thr Pro Val Asp Leu Val Phe Gly Ser
                690                 695                 700
Asn Ser Gln Leu Arg Ala Leu Ser Glu Val Tyr Ala Gly Gln Ala Gly
705                 710                 715                 720
Arg Glu Arg Phe Ala Ala Asp Phe Ala Lys Ala Trp Thr Lys Val Met
                725                 730                 735
Glu Leu Asp Arg Phe Asp Leu Asp
                740
```

<210> SEQ ID NO 60
<211> LENGTH: 2235
<212> TYPE: DNA
<213> ORGANISM: Amycolatopsis japonicum
<220> FEATURE:
<223> OTHER INFORMATION: orf 1668

<400> SEQUENCE: 60

| | |
|---|---:|
| atgagtgaca acccggagaa gggctgcccg gtgcccacg actccgtgac cgcgcacgga | 60 |
| agtgagagcg agaacccggc gatcgactcg ccgacgccga atcgggcgg ccgcccgcgt | 120 |
| accaacaagg actggtggcc caaccagctc gacctctcgg tgctgcacgc ccactcgtcg | 180 |
| aagtcgaacc cgctcggcgc ggacttcagc tacgccaagg aattcgccaa actcgacgtc | 240 |
| gaggccctca acgcgacat caccgaggtg ctcaccacct cgcaggactg gtggcccgca | 300 |
| gacttcggcc actacggcgg cctgatgatc cggatgagct ggcacgccgc gggcacctac | 360 |
| cgcatccacg acgccgagg cggcgccggt gacggcgcgc agcggttcgc cccgctcaac | 420 |
| agctggcccg acaacgccaa cctcgacaag gcacggcggc tgctgtggcc ggtcaaggag | 480 |
| aagtacggcc agcagatctc gtgggccgac ctgctcgtgc tcgccgggaa cgtcgcgctg | 540 |
| gagtcgatgg ggttcaagac gttcggcttc ggtttcggcc gcgtggacac ctgggagccc | 600 |
| gaggagatct tctggggtcc ggaagacacc tggctgggtg acgagcgcta cgcgagcgac | 660 |
| accgagatgg tccccgacgt cggcgcgacc gaaatgggcc tcatctacgt caaccccgag | 720 |
| ggacccccgag gcaacgcgga cccggccgcc gcggcgcatt tcatccggga gaccttcgcc | 780 |
| cggatggcga tgaacgacga ggagaccgtc gcgctcatcg ccgggggcca ccttcggc | 840 |
| aagacccacg gtgccggtat cgccgacgac cacgtcggcc cggaacccga agccgcccg | 900 |
| ctcgagacac agggcctcgg ctggctgagc acccacggca gcggcaaggg cgccgacgcg | 960 |
| atcaccagcg gtctcgaggt gacgtggacc gacaagccga cgcagtggag caaccggttc | 1020 |
| ttcgagatcc tcttcggcta cgaatgggaa ctcaccacca gcccgggcgg cgccaagcag | 1080 |
| tacgtcgcca aggacgccga ggcgatcatc ccggacgccc acgacccggc caagaagcac | 1140 |
| aagccgacca tgctcaccac ggatctcgcg ctgcgcgtcg accggagta cgagaagatc | 1200 |
| tcgcgccgct tcctggagaa cccggacgac ttcgcgctcg cgttcgccaa ggcctggtac | 1260 |
| aaaactgctgc accgcgacat gggcccggtc agccgtttcc tggggccgtg ggtgcccgaa | 1320 |
| ccgcagctgt ggcaggaccc ggtgccggac gtcgaccacg aactcgtggg gacgccgac | 1380 |
| atcgccgcgc tcaagacgaa ggtgctcgag tccgggctca cggtcgagca gctggtcggc | 1440 |
| acggcgtggg cgtccgcggc gagcttccgg tccaccgaca acgcggcgg cgccaacggg | 1500 |
| gcccggatcc gcctggcacc ccagcgtgac tgggaggtca accggccgga agagctcgcg | 1560 |
| agtgtgctgg agaccctgga gggcatccag cgcgagttca cgacgccgg tggcgccaag | 1620 |
| atctcgctgg ccgacctgat cgtgctggcg ggcactgccg ccgtcgagaa ggcggcgcgc | 1680 |
| gacgcgggca ccgacgtgac cgtggcgttc caccccggcc gcaccgacgc cacccaggag | 1740 |
| gacaccgacg tcgagtcgtt cacgctgctc gaaccgcggg ccgacgggtt ccgcaaccac | 1800 |
| ctgcgtcccg aggagaaact gcagccggag gtcctgctgg tcgagcgcgc ctacatgctc | 1860 |
| gacctgaccg cgcccgagat gaccgtcctc gtcggcggcc tgcgtgcgct cgggatcacc | 1920 |
| gccggcgaca cccggcacgg cgtcctcacc gaccggcccg gcgtgctcac caacgacttc | 1980 |
| ttcaccaacc tcctctcgcc gggcacccgg tggaaggtgt cggagtccga ggagaacgtg | 2040 |

-continued

```
tacgagatcc gcgacgccgg cacggacgcg gtgaagtgga cggcgacccc ggtcgacctc    2100
gtgttcggct ccaactcgca gctgagggcg ctttccgagg tctatgcggg tcaggccggg    2160
cgggagcggt tcgccgccga cttcgccaag gcgtggacca aggtcatgga actggaccgg    2220
ttcgacctcg actga                                                     2235
```

<210> SEQ ID NO 61
<211> LENGTH: 137
<212> TYPE: PRT
<213> ORGANISM: Amycolatopsis japonicum
<220> FEATURE:
<223> OTHER INFORMATION: ORF 5768

<400> SEQUENCE: 61

```
Met Ser Pro Thr Thr Ala Asn Ser Ser Ala Pro Val Pro Gly Arg Arg
1               5                   10                  15

Ser Thr Lys Gln Arg Ala Ala Val Val Glu Leu Leu Lys Glu Ile Asp
            20                  25                  30

Asp Phe Arg Ser Ala Gln Glu Leu His Asp Glu Leu Arg Lys Arg Gly
        35                  40                  45

Asp Gly Ile Gly Leu Thr Thr Val Tyr Arg Thr Leu Gln Ser Leu Ser
    50                  55                  60

Glu Ala Gly Glu Ile Asp Val Leu Arg Thr Asp Thr Gly Glu Ala Ile
65                  70                  75                  80

Tyr Arg Arg Cys Ser Ser His His His His Leu Val Cys Arg Leu
                85                  90                  95

Cys Gly Ser Thr Val Glu Val Glu Gly Pro Ala Val Glu Arg Trp Ala
            100                 105                 110

Glu Lys Ile Ala Ser Glu His Gly Phe Ser Asp Ile Ser His Thr Val
        115                 120                 125

Glu Ile Val Gly Thr Cys Ser Asn His
    130                 135
```

<210> SEQ ID NO 62
<211> LENGTH: 414
<212> TYPE: DNA
<213> ORGANISM: Amycolatopsis japonicum
<220> FEATURE:
<223> OTHER INFORMATION: orf 5768

<400> SEQUENCE: 62

```
atgagtccga cgacggccaa cagttccgcg ccggtgccgg gacgccggtc gacgaaacag     60
cgggccgccg tggtcgagct gctcaaggag atcgacgact tccgttctgc ccaggaactg    120
cacgacgagc tgcgcaaacg cggcgacggc atcgggctca ccacggtgta ccggacgctg    180
cagtcgctgt ccgaggccgg cgagatcgac gtcctgcgca cggacaccgg cgaggccatc    240
taccggcgtt gctcgtcgca ccaccaccat cacctggtgt gccgtctctg cggcagcacg    300
gtcgaggtcg agggccccgc ggtggagcgg tgggccgaga gatcgcttc ggagcacggc    360 ttctccgaca tcagccacac cgtggagatc gtcgggacct gctcgaacca ctga         414
```

<210> SEQ ID NO 63
<211> LENGTH: 1869
<212> TYPE: DNA
<213> ORGANISM: Amycolatopsis japonicum
<220> FEATURE:
<223> OTHER INFORMATION: ds orf 5768

<400> SEQUENCE: 63

```
aatcatatgg tcgggacctg ctcgaaccac tgacgagcgc tatgaaaggt cctttcctgg      60
caaattttgc aaggaaagga cctttcatag catcggctca gtactcgtaa gggtccttcg     120
gcgccggcac ctgccgcacc gaggtgagcg tcaaatccgg catgtagctg ttctcccgta     180
ccgcggtccc cggcacgacc gtcccggtga cctccagcca ggtgtcgttc ccgaagcccg     240
acacgccgtc gcccaccatc cgcacggtga tcgggaaggc gtcggccgcg cagcagccga     300
tgaccatccg cgccagcatc gtgttgccct cgttgtgcac gacgaagccg acagccgca     360
ccgtgcgccc gttcaacgag ccactggaat cccatcccgc gcggctgacg aactcgttga     420
cctccagcgg gaccacgtcc ccggcggca agggcgggaa ggcggccgcg ttgctcgccg     480
aagcgctctg tggcgccctg gcctcggtgc gggtcaccga atcggcgccc agcgcgggcg     540
gcgcgaccag gaacacggcc agcacgggca ccatcagcag ccaggccgag cgggtgttgt     600
ggtcgtgcgc gtggacatcg ccggacacga cggcggcggc ccgcgcggcc agcaggtcgc     660
ggacgatcgc gaccgcgccc agcgccacca tcaccgcgcc gcccgcgatg atccacggct     720
gctgggcggg tttgacgtag cgcaggtagt cgccgttgat cgtgatcttc agcagcgcgc     780
cgccgagcag gatcagcagg atgttctggg tctcgcgttt cacgcgccac ctccgaggat     840
caacacaccc gacacgacgg cgcacgacag cgcgaccacg aacgtcaccg gcgcgaaccg     900
gagcgcgaag gacttgccaa aggtgccggt ctgcagggcg aacagcttca cgtcgatcgc     960
gggcccgacc accaggaaca ccagtttcgg cagcagcggc atcgcggtca gcgacgcggc    1020
gacgaaggcg tcggcctcac tgcacagggc cagcacgacg gcgagcacgg ccatcaccag    1080
cacccccgagc acgatctgct ccccccagcac tccgaaccac ttggcgggca ccagcacgtt    1140
catcgcggcg gcgatcatcg cgccgagcac caggaaaccg ccggcctcga ccagatccgc    1200
ccgcgcggtc tcggcgaagg tcttccagcg cgaaccgtgc tgaacctccg gaagccgccg    1260
caaagcccgc tccgcgatcc agtcgagctt gccccacttc gcccacagcc agcccatcac    1320
catcgcggtg gcgagcgaac cggcgaagcg ggcgaacacc atttccgggt tcccggggaa    1380
cgccaccgcc gtcgcgacca gcaccaccgg gttcaccgcg ggcgcggcga gcaggaaggt    1440
cagcgcggcc gcgggcgcga cgccctggcc gatcaggcgc cgcgcgaccg gcaccgacgc    1500
gcattcacac ccggcagggc gaccccggcc agccccgcga cgccgacggc cgcaccggcc    1560
cggcgaggga gcaccttctc cagcaccgcg cggggcacga acgccgcgat cgcgccgctg    1620
atcagcaccc cgagcaccag gaacggcagc gcctgcacgc agacggcgac gaacacggtc    1680
gagccggtcc gcagcgcggg cacgtcgaac acctgctgga gccagctctg cccgaggatc    1740
gcgatcagca ggatcgcgca gagcacctcg atcgaggtga tcttgaaccg ccgggccggc    1800
ttcttctccg gggcgcttct ggaaatggtt tccatgcgcg cgatgatgcc aggtgaccgt    1860
tctagatta                                                            1869
```

<210> SEQ ID NO 64
<211> LENGTH: 1537
<212> TYPE: DNA
<213> ORGANISM: Amycolatopsis japonicum
<220> FEATURE:
<223> OTHER INFORMATION: us orf 5768

<400> SEQUENCE: 64

```
aataagcttg tttcgcgacg aagttcttcg ggatcgagca gctcacgccg ccgagcacga      60
gcgtcgtgcg ggcctcgcgc agatccttgc ccgcgtcgtc gcgcacgtgc gtgacgatgt     120
ccaccttcca gcccgccacc gcggtcacgt cgccgttgcg ccagccgtcc tgccggatca     180
```

```
gctggtcgaa ggcggtcacg cgggacacgg tcaggtcgga ggtggtctcg tccttgccga    240
tgttctcgtt cttgatgacc gacggcgggc cgagcttgag ccccttgacg tcgacgcccg    300
aagcgccgga cggcttgagc gcgccggttt cgtcccgcac ccagatcttg ccacgctcg    360 tcgacgacgt cgccttgctg ggcgacgagc agtcgacggc gctcttggcg ccttcaagca    420
ccagtacggt gttgtcggcg ggcttcgcgc ctccgcgccc gttgtcgagc agggcgtagt    480
tgctctccgc gaccgccgtc gggaccgtgg tctgctgcag cgcggcgagc acgttgtggt    540
cgcggctggc gataccgggc gggaacgggc tctgggcgcc gaagcggccc aggttgacag    600
cccatttgtc gccgaaggtg ttcttctcgc cgtcgtcacg cgggacgacg gtgcggtccg    660
gggagagttt cgactggcct ggcgtcagcg gcgagcgctg ggtctcggtg atcagcgatc    720
ccgggttccc gatgcgcacc gacgccacat tcgcgaacga cacggggccg gtcttctcat    780
cgacggcctg cgtcgtctgc gccgaggcga gccccggaac cgacgccaaa gcgacggccg    840
ccgtcgcggc ggccagcttc gtcacgaaac gagtcatgtc tccccactgc ctctccgggc    900
cctcagagcg cggtcgtcag cgtacgaaa gcgacgaaac gctccgcgac aaccttgcac    960
cgttggcgac cacatgcgaa gtggaatggt catttctttg ctaagtcacc cgaatggagc   1020
agtaacatcg ccgccaagtg gtcgcccggt cggcgaacag accaccgggg gcgggaacac   1080
taggatgggc aggactgtta ctggcaatga cttcggaaat catgatggac atggaggcgg   1140
cgatggctac ggtgaccccg gactctgccg ccccgggct ctcggaggac cccgggccgc   1200
attcgtcggc ccgtccccc gccgaacccg cgacgtcggc ctcgcccgcc gtcctcgcgg   1260
acgccggcga cctgctcagg gcgctcgccg cgcccgtgcg catcgccatc gtcctgcagt   1320
tgcgtaacgc ggacaggtgc gtgcacgaac tggtggacac actcgatgtc gcgcagccgc   1380
tgatcagcca gcacctgcgg gtgctgaaga cggcgggtgt cgtacagggt gagcgacgcg   1440
gccgtgaggt ggtgtaccgg ctggtcgacg atcaccttgc gcatatcgtg gtggacgccg   1500
tagcccacgt tcaggagggg aagtgagcca tatgatt                            1537
```

<210> SEQ ID NO 65
<211> LENGTH: 139
<212> TYPE: PRT
<213> ORGANISM: Streptomyces coelicolor

<400> SEQUENCE: 65

```
Val Thr Thr Ala Gly Pro Pro Val Lys Gly Arg Ala Thr Arg Gln Arg
1               5                   10                  15

Ala Ala Val Ser Ala Ala Leu Gln Glu Val Glu Phe Arg Ser Ala
            20                  25                  30

Gln Glu Leu His Asp Met Leu Lys His Lys Gly Asp Ala Val Gly Leu
        35                  40                  45

Thr Thr Val Tyr Arg Thr Leu Gln Ser Leu Ala Asp Ala Gly Glu Val
    50                  55                  60

Asp Val Leu Arg Thr Ala Glu Gly Glu Ser Val Tyr Arg Arg Cys Ser
65                  70                  75                  80
```

-continued

```
Thr Gly Asp His His His Leu Val Cys Arg Ala Cys Gly Lys Ala
            85              90                  95

Val Glu Val Glu Gly Pro Ala Val Glu Lys Trp Ala Glu Ala Ile Ala
        100             105                 110

Ala Glu His Gly Tyr Val Asn Val Ala His Thr Val Glu Ile Phe Gly
        115             120                 125

Thr Cys Ala Asp Cys Ala Gly Ala Ser Gly Gly
130                 135
```